(12) United States Patent
Tateishi et al.

(10) Patent No.: US 8,585,781 B2
(45) Date of Patent: Nov. 19, 2013

(54) AZO COMPOUND, AQUEOUS SOLUTION, INK COMPOSITION, INK FOR INKJET RECORDING, INKJET RECORDING METHOD, INK CARTRIDGE FOR INKJET RECORDING, AND INKJET RECORD

(71) Applicant: FUJIFILM Corporation, Tokyo (JP)

(72) Inventors: Keiichi Tateishi, Manchester (GB); Yoshihiko Fujie, Manchester (GB); Shigeaki Tanaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/753,757

(22) Filed: Jan. 30, 2013

(65) Prior Publication Data

US 2013/0139723 A1 Jun. 6, 2013

Related U.S. Application Data

(63) Continuation of application No. PCT/JP2011/067193, filed on Jul. 28, 2011.

(30) Foreign Application Priority Data

| Jul. 30, 2010 | (JP) | 2010-173181 |
| Jan. 31, 2011 | (JP) | 2011-019344 |
| Jun. 29, 2011 | (JP) | 2011-145021 |

(51) Int. Cl.
*C09B 67/00* (2006.01)
*C09D 11/00* (2006.01)

(52) U.S. Cl.
USPC .......... 8/566; 8/568; 8/571; 8/575; 106/31.52

(58) Field of Classification Search
USPC .............. 8/566, 568, 571, 575; 106/31.52
See application file for complete search history.

(56) References Cited

U.S. PATENT DOCUMENTS

| 2005/0061201 A1* | 3/2005 | Takasaki et al. ............ 106/31.52 |
| 2005/0204952 A1 | 9/2005 | Wachi et al. |
| 2006/0162616 A1 | 7/2006 | Chino et al. |
| 2007/0109376 A1 | 5/2007 | Tojo et al. |

FOREIGN PATENT DOCUMENTS

| JP | 2004115776 A | 4/2004 |
| JP | 2005120346 A | 5/2005 |
| JP | 2005139427 A | 6/2005 |
| JP | 2005307177 A | 11/2005 |
| JP | 2007009081 A | 1/2007 |
| JP | 2007099825 A | 4/2007 |
| JP | 2008001881 A | 1/2008 |
| JP | 2009132794 A | 6/2009 |
| WO | 2010041065 A1 | 4/2010 |

OTHER PUBLICATIONS

STIC Search Report dated Mar. 19, 2013.*
International Search Report (PCT/ISA/210) dated Sep. 13, 2011 issued by the International Searching Authority in counterpart International Application No. PCT/JP2011/067193.
Written Opinion (PCT/ISA/237) dated Sep. 13, 2011 issued by the International Searching Authority in counterpart International Application No. PCT/JP2011/067193.

* cited by examiner

*Primary Examiner* — Eisa Elhilo
(74) *Attorney, Agent, or Firm* — Sughrue Mion, PLLC

(57) ABSTRACT

There is provided an aqueous solution including: (a) a preservative, and (b) at least one kind of an azo compound represented by the following Formula (1) or a salt thereof, wherein a content of (b) is 1% by mass to 25% by mass:

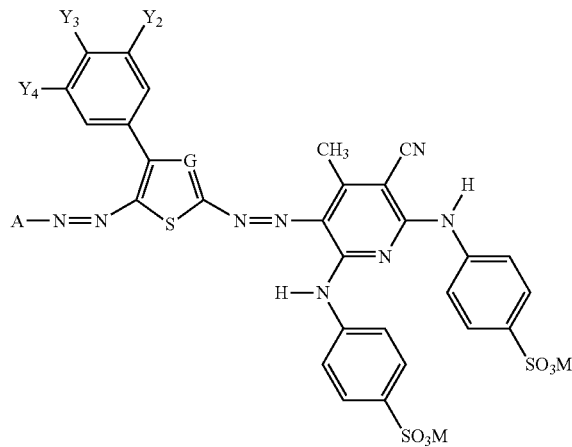

Formula (1)

wherein, in Formula (1), A represents a substituted phenyl group or a substituted or unsubstituted nitrogen-containing 5-membered heterocyclic group, G represents a nitrogen atom or $-C(R_2)=$, $R_2$ represents a hydrogen atom, a sulfo group, a carboxy group, a substituted or unsubstituted carbamoyl group or cyano group, $Y_2$, $Y_3$ and $Y_4$ each independently represents a hydrogen atom or a monovalent substituent, $Y_2$, $Y_3$ and $Y_4$ may be bonded to each other to form a ring, all of $Y_2$, $Y_3$ and $Y_4$ do not represent a hydrogen atom at the same time, and M each independently represents a hydrogen atom or a monovalent countercation.

18 Claims, No Drawings

AZO COMPOUND, AQUEOUS SOLUTION, INK COMPOSITION, INK FOR INKJET RECORDING, INKJET RECORDING METHOD, INK CARTRIDGE FOR INKJET RECORDING, AND INKJET RECORD

CROSS REFERENCE TO RELATED APPLICATIONS

This application is a continuation of International Application No. PCT/JP2011/067193 filed Jul. 28, 2011, and claims priority from Japanese Patent Application Nos. 2010-173181 filed Jul. 30, 2010, 2011-019344 filed Jan. 31, 2011, and 2011-145021 filed Jun. 29, 2011, the contents of all of which are incorporated herein by reference in their entirety.

TECHNICAL FIELD

The present invention relates to an azo compound, an aqueous solution, an ink composition, ink for inkjet recording, an inkjet recording method, an ink cartridge for inkjet recording, and an inkjet record.

BACKGROUND ART

An inkjet recording method is rapidly spread and more developed because material cost is low, high-speed recording is feasible, a noise is low while recording is performed, and color recording is easy.

The inkjet recording method includes a continuous manner that continuously disperses a liquid drop and an on-demand manner that disperses a liquid drop according to an image information signal as the inkjet recording method, and a discharging manner includes a manner that discharges a liquid drop by applying pressure by a piezo element, a manner that discharges a liquid drop by generating bubbles in ink by heat, a manner that uses an ultrasonic wave, and a manner that draws a liquid drop by electrostatic force and discharge it. Further, aqueous ink, oily ink, or solid (melt type) ink is used as ink for inkjet recording.

A colorant used in ink for inkjet recording needs to ensure favorable solubility or polydispersity to a solvent, recording at a high concentration, favorable hue, fastness to light, heat, and active gas ($NO_x$, $SO_x$ other than oxidative gas such as ozone, or the like) in an environment, excellent fastness to water or chemicals, good fixability to an image-receiving material, low spreading, excellent preservation as ink, non-toxicity, high purity, and availableness at low price. However, it is very difficult to find a colorant satisfying these requirements at a high level.

Particularly, there is a strong demand for an ink composition having a favorable black hue, fastness to light, humidity and heat, a high molar light absorbing coefficient, a high character quality in document printing, and fastness to oxidative gas such as ozone in an environment when printed on an image-receiving material having an ink receiving layer including porous white inorganic pigment particles.

In order to solve the aforementioned problems, Patent Documents 1 and 2 describe an aqueous disazo dye containing two or more heterocyclic rings.

Further, Patent Documents 3 and 4 describe an asymmetric tris or tetrakis azo compound where a benzene ring or a naphthalene ring and a heterocyclic condensed ring are bonded by an azo group as a black colorant providing a black recording image having excellent fastness of an image, particularly, both excellent light resistance and ozone gas resistance.

RELATED ART

Patent Document

Patent Document 1: Japanese Patent Application Laid-Open No. 2005-139427

Patent Document 2: Japanese Patent Application Laid-Open No. 2004-115776

Patent Document 3: Japanese Patent Application Laid-Open No. 2009-132794

Patent Document 4: Japanese Patent Application Laid-Open No. 2005-307177

DISCLOSURE OF INVENTION

Problems to be Solved by the Invention

However, recently, an inkjet recording method has been used for various purposes, and thus, an image-receiving paper needs to have printing performance such as high photographic sensitivity, a precise photographic image quality, and high grayscale reproducibility. Further, high speed recording is required, and a quick drying property and fixability of ink and fastness of the obtained image are required at higher levels.

It is known that in order to improve the quick drying property and the fixability of ink, a permeating agent (for example, a hydrophilic organic solvent) in an image-receiving layer in the image-receiving paper is used, but viscosity of recording liquid is excessively increased, and thus, there is a problem in that discharging becomes unstable because an ink discharging speed of a nozzle is reduced or surface tension is reduced. Moreover, there is a problem in that a difference in a printing concentration or the degree of spreading occurs according to a kind of recording paper.

A dye described in Patent Documents 1 and 2 has excellent fastness, but insufficient solubility to water, and thus, there is a problem in performance required for the current inkjet purpose. Further, there is a problem in that a change in quality (for example, spreading, fixability, and bronze gloss) of a record by a difference of a recording paper according to development of a recording paper occurs.

Further, examples of the compounds described in Patent Document 3 have problems in that storage stability as ink is insufficient, or a color is significantly changed (shorter wavelength) at high humidity and high temperature after printing is performed on an exclusive inkjet paper, and thus, it is yet difficult to ensure sufficient performance.

As described above, ink simultaneously satisfying various performances required in an aqueous inkjet ink has not been found yet.

An object of the present invention relates to an aqueous solution and an ink composition having a favorable hue as black ink, providing a colored image or a colored material having excellent fastness by removing a change in image quality of a record due to a difference in recording paper, and providing stable ink having a small change in physical properties, particularly, suppressed bronze gloss, even though preservation is performed over a long period of time. In addition, there is provided a method of forming an image, which provides ink for printing or recording, such as inkjet, and prevents a reduction in image quality of the formed image (a method of preventing a reduction in image quality).

Means for Solving the Problems

The present inventors have intensively studied on a dye having a favorable hue, not causing a bronze phenomenon, having a high light fastness and gas fastness (particularly, ozone gas) by removing a change in image quality of a record due to a difference in recording paper, and being stable even though preservation is performed over a long period of time in ink, and have found that the aforementioned problems can be solved by an asymmetric azo compound where an aromatic hydrocarbon ring or an aromatic heterocyclic group having a substituent are bonded to a heterocyclic ring, and a heterocyclic condensed ring by an azo group, thereby completing the present invention. More specifically, the present inventors have found that an asymmetric azo compound obtained by bonding a heterocyclic ring having a specific substituent at a specific substitution position, a specific heterocyclic ring and a specific aromatic hydrocarbon ring through an azo group has excellent properties as a colorant, and the aforementioned problems can be solved by an aqueous solution containing an azo colorant represented by Formula (1) of the present invention, particularly, an aqueous solution including an azo colorant represented by Formula (2-1) or (2-2) of the present invention, an aqueous solution including Formula (3-1), (3-2), (4-1) or (4-2) of the present invention and particularly an azo colorant represented by Formula (6) or (7) of the present invention, having (1) a specific spectroscopic absorption curve, and (2) a specific colorant structure (a specific number of a specific kind of substituents are introduced into a predetermined substitution position) thereby completing the present invention. That is, the aforementioned object of the present invention is accomplished by the following means.

[1] An aqueous solution containing (a) a preservative, and (b) at least one azo compound represented by the following Formula (1) or a salt thereof, wherein a content of (b) is 1% by mass to 25% by mass.

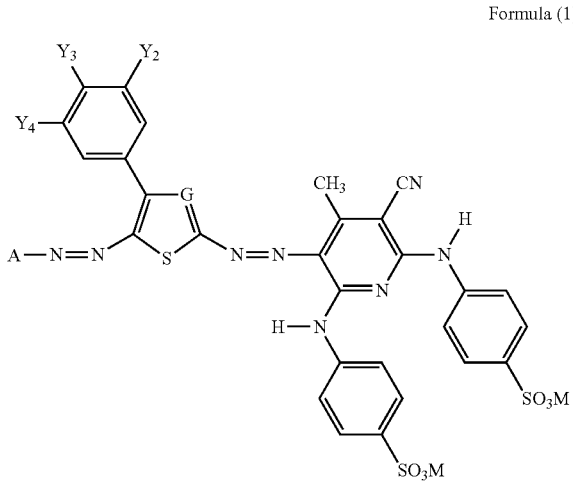

Formula (1)

In Formula (1), A represents a substituted phenyl group or a substituted or unsubstituted nitrogen-containing 5-membered heterocyclic group. G represents a nitrogen atom or —C($R_2$)=. $R_2$ represents a hydrogen atom, a sulfo group, a carboxy group, a substituted or unsubstituted carbamoyl group or cyano group. $Y_2$, $Y_3$ and $Y_4$ each independently represents a hydrogen atom or a monovalent substituent. $Y_2$, $Y_3$ and $Y_4$ may be bonded to each other to form a ring. All of $Y_2$, $Y_3$ and $Y_4$ do not represent a hydrogen atom at the same time. M each independently represents a hydrogen atom or a monovalent countercation.

[2] The aqueous solution according to [1], in which the azo compound represented by Formula (1) is an azo compound represented by the following Formula (2-1).

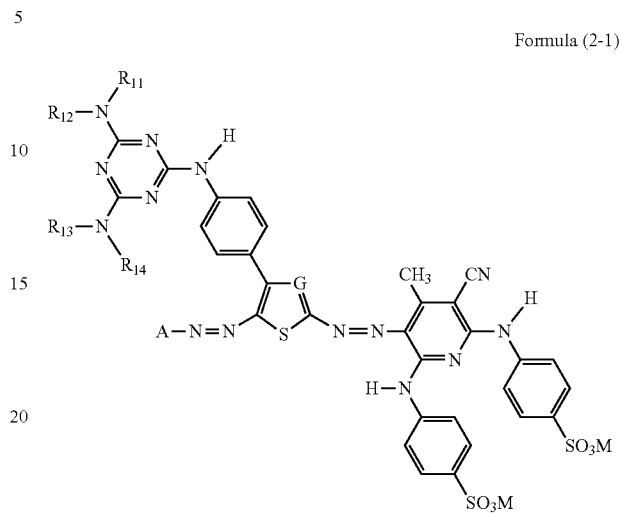

Formula (2-1)

In Formula (2-1), G represents a nitrogen atom or —C($R_2$)=. $R_2$ represents a hydrogen atom, a sulfo group, a carboxy group, a substituted or unsubstituted carbamoyl group or cyano group. $R_{11}$, $R_{12}$, $R_{13}$ and $R_{14}$ each independently represents a hydrogen atom or a monovalent substituent A represents a substituted phenyl group or a substituted or unsubstituted nitrogen-containing 5-membered heterocyclic group. M each independently represents a hydrogen atom or a monovalent countercation.

[3] The aqueous solution according to [1] or [2], in which the azo compound represented by Formula (1) or (2-1) is an azo compound represented by the following Formula (3-1).

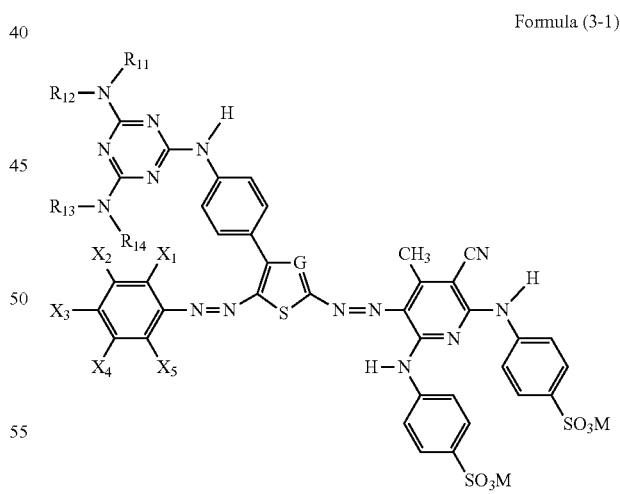

Formula (3-1)

In Formula (3-1), G represents a nitrogen atom or C($R_2$)=. $R_2$ represents a hydrogen atom, a sulfo group, a carboxy group, a substituted or unsubstituted carbamoyl group or cyano group. $R_{11}$, $R_{12}$, $R_{13}$ and $R_{14}$ each independently represents a hydrogen atom or a monovalent substituent $X_1$, $X_2$, $X_3$, $X_4$ and $X_5$ each independently represents a hydrogen atom or a monovalent substituent. M each independently represents a hydrogen atom or a monovalent countercation.

[4] The aqueous solution according to any one of [1] to [3], in which the azo compound represented by Formula (1), (2-1) or (3-1) is an azo compound represented by the following Formula (4-1).

Formula (4-1)

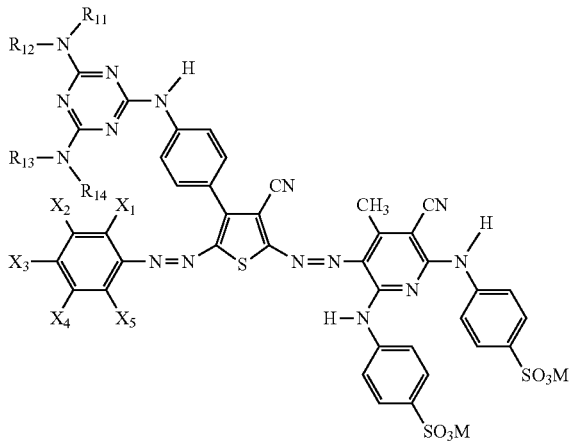

In Formula (4-1), $R_{11}$, $R_{12}$, $R_{13}$ and $R_{14}$ each independently represents a hydrogen atom or a monovalent substituent. $X_1$, $X_2$, $X_3$, $X_4$ and $X_5$ each independently represents a hydrogen atom or a monovalent substituent. M each independently represents a hydrogen atom or a monovalent countercation.

[5] The aqueous solution according to [1], in which the azo compound represented by Formula (1) is an azo compound represented by the following Formula (2-2).

Formula (2-2)

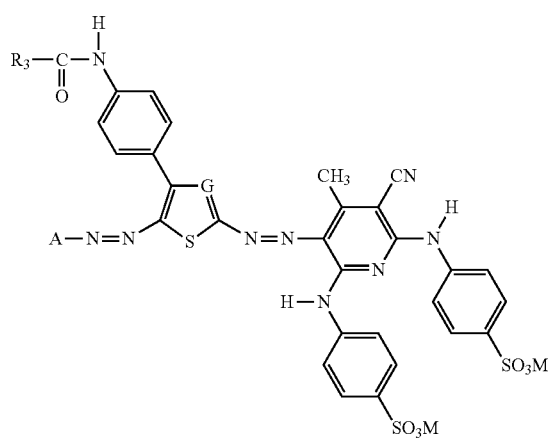

In Formula (2-2), G represents a nitrogen atom or —C($R_2$)=. $R_2$ represents a hydrogen atom, a sulfo group, a carboxy group, a substituted or unsubstituted carbamoyl group or cyano group. $R_3$ represents a monovalent substituent. A represents a substituted phenyl group or a substituted or unsubstituted nitrogen-containing 5-membered heterocyclic group. M each independently represents a hydrogen atom or a monovalent countercation.

[6] The aqueous solution according to [1] or [5], in which the azo compound represented by Formula (1) or (2-2) is an azo compound represented by the following Formula (3-2).

Formula (3-2)

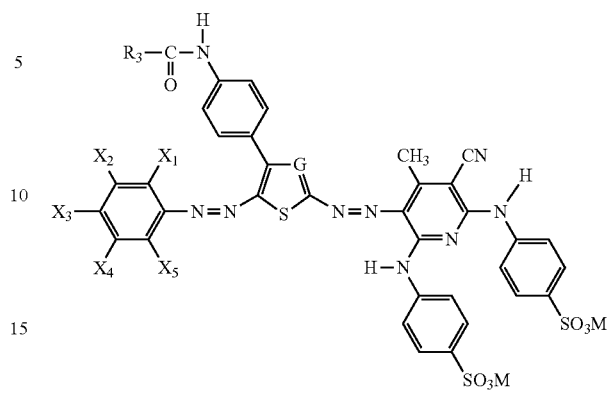

In Formula (3-2), G represents a nitrogen atom or —C($R_2$)=. $R_2$ represents a hydrogen atom, a sulfo group, a carboxy group, a substituted or unsubstituted carbamoyl group or cyano group. $R_3$ represents a monovalent substituent. $X_1$, $X_2$, $X_3$, $X_4$ and $X_5$ each independently represents a hydrogen atom or a monovalent substituent. M each independently represents a hydrogen atom or a monovalent countercation.

[7] The aqueous solution according to any one of [1], [5] and [6], in which the azo compound represented by Formula (1), (2-2) or (3-2) is an azo compound represented by the following Formula (4-2).

Formula (4-2)

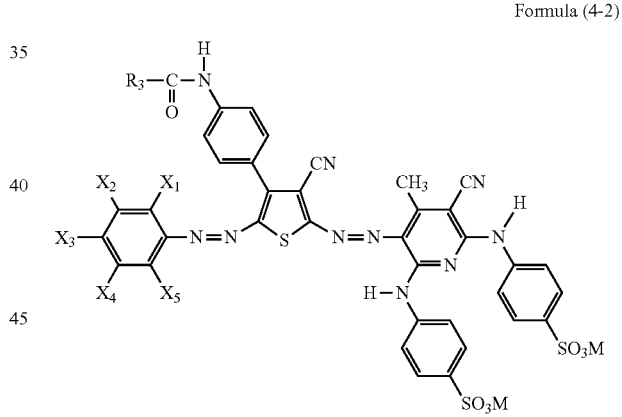

In Formula (4-2), $R_3$ represents a monovalent substituent. $X_1$, $X_2$, $X_3$, $X_4$ and $X_5$ each independently represents a hydrogen atom or a monovalent substituent. M each independently represents a hydrogen atom or a monovalent countercation.

[8] The aqueous solution according to any one of [1] to [7], in which the azo compound represented by Formula (1), (2-1), (2-2), (3-1), (3-2), (4-1) or (4-2) has at least three or more ionic hydrophilic groups.

[9] The ink composition according to any one of [1] to [8], in which in the azo compound represented by Formula (1), (2-1), (2-2), (3-1), (3-2), (4-1) or (4-2), at least one M is a lithium ion.

[10] The aqueous solution according to any one of [1] to [9], further containing (c) a pH adjusting agent.

[11] The aqueous solution according to any one of [1] to [10], in which a pH at 25° C. is 7.0 to 9.0.

[12] An ink composition including: the aqueous solution according to any one of [1] to

[13] An ink for inkjet recording, containing the aqueous solution according to any one of [1] to [11].

[14] An inkjet recording method including forming a colored image on a recording target material by using the ink for inkjet recording according to [13].

[15] An ink cartridge for inkjet recording, which is charged with the ink for inkjet recording according to [13].

[16] An inkjet record, in which a colored image is formed on a recording target material by using the ink for inkjet recording according to [13].

[17] An azo compound represented by the following Formula (3-1) or a salt thereof.

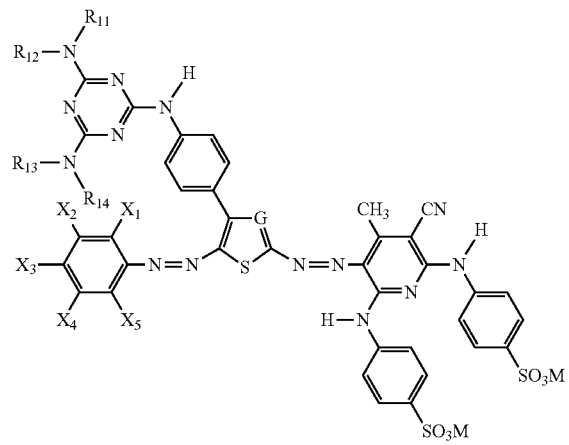

Formula (3-1)

In Formula (3-1), G represents a nitrogen atom or —C($R_2$)=. $R_2$ represents a hydrogen atom, a sulfo group, a carboxy group, a substituted or unsubstituted carbamoyl group or cyano group. $R_{11}$, $R_{12}$, $R_{13}$ and $R_{14}$ each independently represents a hydrogen atom or a monovalent substituent. $X_1$, $X_2$, $X_3$, $X_4$ and $X_5$ each independently represents a hydrogen atom or a monovalent substituent. M each independently represents a hydrogen atom or a monovalent countercation.

[18] The azo compound or the salt thereof according to [17], in which the azo compound represented by Formula (3-1) is an azo compound represented by the following Formula (4-1).

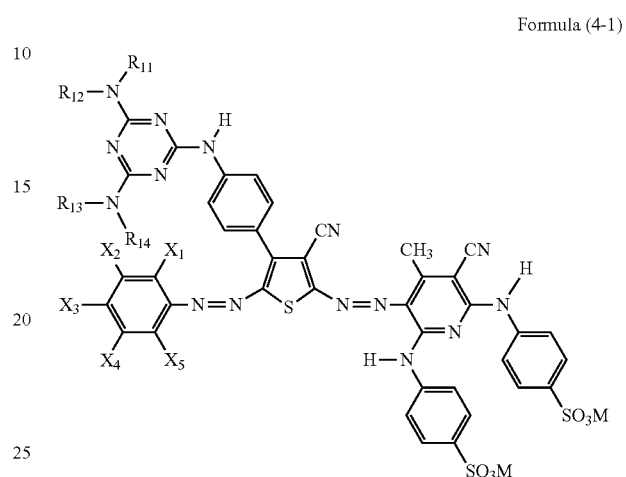

Formula (4-1)

In Formula (4-1), $R_{11}$, $R_{12}$, $R_{13}$ and $R_{14}$ each independently represents a hydrogen atom or a monovalent substituent. $X_1$, $X_2$, $X_3$, $X_4$ and $X_5$ each independently represents a hydrogen atom or a monovalent substituent. M each independently represents a hydrogen atom or a monovalent countercation.

[19] The azo compound or the salt thereof according to [18], in which the azo compound represented by Formula (4-1) is an azo compound represented by the following Formula (5).

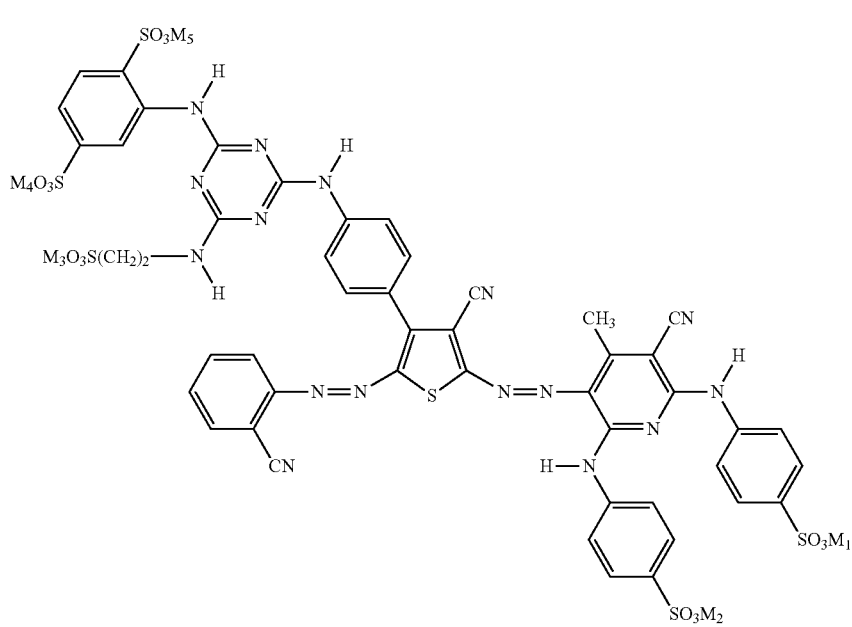

Formula (5)

In Formula (5), $M_1$, $M_2$, $M_3$, $M_4$ and $M_5$ each independently represents a hydrogen atom or a monovalent countercation, and in the case where $M_1$, $M_2$, $M_3$, $M_4$ and $M_5$ represent a monovalent countercation, $M_1$, $M_2$, $M_3$, $M_4$ and $M_5$ represent a lithium ion, a sodium ion, a potassium ion or an ammonium ion.

Effects of the Invention

The aqueous solution of the present invention is useful for an ink because the storage stability is excellent, the change in liquid properties (pH value, absorbance, viscosity and surface tension) is small, and precipitates are not generated. Specifically, the ink for inkjet recording and the inkjet recording method using the ink that includes the aqueous solution of the present invention have a high ink stability, a good hue, can form images having a high fastness to light and an active gas in the environment, especially, to ozone gas, prevent an image quality change of a record caused by the difference in recording sheets, and particularly enhance the reduced quality of printed images (bronzing suppression).

In addition, the azo compound of the present invention can be used as a dye, and is useful for aqueous inks. The ink using the azo compound of the present invention is excellent in ink storage stability, and capable of imparting colored images or colored materials having an excellent hue and fastness.

EMBODIMENTS FOR CARRYING OUT THE INVENTION

Hereinafter, the present invention will be described in detail.

First, in the present invention, Group A' of substituents, Group J of substituents, an ionic hydrophilic group, and a Hammett's substituent constant σp value will be defined.

(Group A' of Substituents)

Examples thereof may include a straight-chained or branched-chained alkyl group having 1 to 12 carbon atoms, a straight-chained or branched-chained aralkyl group having 7 to 18 carbon atoms, a straight-chained or branched-chained alkenyl group having 2 to 12 carbon atoms, a straight-chained or branched-chained alkynyl group having 2 to 12 carbon atoms, a cycloalkyl group having 3 to 12 carbon atoms, a cycloalkenyl group having 3 to 12 carbon atoms (for example, methyl, ethyl, n-propyl, i-propyl, n-butyl, i-butyl, sec-butyl, t-butyl, 2-ethylhexyl, 2-methylsulfonylethyl, 3-phenoxypropyl, trifluoromethyl and cyclopentyl), a halogen atom (for example, a chlorine atom and a bromine atom), an aryl group (for example, phenyl, 4-t-butylphenyl and 2,4-di-t-amylphenyl), a heterocyclic group (for example, imidazolyl, pyrazolyl, triazolyl, 2-furyl, 2-thienyl, 2-pyrimidinyl and 2-benzothiazolyl), a cyano group, a hydroxyl group, a nitro group, a carboxy group, an amino group, an alkyloxy group (for example, methoxy, ethoxy, 2-methoxyethoxy and 2-methylsulfonylethoxy), an aryloxy group (for example, phenoxy, 2-methylphenoxy, 4-t-butylphenoxy, 3-nitrophenoxy, 3-t-butyloxycarbonylphenoxy and 3-methoxycarbonylphenyloxy), an acylamino group (for example, acetamide, benzamide and 4-(3-t-butyl-4-hydroxyphenoxy)butaneamide), an alkylamino group (for example, methylamino, butylamino, diethylamino and methylbutylamino), an arylamino group (for example, phenylamino and 2-chloroanylino), a ureide group (for example, phenylureide, methylureide and N,N-dibutylureide), a sulfamoylamino group (for example, N,N-dipropylsulfamoylamino), an alkylthio group (for example, methylthio, octylthio and 2-phenoxyethylthio), an arylthio group (for example, phenylthio, 2-butoxy-5-t-octylphenylthio and 2-carboxyphenylthio), an alkyloxycarbonylamino group (for example, methoxycarbonylamino), an alkylsulfonylamino group and an arylsulfonylamino group (for example, methylsulfonylamino, phenylsulfonylamino and p-toluenesulfonylamino), a carbamoyl group (for example, N-ethylcarbamoyl and N,N-dibutylcarbamoyl), a sulfamoyl group (for example, N-ethylsulfamoyl, N,N-dipropylsulfamoyl and N-phenylsulfamoyl), a sulfonyl group (for example, methylsulfonyl, octylsulfonyl, phenylsulfonyl and p-toluenesulfonyl), an alkyloxycarbonyl group (for example, methoxycarbonyl and butyloxycarbonyl), a heterocyclicoxy group (for example, 1-phenyltetrazole-5-oxy and 2-tetrahydropyranyloxy), an azo group (for example, phenylazo, 4-methoxyphenylazo, 4-pyvaloylaminophenylazo and 2-hydroxy-4-propanoylphenylazo), an acyloxy group (for example, acetoxy), a carbamoyloxy group (for example, N-methylcarbamoyloxy and N-phenylcarbamoyloxy), a silyloxy group (for example, trimethylsilyloxy and dibutylmethylsilyloxy), an aryloxycarbonylamino group (for example, phenoxycarbonylamino), an imide group (for example, N-succinimide and N-phthalimide), a heterocyclicthio group (for example, 2-benzothiazolylthio, 2,4-di-phenoxy-1,3,5-triazole-6-thio and 2-pyridylthio), a sulfinyl group (for example, 3-phenoxypropylsulfinyl), a phosphonyl group (for example, phenoxyphosphonyl, octyloxyphosphonyl and phenylphosphonyl), an aryloxycarbonyl group (for example, phenoxycarbonyl), an acyl group (for example, acetyl, 3-phenylpropanoyl and benzoyl), and an ionic hydrophilic group (a carboxyl group, a sulfo group or the like). The substituents may be additionally substituted, and examples of the additional substituent may include a group selected from Group A' of substituents as described above.

(Group J of Substituents)

Examples thereof may include a halogen atom, an alkyl group, an aralkyl group, an alkenyl group, an alkynyl group, an aryl group, a heterocyclic group, a cyano group, a hydroxyl group, a nitro group, an alkoxy group, an aryloxy group, a silyloxy group, a heterocyclicoxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, an alkyl or arylsulfinyl group, an alkyl or arylsulfonyl group, an acyl group, an aryloxycarbonyl group, an alkoxycarbonyl group, a carbamoyl group, an aryl or heterocyclicazo group, an imide group, a phosphino group, a phosphinyl group, a phosphinyloxy group, a phosphinylamino group, a silyl group, and an ionic hydrophilic group. The substituents may be additionally substituted, and examples of the additional substituent may include a group selected from Group J of substituents as described above.

To be more specific, examples of the halogen atom may include a fluorine atom, a chlorine atom, a bromine atom, or an iodine atom.

Examples of the alkyl group may include straight-chained, branched-chained, and cyclic substituted or unsubstituted alkyl groups, and also include a cycloalkyl group, a bicycloalkyl group, a tricyclo structure having more ring structures, or the like. The alkyl group of the substituents described hereinafter (for example, an alkyl group of an alkoxy group and an alkylthio group) represents an alkyl group of the aforementioned concept. Specifically, the alkyl group is preferably an alkyl group having 1 to 30 carbon atoms, and for example, a methyl group, an ethyl group, an n-propyl group, an i-propyl group, a t-butyl group, a n-octyl group, an eicosyl group, a 2-chloroethyl group, a 2-cyanoethyl group, a 2-ethylhexyl group, or the like, the cycloalkyl group is preferably a substituted or unsubstituted cycloalkyl group having 3 to 30 carbon atoms, and for example, a cyclohexyl group, a cyclopentyl group, a 4-n-dodecylcyclohexyl group, or the like, and the bicycloalkyl group is preferably a substituted or unsubstituted bicycloalkyl group having 5 to 30 carbon atoms, that is, a monovalent group obtained by removing one hydrogen atom from bicycloalkane having 5 to 30 carbon atoms, and for example, a bicyclo[1,2,2]heptane-2-yl group, a bicyclo[2,2,2]octane-3-yl group, or the like.

Examples of the aralkyl group may include a substituted or unsubstituted aralkyl group, and an aralkyl group having 7 to 30 carbon atoms is preferred as the substituted or unsubstituted aralkyl group. Examples thereof may include a benzyl group and a 2-phenethyl group.

Examples of the alkenyl group may include a straight-chained, branched-chained, and cyclic substituted or unsubstituted alkenyl groups, and include a cycloalkenyl group and a bicycloalkenyl group. Specifically, the alkenyl group is preferably a substituted or unsubstituted alkenyl group having 2 to 30 carbon atoms, and for example, a vinyl group, an allyl group, a prenyl group, a geranyl group, an oleyl group, or the like, the cycloalkenyl group is preferably a substituted or unsubstituted cycloalkenyl group having 3 to 30 carbon atoms, that is, a monovalent group obtained by removing one hydrogen atom of cycloalkene having 3 to 30 carbon atoms, and for example, a 2-cyclopentene-1-yl group, a 2-cyclohexene-1-yl group, or the like, and the bicycloalkenyl group is a substituted or unsubstituted bicycloalkenyl group, preferably a substituted or unsubstituted bicycloalkenyl group having 5 to 30 carbon atoms, that is, a monovalent group obtained by removing one hydrogen atom of bicycloalkene having one double bond, and for example, a bicyclo[2,2,1]hept-2-en-1-yl group, a bicyclo[2,2,2]oct-2-en-4-yl group, or the like.

The alkynyl group may be preferably a substituted or unsubstituted alkynyl group having 2 to 30 carbon atoms, and for example, an ethynyl group, a proparyl group, a trimethylsilylethynyl group, or the like.

The aryl group may be preferably a substituted or unsubstituted aryl group having 6 to 30 carbon atoms, and for example, a phenyl group, a p-tolyl group, a naphthyl group, a m-chlorophenyl group, an o-hexadecanoylaminophenyl group, or the like.

The heterocyclic group may be preferably a monovalent group obtained by removing one hydrogen atom from a 5- or 6-membered substituted or unsubstituted aromatic or non-aromatic heterocyclic compound, more preferably a 5- or 6-membered aromatic heterocyclic group having 3 to 30 carbon atoms, and for example, a 2-furyl group, a 2-thienyl group, a 2-pyrimidinyl group, a 2-benzothiazolyl group, or the like.

The alkoxy group may be preferably a substituted or unsubstituted alkoxy group having 1 to 30 carbon atoms, and for example, a methoxy group, an ethoxy group, an isopropoxy group, a t-butoxy group, a n-octyloxy group, a 2-methoxyethoxy group, or the like.

The aryloxy group may be preferably a substituted or unsubstituted aryloxy group having 6 to 30 carbon atoms, and for example, a phenoxy group, a 2-methylphenoxy group, a 4-t-butylphenoxy group, a 3-nitrophenoxy group, a 2-tetradecanoylaminophenoxy group, or the like.

The silyloxy group may be preferably a substituted or unsubstituted silyloxy group having 0 to 20 carbon atoms, and for example, a trimethylsilyloxy group, a diphenylmethylsilyloxy group, or the like.

The heterocyclicoxy group may be preferably a substituted or unsubstituted heterocyclicoxy group having 2 to 30 carbon atoms, and for example, a 1-phenyltetrazole-5-oxy group, a 2-tetrahydropyranyloxy group, or the like.

The acyloxy group may be preferably a formyloxy group, a substituted or unsubstituted alkylcarbonyloxy group having 2 to 30 carbon atoms, or a substituted or unsubstituted arylcarbonyloxy group having 6 to 30 carbon atoms, and for example, an acetyloxy group, a pyvaloyloxy group, a stearoyloxy group, a benzoyloxy group, a p-methoxyphenylcarbonyloxy group, or the like.

The carbamoyloxy group may be preferably a substituted or unsubstituted carbamoyloxy group having 1 to 30 carbon atoms, and for example, a N,N-dimethylcarbamoyloxy group, a N,N-diethylcarbamoyloxy group, a morpholinocarbonyloxy group, a N,N-di-n-octylaminocarbonyloxy group, a N-n-octylcarbamoyloxy group, or the like.

The alkoxycarbonyloxy group may be preferably a substituted or unsubstituted alkoxycarbonyloxy group having 2 to 30 carbon atoms, and for example, a methoxycarbonyloxy group, an ethoxycarbonyloxy group, a t-butoxycarbonyloxy group, a n-octylcarbonyloxy group, or the like.

The aryloxycarbonyloxy group may be preferably a substituted or unsubstituted aryloxycarbonyloxy group having 7 to 30 carbon atoms, and for example, a phenoxycarbonyloxy group, a p-methoxyphenoxycarbonyloxy group, a p-n-hexadecyloxyphenoxycarbonyloxy group, or the like.

Examples of the amino group may include an alkylamino group, an arylamino group, a heterocyclicamino group, and the amino group may be preferably an amino group, a substituted or unsubstituted alkylamino group having 1 to 30 carbon atoms, or a substituted or unsubstituted anylino group having 6 to 30 carbon atoms, and for example, a methylamino group, a dimethylamino group, an anylino group, an N-methyl-anylino group, a diphenylamino group, a triazinylamino group, or the like.

The acylamino group may be preferably a formylamino group, a substituted or unsubstituted alkylcarbonylamino group having 1 to 30 carbon atoms, or a substituted or unsubstituted arylcarbonylamino group having 6 to 30 carbon atoms, and for example, an acetylamino group, a pyvaloylamino group, a lauroylamino group, a benzoylamino group, a 3,4,5-tri-n-octyloxyphenylcarbonylamino group, or the like.

The aminocarbonylamino group may be preferably a substituted or unsubstituted aminocarbonylamino group having 1 to 30 carbon atoms, and for example, a carbamoylamino group, a N,N-dimethylaminocarbonylamino group, a N,N-diethylaminocarbonylamino group, a morpholinocarbonylamino group, or the like.

The alkoxycarbonylamino group may be preferably a substituted or unsubstituted alkoxycarbonylamino group having 2 to 30 carbon atoms, and for example, a methoxycarbonylamino group, an ethoxycarbonylamino group, a t-butoxycarbonylamino group, a n-octadecyloxycarbonylamino group, an N-methyl-methoxycarbonylamino group, or the like.

The aryloxycarbonylamino group may be preferably a substituted or unsubstituted aryloxycarbonylamino group having 7 to 30 carbon atoms, and for example, a phenoxycarbonylamino group, a p-chlorophenoxycarbonylamino group, an m-n-octyloxyphenoxycarbonylamino group, or the like.

The sulfamoylamino group may be preferably a substituted or unsubstituted sulfamoylamino group having 0 to 30 carbon atoms, and for example, a sulfamoylamino group, an N,N-dimethylaminosulfonylamino group, an N-n-octylaminosulfonylamino group, or the like.

The alkyl or arylsulfonylamino group may be preferably a substituted or unsubstituted alkylsulfonylamino group having 1 to 30 carbon atoms, or a substituted or unsubstituted arylsulfonylamino group having 6 to 30 carbon atoms, and for example, a methylsulfonylamino group, a butylsulfonylamino group, a phenylsulfonylamino group, a 2,3,5-trichlorophenylsulfonylamino group, a p-methylphenylsulfonylamino group, or the like.

The alkylthio group may be preferably a substituted or unsubstituted alkylthio group having 1 to 30 carbon atoms, and for example, a methylthio group, an ethylthio group, an n-hexadecylthio group, or the like.

The arylthio group may be preferably a substituted or unsubstituted arylthio group having 6 to 30 carbon atoms, and for example, a phenylthio group, a p-chlorophenylthio group, an m-methoxyphenylthio group, or the like.

The heterocyclicthio group may be preferably a substituted or unsubstituted heterocyclicthio group having 2 to 30 carbon atoms, and for example, a 2-benzothiazolylthio group, a 1-phenyltetrazole-5-ylthio group, or the like.

The sulfamoyl group may be preferably a substituted or unsubstituted sulfamoyl group having 0 to 30 carbon atoms, and for example, an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, an N—(N-phenylcarbamoyl)sulfamoyl group, or the like.

The alkyl or arylsulfinyl group may be preferably a substituted or unsubstituted alkylsulfinyl group having 1 to 30 carbon atoms, or a substituted or unsubstituted arylsulfinyl group having 6 to 30 carbon atoms, and for example, a methylsulfinyl group, an ethylsulfinyl group, a phenylsulfinyl group, a p-methylphenylsulfinyl group, or the like.

The alkyl or arylsulfonyl group may be preferably a substituted or unsubstituted alkylsulfonyl group having 1 to 30 carbon atoms, or a substituted or unsubstituted arylsulfonyl group having 6 to 30 carbon atoms, and for example, a methylsulfonyl group, an ethylsulfonyl group, a phenylsulfonyl group, a p-methylphenylsulfonyl group, or the like.

The acyl group may be preferably a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocycliccarbonyl group having 2 to 30 carbon atoms, in which a carbon atom and a carbonyl group are bonded, and for example, an acetyl group, a pyvaloyl group, a 2-chloroacetyl group, a stearoyl group, a benzoyl group, a p-n-octyloxyphenylcarbonyl group, a 2-pyridylcarbonyl group, a 2-furylcarbonyl group, or the like.

The aryloxycarbonyl group may be preferably a substituted or unsubstituted aryloxycarbonyl group having 7 to 30 carbon atoms, and for example, a phenoxycarbonyl group, an o-chlorophenoxycarbonyl group, a m-nitrophenoxycarbonyl group, a p-t-butylphenoxycarbonyl group, or the like.

The alkoxycarbonyl group may be preferably a substituted or unsubstituted alkoxycarbonyl group having 2 to 30 carbon atoms, and for example, a methoxycarbonyl group, an ethoxycarbonyl group, a t-butoxycarbonyl group, an n-octadecyloxycarbonyl group, or the like.

The carbamoyl group may be preferably a substituted or unsubstituted carbamoyl group having 1 to 30 carbon atoms, and for example, a carbamoyl group, a N-methylcarbamoyl group, an N,N-dimethylcarbamoyl group, an N,N-di-n-octylcarbamoyl group, an N-(methylsulfonyl)carbamoyl group, or the like.

The aryl or heterocyclicazo group may be preferably a substituted or unsubstituted arylazo group having 6 to 30 carbon atoms, or a substituted or unsubstituted heterocyclicazo group having 3 to 30 carbon atoms, and for example, phenylazo, p-chlorophenylazo, 5-ethylthio-1,3,4-thiadiazole-2-ylazo, or the like.

The imide group may be preferably an N-succinimide group, an N-phthalimide group, or the like.

The phosphino group may be preferably a substituted or unsubstituted phosphino group having 0 to 30 carbon atoms, and for example, a dimethylphosphino group, a diphenylphosphino group, a methylphenoxyphosphino group, or the like.

The phosphinyl group may be preferably a substituted or unsubstituted phosphinyl group having 0 to 30 carbon atoms, and for example, a phosphinyl group, a dioctyloxyphosphinyl group, a diethoxyphosphinyl group, or the like.

The phosphinyloxy group may be preferably a substituted or unsubstituted phosphinyloxy group having 0 to 30 carbon atoms, and for example, a diphenoxyphosphinyloxy group, a dioctyloxyphosphinyloxy group, or the like.

The phosphinylamino group may be preferably a substituted or unsubstituted phosphinylamino group having 0 to 30 carbon atoms, and for example, a dimethoxyphosphinylamino group, a dimethylaminophosphinylamino group, or the like.

The silyl group may be preferably a substituted or unsubstituted silyl group having 0 to 30 carbon atoms, and for example, a trimethylsilyl group, a t-butyldimethylsilyl group, a phenyldimethylsilyl group, or the like.

(Ionic Hydrophilic Group)

Examples thereof may include a sulfo group, a carboxyl group, a thiocarboxyl group, a sulfino group, a phosphono group, a dihydroxyphosphino group, or the like. The sulfo group, and the carboxyl group are particularly preferred. Further, the carboxyl group, the phosphono group, and the sulfo group may be in a state of salt, examples of countercations forming the salt include an ammonium ion, an alkali metal ion (e.g., a lithium ion, a sodium ion and a potassium ion) and an organic cation (e.g., a tetramethylammonium ion, a tetramethylguanidium ion and tetramethylphosphonium), a lithium salt, a sodium salt, a potassium salt, and an ammonium salt are preferred, the lithium salt or a mixture salt including the lithium salt as a main component is more preferred, and the lithium salt is most preferred.

It is preferred that the monovalent countercation of the ionic hydrophilic group included in the azo compound of the present invention includes the lithium ion as the main component. The countercation may not be totally the lithium ion, but the concentration of the lithium ion of each ink composition is preferably 50% by mass or more based on the entire countercation of each ink composition, more preferably 75% by mass or more, still more preferably 80% by mass, and particularly preferably 95% by mass or more.

Under the condition of the aforementioned ratio, a hydrogen ion, an alkali metal ion (for example, a sodium ion, and a potassium ion), an alkali earth metal ion (for example, a magnesium ion, a potassium ion, or the like), a quaternary ammonium ion, a quaternary phosphonium ion, a sulfonium ion, or the like may be included as the countercation.

With regard to the kind and the ratio of the countercation of the colorant, since "The New Experimental Chemical Lecture 9 Analysis Chemistry" (Maruzen on 1977) by The Chemical Society of Japan, and "The 4th-ed. Experimental Chemistry Lecture 15 Analysis" (Maruzen on 1991) by The Chemical Society of Japan describe itemized discussion of a analysis method or an element, the analysis method may be selected based on the itemized discussion to perform analysis and quantification. Among the methods, it is easy to determine analysis by an analysis method such as ion chromatography, an atom absorption method, and an inductively coupled plasma spectrometer analysis method (ICP).

Any method may be used as a method of obtaining the colorant of the present invention including the lithium ion as the countercation. Examples thereof may include (1) a method of converting a countercation from another cation to a lithium ion by using an ion exchange resin, (2) a method of precipitating an acid or a salt from a system including a lithium ion, (3) a method of forming a colorant by using a raw material and a synthetic intermediate where a countercation is a lithium ion, (4) a method of introducing an ionic hydrophilic group by conversion of a functional group of a colorant of each color by using a reactive agent where a countercation is a lithium ion, and (5) a method of synthesizing a compound where a countercation of an ionic hydrophilic group of a colorant is a silver ion, and reacting the compound with a lithium halogenate solution to remove the precipitated halogenated silver, thus using a lithium ion as a countercation.

The ionic hydrophilic group in the colorant of each color may be any ionic dissociation group. Preferred examples of the ionic hydrophilic group may include a sulfo group (which may be a salt), a carboxyl group (which may be a salt), a hydroxyl group (which may be a salt), a phosphono group (which may be a salt) and a quaternary ammonium group, an acylsulfamoyl group (which may be a salt), a sulfonylcarbamoyl group (which may be a salt), sulfonylsulfamoyl group (which may be a salt), or the like.

The sulfo group, the carboxyl group or the hydroxyl group (including salts thereof) is preferred. In the case where the ionic hydrophilic group is a salt, preferred examples of the countercation may include a mixture salt of lithium, alkali metal (for example, sodium and potassium) including lithium as a main component, ammonium, and an organic cation (for example, pyridinium, tetramethylammonium and guadinium), and among the examples, the countercation is preferably a mixture salt of lithium or alkali metal including lithium as a main component, and particularly preferably a lithium salt of a sulfo group, a lithium salt of a carboxy group, and a lithium salt of a hydroxyl group.

(Hammett's Substituent Constant σp Value)

The Hammett's substituent constant σp value used in the present specification will be described.

The Hammett equation is an empirical rule proposed by L. P. Hammett in 1935 in order to quantitatively treat an effect of a substituent to reaction or equilibrium of a benzene derivative, which is extensively considered to be reasonable today. There are a σp value and a σm value as a substituent constant required in the Hammett equation, and the values are found in many general documents, and for example, are described in detail in "Lange's Handbook of Chemistry", $12^{th}$ ed., 1979 (McGraw-Hill) by J. A. Dean, or "Chemical Region", special edition, Vol. 122, pp. 96 to 103, 1979 (Nankodo). Meanwhile, in the present invention, each substituent is limited by the Hammett's substituent constant σp or described, which does not mean to be found in the aforementioned books or limited to only the substituent having a value described in the document, and in the case where the value is measured based on the Hammett equation even though the value is not described in the document, of course, even the substituent considered to be included in the aforementioned range is included. The compound according to the present invention is not a benzene derivative, but an index exhibiting an electron effect of the substituent, and the σp value is used regardless of a substitution position. In the present invention, the σp value will be used as the aforementioned meaning.

Meanwhile, in the present invention, in the case where the compound is the salt, the salt is dissociated into ions to be present in ink, but for the convenience of description, the expression "the salt is included" is used.

<Aqueous Solution>

The aqueous solution of the present invention includes (a) a preservative, and (b) at least one azo compound represented by Formula (1) or a salt thereof, in which the content of (b) is 1% by mass to 25% by mass. The content of (b) is preferably 3% by mass to 15% by mass, and more preferably 5% by mass to 12% by mass. There is an effect that storage stability of the aqueous solution is favorable and it is easy to prepare a solution of aqueous ink for inkjet by setting the content of (b) to the aforementioned range.

The pH of the aqueous solution of the present invention at 25° C. is preferably 7.0 to 9.0, and more preferably 7.5 to 8.5. There is an effect that high solution stability of the azo compound in the aqueous solution is provided and it is easy to prepare a solution of aqueous ink for inkjet by setting the pH to the aforementioned range.

The aqueous solution of the present invention may be called "an ink stock solution".

Hereinafter, the present invention will be described in more detail. First, the groups or the substituents of the formulas in the present invention will be described.

[(a) Preservative]

The aqueous solution may have a problem in that an insoluble material is generated by decomposition. In order to prevent the problem, a preservative is added to the aqueous solution of the present invention.

Various matters may be used as the preservative usable in the present invention.

First, examples of the preservative may include an inorganic-based preservative (silver ion inclusions and the like) including heavy metal ions or salts thereof. Various matters such as a quaternary ammonium salt (tetrabutylammonium chloride, cetylpyridinium chloride, benzyltrimethylammonium chloride, and the like), a phenol derivative (phenol, cresole, butylphenol, xylenol, bisphenol and the like), a phenoxy ether derivative (phenoxyethanol and the like), a heterocyclic compound (benzotriazole, PROXEL, 1,2-benzoisothiazolin-3-on, and the like), acid amides, carbamic acid, carbamates, amidineguanidines, pyridines (sodiumpyridinthion-1-oxide and the like), diazines, triazines, pyrroleimidazoles, oxazole oxazins, thiazole thiadiazines, thioureas, thiosemicarbazides, dithiocarbamates, sulfides, sulfoxides, sulfones, sulfamides, antibiotics (penicillin, tetracycline and the like), sodium dehydroacetate, sodium benzoate, ethylester p-hydroxybenzoate, and a salt thereof may be used as an organic-based preservative. Further, matters described in Antibacterial and Antifungal Handbook (Gihodo: 1986) and Antibacterial and Antifungal General Dictionary (published by The Committee of Dictionary Editors of The Society for Antibacterial and Antifungal Agents, Japan) may be used as the preservative.

The preservative is preferably a phenol derivative and a heterocyclic compound, more preferably a heterocyclic compound, and still more preferably a heterocyclic compound (PROXEL XL-II, and PROXEL GXL(S)).

The preservative may be added either alone or in combination of two kinds or more to the aqueous solution. Various matters such as an oil-soluble structure and a water-soluble structure may be used as the preservative, but a water-soluble preservative is preferred.

Among the structures, it is preferred that at least one kind of the preservative is a heterocyclic compound. In the present invention, if two kinds or more preservatives are used together, the effect of the present invention is more favorably exhibited. Preferred examples thereof may include a combination of the heterocyclic compound and the antibiotic material, a combination of the heterocyclic compound and the phenol derivative, and the like. In the case where two kinds of preservatives are combined, the content ratio is not particularly limited, but it is preferred that the ratio of preservative A/preservative B is in a range of 0.01 to 100 (mass ratio).

The addition amount of the preservative to the aqueous solution may be in the wide range, but preferably 0.001% by mass to 10% by mass, and more preferably 0.1% by mass to 5% by mass. There is an effect that microbial growth is suppressed in the aqueous solution by setting the content of the preservative within the aforementioned range.

[(b) Azo Compound Represented by Formula (1)]

The azo compound represented by Formula (1) (hereinafter, referred to as "the compound represented by Formula (1)") will be described.

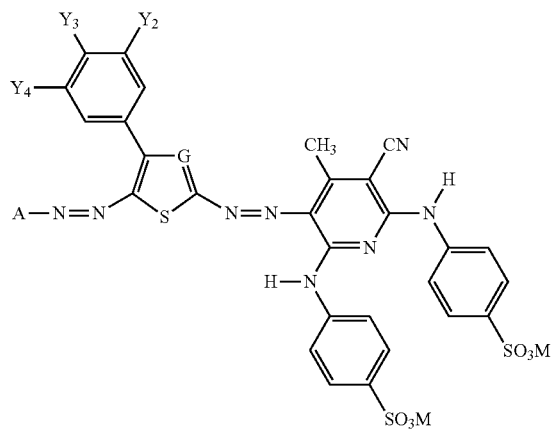

Formula (1)

(In Formula (1), A represents a substituted phenyl group or a substituted or unsubstituted nitrogen-containing 5-membered heterocyclic group. G represents a nitrogen atom or —C($R_2$)=. $R_2$ represents a hydrogen atom, a sulfo group, a carboxy group, a substituted or unsubstituted carbamoyl group or cyano group. $Y_2$, $Y_3$ and $Y_4$ each independently represents a hydrogen atom or a monovalent substituent. $Y_2$, $Y_3$ and $Y_4$ may be bonded to each other to form a ring. All of $Y_2$, $Y_3$ and $Y_4$ do not represent a hydrogen atom at the same time. M each independently represents a hydrogen atom or a monovalent countercation.)

In Formula (1), G represents a nitrogen atom or —C($R_2$)=. $R_2$ represents a hydrogen atom, a sulfo group, a carboxy group, a substituted or unsubstituted carbamoyl group or cyano group, and in the case where the carbamoyl group has a substituent, examples of the substituent may include an alkyl group (a methyl group and an ethyl group) and an aryl group (a phenyl group).

$Y_2$, $Y_3$ and $Y_4$ each independently represents a hydrogen atom or a monovalent substituent. In the case where $Y_2$, $Y_3$ and $Y_4$ represent a substituent, examples of the substituents may each independently include Group J of substituents.

In Formula (1), $Y_2$, $Y_3$ and $Y_4$ each independently represents preferably any one of a hydrogen atom, an ionic hydrophilic group, a substituted or unsubstituted amino group, a substituted or unsubstituted carbamoyl group, a substituted or unsubstituted sulfamoyl group, a substituted or unsubstituted alkylsulfonylamino group, a substituted or unsubstituted arylsulfonylamino group, and a substituted or unsubstituted acylamino group. In the case of the substituted or unsubstituted amino group, the heterocyclicamino group is preferred.

$Y_2$, $Y_3$ and $Y_4$ each independently represents more preferably any one of a hydrogen atom, an ionic hydrophilic group, a substituted or unsubstituted heterocyclicamino group, a substituted or unsubstituted alkylsulfonylamino group, a substituted or unsubstituted arylsulfonylamino group, and a substituted or unsubstituted acylamino group, and particularly preferably any one of a hydrogen atom, a substituted or unsubstituted heterocyclicamino group, a substituted or unsubstituted arylsulfonylamino group, and a substituted or unsubstituted acylamino group.

In the case where the heterocyclicamino group, the sulfamoyl group, the alkylsulfonylamino group, the arylsulfonylamino group, and the acylamino group represented by $Y_2$, $Y_3$ and $Y_4$ has a substituent, the substituent each independently represents more preferably an ionic hydrophilic group (for example, —$CO_2$M, —$SO_3$M: M is a monovalent countercation).

$Y_2$, $Y_3$ and $Y_4$ may have an additional substituent, examples of the additional substituent may include a hydroxyl group, a substituted or unsubstituted amino group, an aryl group that may have an ionic hydrophilic group, and a heterocyclic group that may have an ionic hydrophilic group, and the substituted or unsubstituted amino group is preferred. Examples of the substituent of the substituted amino group may include preferably a substituted or unsubstituted alkyl group, a substituted or unsubstituted aryl group, and a substituted or unsubstituted heterocyclic group, and more preferably an alkyl group substituted by the ionic hydrophilic group or an aryl group substituted by the ionic hydrophilic group.

The heterocyclic amino group is preferably a substituted or unsubstituted triazinylamino group, and more preferably a triazinylamino group having a substituent.

The substituent of the triazinylamino group is preferably a substituted or unsubstituted amino group, and particularly preferably a substituted or unsubstituted amino group.

The aforementioned examples are appropriately used as the substituent of the substituted amino group. Herein, in the alkyl group substituted by the ionic hydrophilic group, the alkyl group is preferably a methyl group, an ethyl group, or an n-propyl group, and more preferably an ethyl group. In the aryl group substituted by the ionic hydrophilic group, the aryl group is preferably a phenyl group.

The acylamino group is preferably an alkylcarbonylamino group, an alkylcarbonylamino group having an ionic hydrophilic group as a substituent, and an arylcarbonylamino group having an ionic hydrophilic group as a substituent. In the alkylcarbonylamino group, the alkyl group is preferably a methyl group, an ethyl group or an n-propyl group, and more preferably an ethyl group. In the arylcarbonylacyl group, the aryl group is preferably a phenyl group.

All of $Y_2$, $Y_3$ and $Y_4$ do not represent a hydrogen atom at the same time. $Y_2$, $Y_3$ and $Y_4$ may be bonded to each other to form a ring, and the ring formed by bonding $Y_2$, $Y_3$ and $Y_4$ to each other may be, for example, a benzene ring or a naphthalene ring, and is preferably a benzene ring.

Among $Y_2$, $Y_3$ and $Y_4$, it is preferred that $Y_3$ represents a substituent, and it is more preferred that $Y_2$ and $Y_4$ represent a hydrogen atom and $Y_3$ represents a substituent.

Particularly, it is most preferred that $Y_2$ and $Y_4$ represent a hydrogen atom and $Y_3$ is a heterocyclicamino group having a substituted or unsubstituted amino group as a substituent, an arylsulfonylamino group having an ionic hydrophilic group as a substituent, or an acylamino group having an ionic hydrophilic group as a substituent.

The substituent represented by $Y_2$, $Y_3$ and $Y_4$ may be more specifically the following Substituent (A1).

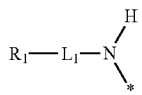

(In Substituent (A1), * represents a bonding to $Y_2$ to $Y_4$. $L_1$ represents a single bond, a carbonyl group, or a sulfonyl group. $R_1$ represents a substituted or unsubstituted alkyl group, a substituted or unsubstituted aryl group, or a substituted or unsubstituted heterocyclic group)

$R_1$ is preferably a substituted or unsubstituted alkyl group, a substituted or unsubstituted aryl group, or a substituted or unsubstituted heterocyclic group, and in the case where $R_1$ has a substituent, the substituent may be an ionic hydrophilic group, an arylamino group, or an alkylamino group.

Substituent (A1) is preferably the following Substituent (A2) or Substituent (A3).

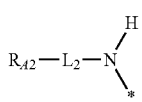

(In Substituents (A2) and (A3), * represents a bonding to $Y_2$ to $Y_4$. $L_2$ represents a carbonyl group or a sulfonyl group. $R_{A2}$ represents a substituted or unsubstituted alkyl group or a substituted or unsubstituted aryl group. $R_{A3}$ represents a substituted or unsubstituted heterocyclic group.)

$R_{A2}$ represents a substituted or unsubstituted alkyl group or a substituted or unsubstituted aryl group, and in the case where $R_{A2}$ has a substituent, the substituent is preferably an ionic hydrophilic group.

$R_{A3}$ represents a substituted or unsubstituted heterocyclic group, in the case where $R_{A3}$ has a substituent, the substituent is preferably an alkylamino group, or an arylamino group, and more preferably an alkylamino group or an arylamino group, and the groups may have additional substituents and are preferably substituted by the ionic hydrophilic group.

Substituent (A3) is preferably the following Substituent (A4).

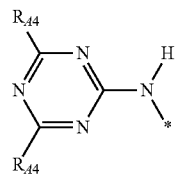

(In Substituent (A4), * represents a bonding to $Y_2$ to $Y_4$. $R_{A4}$ each independently represents a substituted or unsubstituted alkylamino group or a substituted or unsubstituted arylamino group.)

$R_{A4}$ each independently represents a substituted or unsubstituted alkylamino group or a substituted or unsubstituted arylamino group, and in the case where $R_{A4}$ has a substituent, the substituent is preferably an ionic hydrophilic group.

Specific examples of Substituent (A1) to Substituent (A4) will be described below, but are not limited thereto. * represents a bonding to $Y_2$ to $Y_4$.

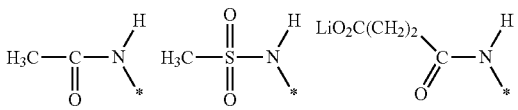

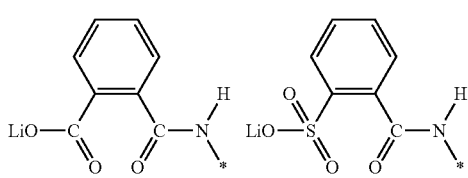

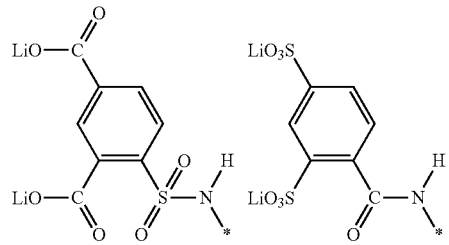

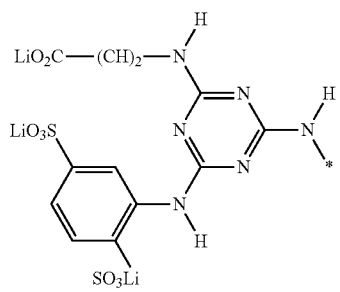

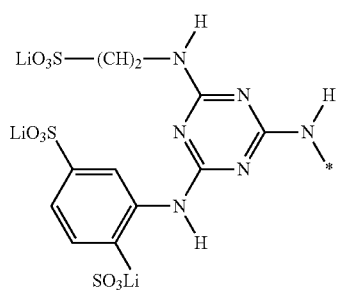

A represents a substituted phenyl group or a substituted or unsubstituted nitrogen-containing 5-membered heterocyclic group. The substituted phenyl group may be a phenyl group having Group J of substituents, and is more preferably a phenyl group having an ionic hydrophilic group or an electron-withdrawing group having a Hammett's σp value of 0.3 or more.

The nitrogen-containing heterocyclic group represented by A includes a substituted or unsubstituted nitrogen-containing heterocyclic group. The heterocyclic group represented by A is preferably a monovalent group obtained by removing one hydrogen atom from a 5-membered substituted or unsubstituted aromatic or non-aromatic heterocyclic compound, and more preferably a 5-membered aromatic heterocyclic group having 2 to 4 carbon atoms. Examples of the substituent may include groups described in the item of the aforementioned Group J of substituents. The nitrogen-containing 5-membered heterocyclic group may be a pyrrole ring, a pyrazole ring, an imidazole ring, a triazole ring, a thiazole ring, an isothiazole ring, or a thiadiazole ring as long as the substitution position is not limited.

In Formula (1), the ionic hydrophilic group is preferably —$SO_3M_1$ or —$CO_2M_1$, more preferably —$SO_3M_1$, and particularly preferably —$SO_3Li$.

$M_1$ and M each independently represents a hydrogen atom or a monovalent countercation, and the monovalent countercation may be, for example, an ammonium ion, an alkali metal ion (e.g., a lithium ion, a sodium ion and a potassium ion), or an organic cation (e.g., a tetramethylammonium ion, a tetramethylguanidium ion or a tetramethylphosphonium). The countercation other than the lithium ion is preferably a potassium ion, or a sodium ion, and more preferably a sodium ion.

The formed salt is preferably a lithium salt, a sodium salt, a potassium salt, or an ammonium salt, more preferably a lithium salt or a mixture salt including a lithium salt as a main component, and most preferably a lithium salt.

In the case where the azo compound represented by Formula (1) is the mixture salt, the salt is preferably the mixture salt of the lithium salt and the sodium salt from the viewpoints of solubility to water, viscosity of the aqueous solution, surface tension, and storage stability of the high concentration aqueous solution, may be an aspect where a portion of a plurality of M represents a lithium ion and the residual M represents a sodium ion, or may be an aspect of mixing of a dye where all M in Formula (1) represent a lithium ion and a dye where all M in Formula (1) represent a sodium ion.

In the case where M is a mixture salt of the lithium salt and the sodium salt, the molar ratio (Li:Na) of the lithium salt and the sodium salt is preferably 99:1 to 25:75, particularly preferably 99:1 to 50:50, more preferably 99:1 to 55:45, and particularly most preferably 99:1 to 65:35. Since solubility to water and a dissolution speed are favorable, it is easy to adjust viscosity of the high concentration aqueous solution and surface tension, and storage stability of the high concentration aqueous solution is excellent within the aforementioned range, it is easy to perform a treatment design of constitutional requirements of, for example, a water-soluble ink composition, particularly an ink composition of water-soluble ink for inkjet, and thus, there is an effect that an excellent raw material (a high concentration aqueous solution and an ink composition) satisfying performance required in water-soluble ink for inkjet at a high level may be provided.

The ratio of the cation of the mixture salt may be measured by ion chromatography analysis.

A particularly preferred combination as the compound represented by Formula (1) includes the following (A) to (E).

(A) G represents a nitrogen atom or —$C(R_2)$=, and is preferably —$C(R_2)$=. $R_2$ represents a hydrogen atom, a sulfo group, a carboxy group, a substituted or unsubstituted carbamoyl group, or a cyano group, is preferably a carbamoyl group (—$CONH_2$ group) or a cyano group, and more preferably a cyano group.

(B) A is preferably a substituted phenyl group, more preferably a phenyl group having an ionic hydrophilic group or an electron-withdrawing group having a Hammett's σp value of 0.3 or more, and still more preferably a phenyl group having two ionic hydrophilic groups.

(C) $Y_2$, $Y_3$ and $Y_4$ each independently preferably represents any one of a hydrogen atom, a substituted or unsubstituted heterocyclicamino group, an ionic hydrophilic group, a substituted or unsubstituted carbamoyl group, a substituted or unsubstituted sulfamoyl group, a substituted or unsubstituted alkylsulfonylamino group, a substituted or unsubstituted arylsulfonylamino group, and a substituted or unsubstituted acylamino group, more preferably any one of a hydrogen atom, a heterocyclicamino group having a substituted or unsubstituted amino group as a substituent, an ionic hydrophilic group, a substituted or unsubstituted alkylsulfonylamino group, a substituted or unsubstituted arylsulfonylamino group, and a substituted or unsubstituted acylamino group, and particularly preferably any one of a hydrogen atom, a heterocyclicamino group having a substituted or unsubstituted amino group as a substituent, an arylsulfonylamino group having an ionic hydrophilic group as a substituent, and an acylamino group having an ionic hydrophilic group as a substituent. The acylamino group is preferably an alkylcarbonylacyl group, an alkylcarbonylacyl group having an ionic hydrophilic group as a substituent, or an arylcarbonylacyl group having an ionic hydrophilic group as a substituent. In the alkylcarbonylacyl group, the alkyl group is preferably a methyl group, an ethyl group or an n-propyl group, and more preferably an ethyl group. In the arylcarbonylacyl group, the aryl group is preferably a phenyl group.

It is most preferred that $Y_2$ and $Y_4$ represent a hydrogen atom and $Y_3$ be a heterocyclicamino group having a substituted or unsubstituted amino group as a substituent, an arylsulfonylamino group having an ionic hydrophilic group as a substituent, or an acylamino group having an ionic hydrophilic group as a substituent.

(D) The ionic hydrophilic group is preferably —$SO_3M_1$ or —$CO_2M_1$, more preferably —$SO_3M_1$, and particularly preferably —$SO_3Li$.

(E) Each of $M_1$ and M independently represents a hydrogen atom or a monovalent countercation, and the monovalent countercation may be, for example, an ammonium ion, an alkali metal ion (e.g., a lithium ion, a sodium ion, and a potassium ion), or an organic cation (e.g., a tetramethylammonium ion, a tetramethylguanidium ion, or a tetramethylphosphonium), is preferably a lithium salt, a sodium salt, a potassium salt, or an ammonium salt, more preferably a lithium salt or a mixture salt including the lithium salt as a main component, and most preferably a lithium salt.

The preferred factors of this structure may be exemplified by the fact that it is possible to impart an azo colorant structure electronically and sterically, in which the water solubility of the azo compound of Formula (1) can be enhanced, and a good color and tinctorial strength and a high storage stability are compatible.

As a result, the storage stability as an aqueous solution is enhanced, and the light fastness, the heat stability, the moist heat stability, the water resistance, the gas resistance and/or the solvent resistance, which are performance requirements for inks, are considerably enhanced, thereby it being a preferred example.

It is preferred that the compound represented by Formula (1) is a compound represented by the following Formula (2-1).

Hereinafter, the compound represented by Formula (2-1) or a salt thereof will be described in detail.

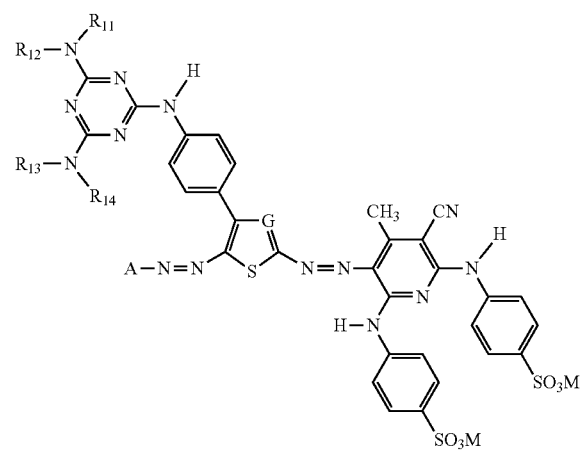

Formula (2-1)

(In Formula (2-1), G represents a nitrogen atom or —C($R_2$)=. $R_2$ represents a hydrogen atom, a sulfo group, a carboxy group, a substituted or unsubstituted carbamoyl group or cyano group. $R_{11}$, $R_{12}$, $R_{13}$ and $R_{14}$ each independently represents a hydrogen atom or a monovalent substituent. A represents a substituted phenyl group or a substituted or unsubstituted nitrogen-containing 5-membered heterocyclic group. M each independently represents a hydrogen atom or a monovalent countercation.)

Examples of G, A, $R_2$, and M in Formula (2-1) each independently have the same meaning as examples of G, A, $R_2$ and M in Formula (1), and preferred examples thereof are also the same.

In Formula (2-1), each of the monovalent substituents represented by each of $R_{11}$, $R_{12}$, $R_{13}$ and $R_{14}$ may be independently exemplified by Group A' of substituents, is preferably a substituted or unsubstituted alkyl group, a substituted or unsubstituted aryl group, or a substituted or unsubstituted heterocyclic group, and more preferably an alkyl group substituted by an ionic hydrophilic group (which may be an alkyl group having 1 to 10 carbon atoms, and is preferably a methyl group, an ethyl group, an n-propyl group, an i-propyl group, an n-butyl group, an i-butyl group, a sec-butyl group, or a t-butyl group, more preferably a methyl group, an ethyl group or an n-propyl group, and still more preferably an n-propyl group), or an aryl group substituted by an ionic hydrophilic group (which may be an aryl group having 6 to 20 carbon atoms, and is preferably a phenyl group, or a naphthyl group, and more preferably a phenyl group).

It is preferred that the compound represented by Formula (1) or (2-1) is a compound represented by the following Formula (3-1).

Hereinafter, the compound represented by Formula (3-1) or a salt thereof will be described in detail.

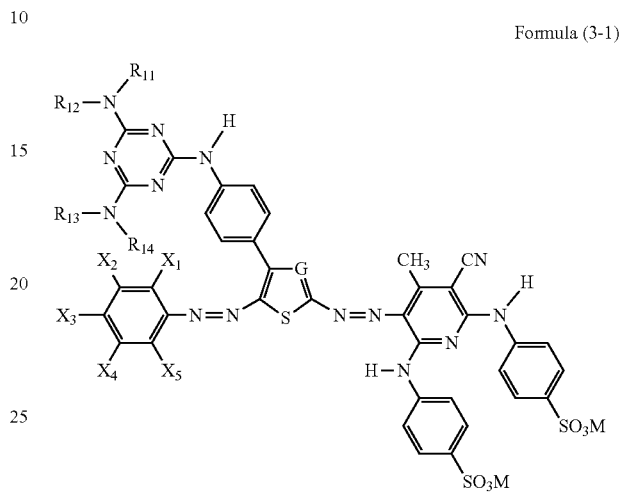

Formula (3-1)

(In Formula (3-1), G represents a nitrogen atom or —C($R_2$)=. $R_2$ represents a hydrogen atom, a sulfo group, a carboxy group, a substituted or unsubstituted carbamoyl group or cyano group. $R_{11}$, $R_{12}$, $R_{13}$ and $R_{14}$ each independently represents a hydrogen atom or a monovalent substituent. $X_1$, $X_2$, $X_3$, $X_4$ and $X_5$ each independently represents a hydrogen atom or a monovalent substituent. M each independently represents a hydrogen atom or a monovalent countercation.)

Examples of G, $R_2$, $R_{11}$, $R_{12}$, $R_{13}$, $R_{14}$ and M in Formula (3-1) each independently have the same meaning as examples of G, $R_2$, $R_{11}$, $R_{12}$, $R_{13}$, $R_{14}$ and M in Formula (2-1), and preferred examples thereof are also the same.

In Formula (3-1), $X_1$, $X_2$, $X_3$, $X_4$ and $X_5$ each independently represents a hydrogen atom or a monovalent substituent. In the case where $X_1$, $X_2$, $X_3$, $X_4$ and $X_5$ represent a substituent, the substituent may be the aforementioned Group J of substituents.

$X_1$, $X_2$, $X_3$, $X_4$ and $X_5$ each independently represents preferably a hydrogen atom, an ionic hydrophilic group, a cyano group, a substituted or unsubstituted allylsulfonyl group, a substituted or unsubstituted arylsulfonyl group, a nitro group, a substituted or unsubstituted alkoxycarbonyl group, a substituted or unsubstituted carbamoyl group, or a substituted or unsubstituted sulfamoyl group, more preferably a hydrogen atom, an ionic hydrophilic group, a cyano group, a methanesulfonyl group, a phenylsulfonyl group, a nitro group, a methoxycarbonyl group, or a carbamoyl group, or particularly preferably a hydrogen atom, an ionic hydrophilic group, or a cyano group.

In Formula (3-1), $X_2$ and $X_4$ each independently represents preferably a hydrogen atom or an ionic hydrophilic group. $X_1$, $X_3$ and $X_5$ each independently represents preferably any one of a hydrogen atom or Group J of substituents, and at least one of $X_1$, $X_3$ and $X_5$ preferably represents an electron-withdrawing group having a Hammett's σp value of 0.3 or more. The electron-withdrawing group has an upper limit of the σp value of the Hammett's substituent constant of 1.0 or less.

If at least one of $X_1$, $X_3$ and $X_5$ is the electron-withdrawing group having a σp value in the aforementioned range, it is possible to adjust a color of the azo compound and improve light fastness and ozone gas fastness, thus being useful to a water-soluble dye for inkjet recording black ink.

Specific examples of the electron-withdrawing group having a σp value of 0.3 or more may include an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanate group, a thiocarbonyl group, a halogenated alkyl group, a halogenated alkoxy group, a halogenated aryloxy group, a halogenated alkylamino group, a halogenated alkylthio group, or an aryl group, a nitro group, a heterocyclic group, a halogen atom, an azo group or a cellenocyanate group substituted by another electron-withdrawing group having a σp value of 0.3 or more. The electron-withdrawing group is preferably a cyano group, a methylsulfonyl group, a phenylsulfonyl group, a methoxycarbonyl group, a carbamoyl group, or a nitro group, and more preferably a cyano group, a methylsulfonyl group, or a nitro group.

From the viewpoints of the hue, tinctorial strength, and storage stability of water solubility, among the aforementioned matters, at least one of $X_2$ and $X_4$ is preferably an ionic hydrophilic group, it is preferred that $X_1$, $X_3$ and $X_5$ are a hydrogen atom or an electron-withdrawing group having a Hammett's σp value of 0.3 or more, and it is more preferred that $X_1$, $X_3$ and $X_5$ are a hydrogen atom and $X_2$ and $X_4$ are an ionic hydrophilic group. The ionic hydrophilic group is preferably —$SO_3M_1$ or —$CO_2M_1$ ($M_1$ represents a hydrogen atom or a monovalent countercation), more preferably —$CO_2M_1$, and particularly preferably —$CO_2Li$.

A particularly preferred combination as the compound represented by Formula (3-1) includes the following (A) to (E).

(A) $X_2$ and $X_4$ each independently represents preferably a hydrogen atom or an ionic hydrophilic group, and at least one of $X_1$, $X_3$ and $X_5$ preferably represents an electron-withdrawing group having a Hammett's σp value of 0.3 or more, is a cyano group, a methylsulfonyl group, a phenylsulfonyl group, a methoxycarbonyl group, a carbamoyl group, or a nitro group, more preferably a cyano group, a methylsulfonyl group, or a nitro group, and still more preferably a cyano group, and it is particularly preferred that $X_1$, $X_2$, $X_3$ and $X_4$ are a hydrogen atom and $X_5$ is a cyano group.

(B) G represents a nitrogen atom or —C($R_2$)=, and is preferably —C($R_2$)=. $R_2$ represents a hydrogen atom, a sulfo group, a carboxy group, a substituted or unsubstituted carbamoyl group, or a cyano group, is preferably a carbamoyl group (—$CONH_2$ group) or a cyano group, and more preferably a cyano group.

(C) The monovalent substituent represented by $R_{11}$, $R_{12}$, $R_{13}$ and $R_{14}$ may be exemplified by Group A' of substituents, and is preferably a substituted or unsubstituted alkyl group, a substituted or unsubstituted aryl group, or a substituted or unsubstituted heterocyclic group, and more preferably an alkyl group substituted by an ionic hydrophilic group or an aryl group substituted by an ionic hydrophilic group.

(D) The ionic hydrophilic group is preferably —$SO_3M_1$ or —$CO_2M_1$, more preferably —$SO_3M_1$, and particularly preferably —$SO_3Li$.

(E) $M_1$ and M each independently represents a hydrogen atom or a monovalent countercation, and the monovalent countercation may be, for example, an ammonium ion, an alkali metal ion (e.g., a lithium ion, a sodium ion, and a potassium ion), or an organic cation (e.g., a tetramethylammonium ion, a tetramethylguanidium ion, or a tetramethylphosphonium), is preferably a lithium salt, a sodium salt, a potassium salt, or an ammonium salt, more preferably a lithium salt or a mixture salt including the lithium salt as a main component, and most preferably a lithium salt.

The preferred factor of this structure may be exemplified by the fact that the water solubility of the azo compound of Formula (3-1) and association of azo dyes in an aqueous solution are considerably enhanced, and particularly, storage stability in an aqueous solution is enhanced.

As a result, the structure becomes a preferred example in that the storage stability for a long period is achieved, and the light fastness, the heat stability, the moist heat stability, the water resistance, the gas resistance and/or the solvent resistance, which are performance requirements for inks, are considerably enhanced.

It is preferred that the compound represented by Formula (1), (2-1), or (3-1) is a compound represented by the following Formula (4-1).

Hereinafter, the compound represented by Formula (4-1) or a salt thereof will be described in detail.

Formula (4-1)

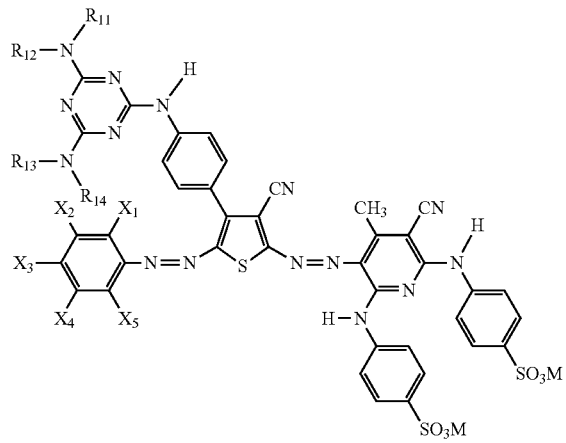

(In Formula (4-1), $R_{11}$, $R_{12}$, $R_{13}$ and $R_{14}$ each independently represents a hydrogen atom or a monovalent substituent. $X_1$, $X_2$, $X_3$, $X_4$ and $X_5$ each independently represents a hydrogen atom or a monovalent substituent. M each independently represents a hydrogen atom or a monovalent countercation.)

Examples of $R_{11}$, $R_{12}$, $R_{13}$, $R_{14}$ and M in Formula (4-1) each independently have the same meaning as examples of $R_{11}$, $R_{12}$, $R_{13}$, $R_{14}$ and M in Formula (2-1), and preferred examples thereof are also the same.

Examples of $X_1$, $X_2$, $X_3$, $X_4$ and $X_5$ in Formula (4-1) each independently have the same meaning as examples of $X_1$, $X_2$, $X_3$, $X_4$ and $X_5$ in Formula (3-1), and preferred examples thereof are also the same.

The preferred factor of this structure is that a ring including G in Formula (1) is not a nitrogen-containing 5-membered heterocyclic ring but a thiophene ring, a preservation property of image fastness of a printed matter using the ink composition of the present invention (for example, ozone gas fastness, and light fastness) may be improved, and discoloration (a change in color) and decolorization (color fading) may be presented at a higher level, and a suitability to grey to black ink requiring a small change in discoloration and decolorization is improved.

It is preferred that the compound represented by Formula (1), (2-1), (3-1), or (4-1) be a compound represented by the following Formula (5).

Hereinafter, the compound represented by Formula (5) or a salt thereof will be described in detail.

Formula (5)

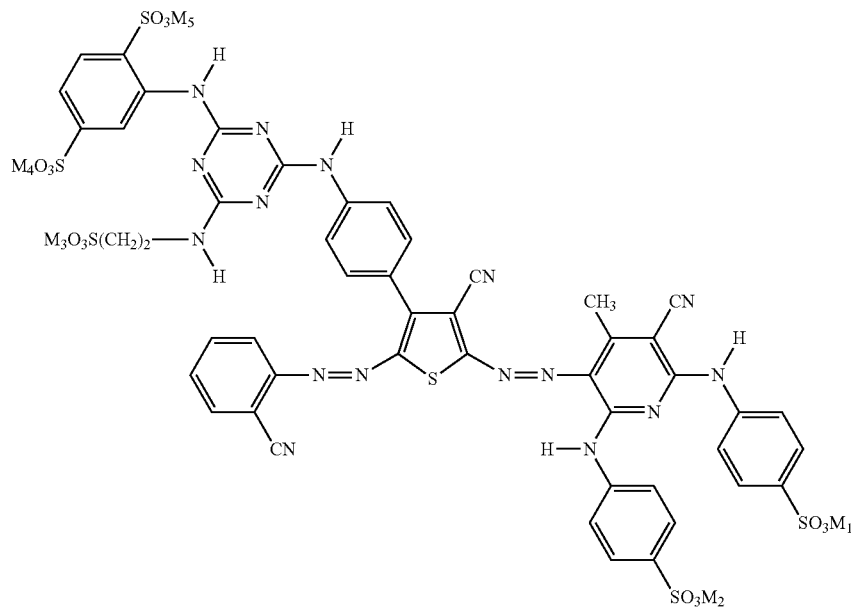

(In Formula (5), $M_1$, $M_2$, $M_3$, $M_4$ and $M_5$ each independently represents a hydrogen atom or a monovalent countercation, and in the case where $M_1$, $M_2$, $M_3$, $M_4$ and $M_5$ represent the monovalent countercation, $M_1$, $M_2$, $M_3$, $M_4$ and $M_5$ represent a lithium ion, a sodium ion, a potassium ion or an ammonium ion.)

It is also preferred that the compound represented by Formula (1) is a compound represented by the following Formula (2-2).

Hereinafter, the compound represented by Formula (2-2) or a salt thereof will be described in detail.

Formula (2-2)

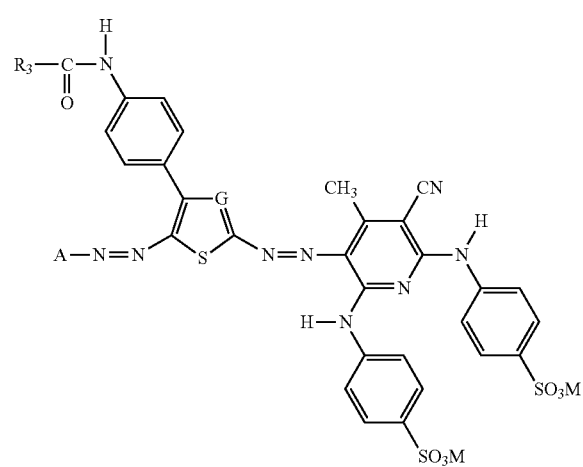

(In Formula (2-2), G represents a nitrogen atom or —C($R_2$)═. $R_2$ represents a hydrogen atom, a sulfo group, a carboxy group, a substituted or unsubstituted carbamoyl group or cyano group. $R_3$ represents a monovalent substituent. A represents a substituted phenyl group or a substituted or unsubstituted nitrogen-containing 5-membered heterocyclic group. M each independently represents a hydrogen atom or a monovalent countercation.)

Examples of A, G, $R_2$ and M in Formula (2-2) each independently have the same meaning as examples of A, G, $R_2$ and M in Formula (1), and preferred examples thereof are also the same.

In Formula (2-2), the monovalent substituent represented by $R_3$ may be exemplified by Group A' of substituents, and is preferably a substituted or unsubstituted alkyl group, a substituted or unsubstituted aryl group, or a substituted or unsubstituted heterocyclic group, more preferably an alkyl group or an aryl group substituted by an ionic hydrophilic group, and particularly preferably an alkyl group substituted by an ionic hydrophilic group.

In the alkyl group substituted by the ionic hydrophilic group, the alkyl group is preferably a methyl group, an ethyl group, or a n-propyl group, and particularly preferably an ethyl group. The ionic hydrophilic group is preferably —$SO_3M_1$ or —$CO_2M_1$ ($M_1$ represents a hydrogen atom or a monovalent countercation), more preferably —$CO_2M_1$, and particularly preferably —$CO_2Li$.

It is preferred that the compound represented by Formula (1) or (2-2) is a compound represented by the following Formula (3-2).

Hereinafter, the compound represented by Formula (3-2) or a salt thereof will be described in detail.

Formula (3-2)

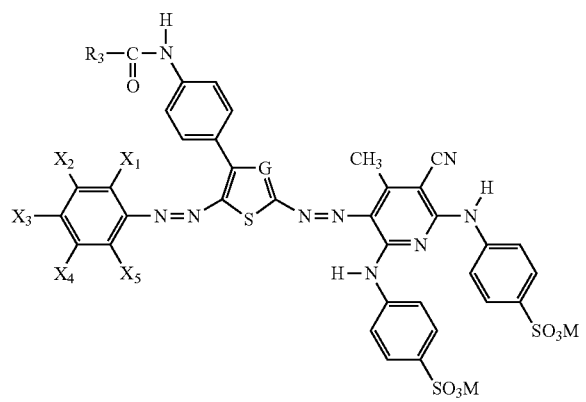

(In Formula (3-2), G represents a nitrogen atom or —C(R$_2$)=. R$_2$ represents a hydrogen atom, a sulfo group, a carboxy group, a substituted or unsubstituted carbamoyl group or cyano group. R$_3$ represents a monovalent substituent. X$_1$, X$_2$, X$_3$, X$_1$ and X$_5$ each independently represents a hydrogen atom or a monovalent substituent. M each independently represents a hydrogen atom or a monovalent countercation.)

Examples of G, R$_2$, R$_3$ and M in Formula (3-2) each independently have the same meaning as examples of G, R$_2$, R$_3$ and M in Formula (2-2), and preferred examples thereof are also the same.

In Formula (3-2), each of X$_1$, X$_2$, X$_3$, X$_4$ and X$_5$ independently represents a hydrogen atom or a monovalent substituent. In the case where X$_1$, X$_2$, X$_3$, X$_4$ and X$_5$ represent a substituent, the substituent may be the aforementioned Group J of substituents.

X$_1$, X$_2$, X$_3$, X$_4$ and X$_5$ each independently represents preferably a hydrogen atom, an ionic hydrophilic group, a cyano group, a substituted or unsubstituted alkylsulfonyl group, a substituted or unsubstituted arylsulfonyl group, a nitro group, a substituted or unsubstituted alkoxycarbonyl group, a substituted or unsubstituted carbamoyl group, or a substituted or unsubstituted sulfamoyl group, more preferably a hydrogen atom, an ionic hydrophilic group, a cyano group, a methanesulfonyl group, a phenylsulfonyl group, a nitro group, a methoxycarbonyl group, or a carbamoyl group, or particularly preferably a hydrogen atom, an ionic hydrophilic group (—SO$_3$M$_1$ or —CO$_2$M$_1$ is preferred, —CO$_2$M$_1$ is more preferred, and —CO$_2$Li is particularly preferred), or a cyano group.

In Formula (3-2), it is preferred that X$_2$ and X$_4$ each independently represents a hydrogen atom or an ionic hydrophilic group. X$_1$, X$_3$ and X$_5$ each independently represents preferably any one of a hydrogen atom or Group J of substituents, and at least one of X$_1$, X$_3$ and X$_s$ preferably represents an electron-withdrawing group having a Hammett's σp value of 0.3 or more. The electron-withdrawing group has an upper limit of the σp value of the Hammett's substituent constant of 1.0 or less.

If at least one of X$_1$, X$_3$ and X$_5$ is the electron-withdrawing group having a σp value in the aforementioned range, it is possible to adjust a color of the azo compound and improve light fastness and ozone gas fastness, thus being useful to a water-soluble dye for inkjet recording black ink.

Specific examples of the electron-withdrawing group having a σp value of 0.3 or more may include an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanate group, a thiocarbonyl group, a halogenated alkyl group, a halogenated alkoxy group, a halogenated aryloxy group, a halogenated alkylamino group, a halogenated alkylthio group, or an aryl group, a nitro group, a heterocyclic group, a halogen atom, an azo group or a cellenocyanate group substituted by another electron-withdrawing group having a σp value of 0.3 or more. The electron-withdrawing group is preferably a cyano group, a methylsulfonyl group, a phenylsulfonyl group, a methoxycarbonyl group, a carbamoyl group, or a nitro group, and more preferably a cyano group, a methylsulfonyl group, or a nitro group.

From the viewpoints of the hue, tinctorial strength, and storage stability of water solubility, among the aforementioned matters, at least one of X$_2$ and X$_4$ is preferably an ionic hydrophilic group, it is preferred that X$_1$, X$_3$ and X$_5$ are a hydrogen atom or an electron-withdrawing group having a Hammett's σp value of 0.3 or more, and it is more preferred that X$_1$, X$_3$ and X$_5$ are a hydrogen atom and X$_2$ and X$_4$ are an ionic hydrophilic group. The ionic hydrophilic group is preferably —SO$_3$M$_1$ or —CO$_2$M$_1$ (M$_1$ represents a hydrogen atom or a monovalent countercation), more preferably —CO$_2$M$_1$, and particularly preferably —CO$_2$Li.

A particularly preferred combination as the compound represented by Formula (3-2) includes the following (A) to (D).

(A) At least one of X$_2$ and X$_4$ is preferably an ionic hydrophilic group, it is preferred that X$_1$, X$_3$ and X$_5$ are a hydrogen atom or an electron-withdrawing group having a Hammett's σp value of 0.3 or more, and it is more preferred that X$_1$, X$_3$ and X$_5$ are a hydrogen atom and X$_2$ and X$_4$ are an ionic hydrophilic group.

(B) The monovalent substituent represented by R$_3$ may be exemplified by Group A' of substituents, and is preferably a substituted or unsubstituted alkyl group, a substituted or unsubstituted aryl group, or a heterocyclic group, and more preferably an alkyl group or an aryl group substituted by an ionic hydrophilic group.

(C) The ionic hydrophilic group is preferably —SO$_3$M$_1$ or —CO$_2$M$_1$ more preferably —CO$_2$M$_1$, and particularly preferably —CO$_2$Li.

(D) M$_1$ and M each independently represents a hydrogen atom or a monovalent countercation, and the monovalent countercation may be, for example, an ammonium ion, an alkali metal ion (e.g., a lithium ion, a sodium ion and a potassium ion), or an organic cation (e.g., a tetramethylammonium ion, a tetramethylguanidium ion or a tetramethylphosphonium), is preferably a lithium salt, a sodium salt, a potassium salt, or an ammonium salt, more preferably a lithium salt or a mixture salt including the lithium salt as a main component, and most preferably a lithium salt.

The preferred factors of this structure may be exemplified by the fact that the water solubility of the azo compound of Formula (3-2) and association property of the azo colorant are remarkably enhanced, and particularly storage stability in an aqueous solution is improved.

As a result, the storage stability as an aqueous solution is enhanced, and the light fastness, the heat stability, the moist heat stability, the water resistance, the gas resistance and/or the solvent resistance are considerably enhanced, and thus, this is a preferred example.

It is preferred that the compound represented by Formula (1), (2-2), or (3-2) is a compound represented by the following Formula (4-2).

Hereinafter, the compound represented by Formula (4-2) or a salt thereof will be described in detail.

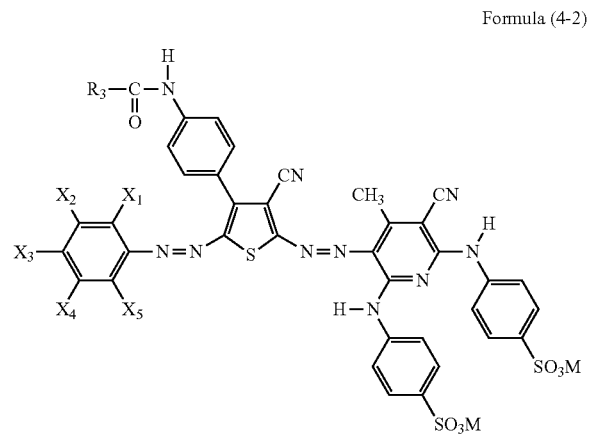

Formula (4-2)

(In Formula (4-2), $R_3$ represents a monovalent substituent. $X_1, X_2, X_3, X_4$ and $X_5$ each independently represents a hydrogen atom or a monovalent substituent. M each independently represents a hydrogen atom or a monovalent countercation.)

Examples of $R_3$ and M in Formula (4-2) each independently have the same meaning as examples of $R_3$ and M in Formula (2-2), and preferred examples thereof are also the same.

Examples of $X_1, X_2, X_3, X_4$ and $X_5$ in Formula (4-2) have the same meaning as examples of $X_1, X_2, X_3, X_4$ and $X_5$ in Formula (3-2), and preferred examples thereof are also the same.

A particularly preferred combination as the compound represented by Formula (4-2) includes the following (A) to (D).

(A) In Formula (1), A is an aryl group having a substituent, more preferably an aryl group having an ionic hydrophilic group or an electron-withdrawing group having a Hammett's σp value of 0.3 or more, and still more preferably a phenyl group having two ionic hydrophilic groups.

(B) The monovalent substituent represented by $R_3$ may be exemplified by Group A' of substituents, and is preferably a substituted or unsubstituted alkyl group, a substituted or unsubstituted aryl group, or a heterocyclic group, more preferably an alkyl group or an aryl group substituted by an ionic hydrophilic group, and particularly preferably an alkyl group substituted by an ionic hydrophilic group (a methyl group, an ethyl group or a n-propyl group is preferred, and a n-propyl group is particularly preferred).

(C) The ionic hydrophilic group is preferably —$SO_3M$ or —$CO_2M_1$, more preferably —$CO_2M_1$, and particularly preferably —$CO_2Li$.

(D) $M_1$ and M each independently represents a hydrogen atom or a monovalent countercation, and the monovalent countercation may be, for example, an ammonium ion, an alkali metal ion (e.g., a lithium ion, a sodium ion and a potassium ion), or an organic cation (e.g., a tetramethylammonium ion, a tetramethylguanidium ion or a tetramethylphosphonium). The formed salt is preferably a lithium salt, a sodium salt, a potassium salt, or an ammonium salt, more preferably a lithium salt or a mixture salt including a lithium salt as a main component, and most preferably a lithium salt.

The preferred point of the structure is that a ring including G in Formula (1) is not a nitrogen-containing 5-membered heterocyclic ring but a thiophene ring, a preservation property of image fastness of a printed matter using the ink composition of the present invention (for example, ozone gas fastness and light fastness) may be improved, and discoloration (a change in color) and decolorization (color fading) may be prevented at a higher level, and a suitability to grey to black ink requiring a small change in discoloration and decolorization is improved.

It is preferred that the compound represented by Formula (1), (2-2), (3-2), or (4-2) is a compound represented by the following Formula (5-2).

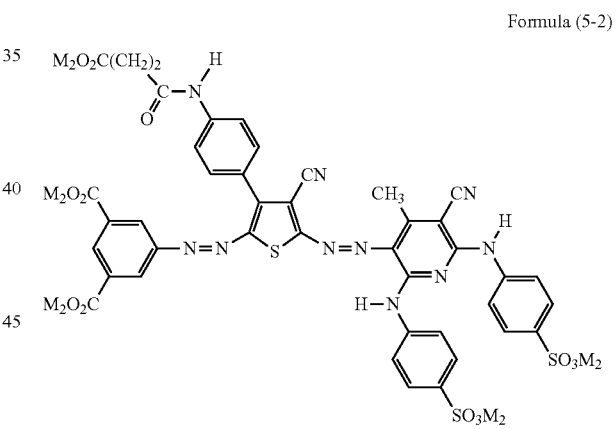

Formula (5-2)

($M_2$ each independently represents a hydrogen atom or a monovalent countercation, and in the case where $M_2$ represents a monovalent countercation, $M_2$ represents a lithium ion, a sodium ion, a potassium ion or an ammonium ion.)

Examples of $M_2$ in Formula (5-2) each independently have the same meaning as examples of M in Formula (2-2), and preferred examples thereof are also the same.

Further, the present invention relates to the azo compound represented by Formula (1), and the aqueous solution and the water-soluble ink composition using the azo compound of the present invention as a colorant mean a composition containing a coloring material such as a dye or a pigment and a dispersant thereof (solvent and the like), and particularly, may be suitably used to form an image.

Formula (1)

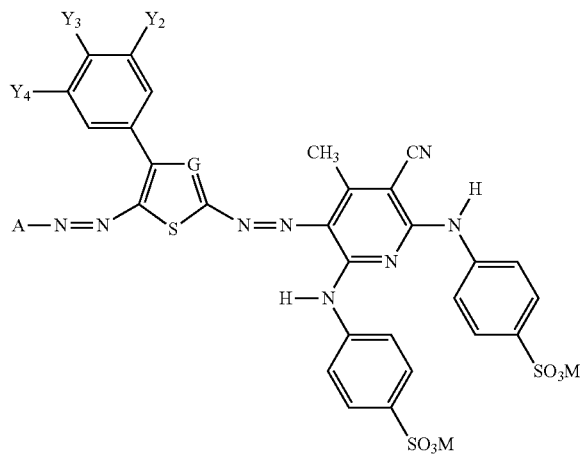

(In Formula (1), A represents a substituted phenyl group or a substituted or unsubstituted nitrogen-containing 5-membered heterocyclic group. G represents a nitrogen atom or —C($R_2$)=. $R_2$ represents a hydrogen atom, a sulfo group, a carboxy group, a substituted or unsubstituted carbamoyl group or cyano group. $Y_2$, $Y_3$ and $Y_4$ each independently represents a hydrogen atom or a monovalent substituent. $Y_2$, $Y_3$ and $Y_4$ may be bonded to each other to form a ring. All of $Y_2$, $Y_3$ and $Y_4$ do not represent a hydrogen atom at the same time. M each independently represents a hydrogen atom or a monovalent countercation.)

Examples of G, A, $R_2$, $Y_2$, $Y_3$, $Y_4$ and M in Formula (1) each independently have the same meaning as the examples of G, A, $R_2$, $Y_2$, $Y_3$, $Y_4$ and M in Formula (1), and preferred examples thereof are also the same.

It is preferred that the azo compound represented by Formula (1) is an azo compound represented by the following Formula (3-1).

Formula (3-1)

(In Formula (3-1), G represents a nitrogen atom or —C($R_2$)=. $R_2$ represents a hydrogen atom, a sulfo group, a carboxy group, a substituted or unsubstituted carbamoyl group or cyano group. $R_{11}$, $R_{12}$, $R_{13}$ and $R_{14}$ each independently represents a hydrogen atom or a monovalent substituent. $X_2$, $X_3$, $X_4$ and $X_5$ each independently represents a hydrogen atom or a monovalent substituent. M each independently represents a hydrogen atom or a monovalent countercation.)

Examples of G, $R_2$, $R_{11}$, $R_{12}$, $R_{13}$, $R_{14}$, $X_1$, $X_2$, $X_3$, $X_4$, $X_5$ and M in Formula (3-1) each independently have the same meaning as the examples of G, $R_2$, $R_{11}$, $R_{12}$, $R_{13}$, $R_{14}$, $X_1$, $X_2$, $X_3$, $X_4$, $X_5$ and M in Formula (3-1), and preferred examples thereof are also the same.

It is preferred that the azo compound represented by Formula (3-1) is an azo compound represented by the following Formula (4-1).

Formula (4-1)

(In Formula (4-1), $R_{11}$, $R_{12}$, $R_{13}$ and $R_{14}$ each independently represents a hydrogen atom or a monovalent substituent. $X_1$, $X_2$, $X_3$, $X_4$ and $X_5$ each independently represents a hydrogen atom or a monovalent substituent. M each independently represents a hydrogen atom or a monovalent countercation.)

Examples of $R_{11}$, $R_{12}$, $R_{13}$, $R_{14}$, $X_1$, $X_2$, $X_3$, $X_4$, $X_5$ and M in Formula (4-1) each independently have the same meaning as examples of $R_{11}$, $R_{12}$, $R_{13}$, $R_{14}$, $X_1$, $X_2$, $X_3$, $X_4$, $X_5$ and M in Formula (4-1), and preferred examples thereof are also the same.

It is preferred that the azo compound represented by Formula (4-1) is an azo compound represented by the following Formula (5).

Formula (5)

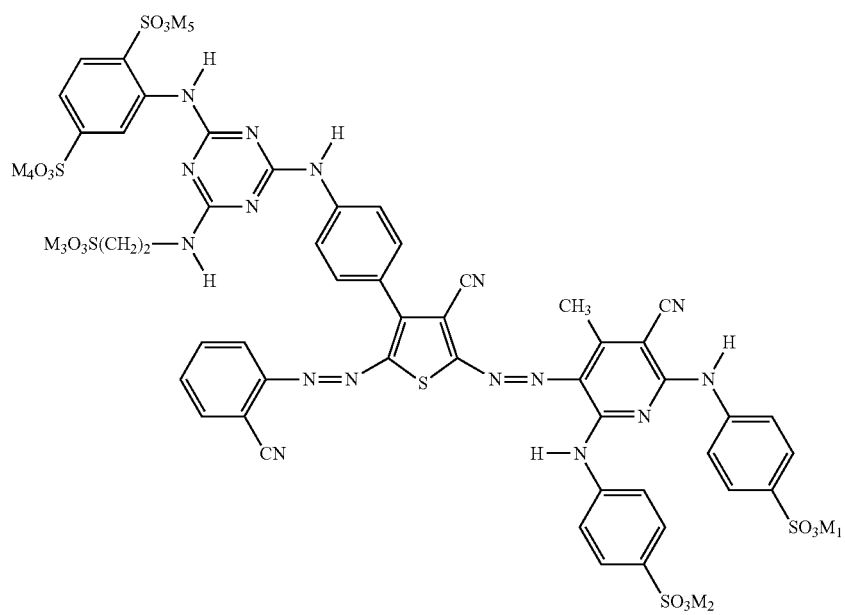

(In Formula (5), $M_1$, $M_2$, $M_3$, $M_4$ and $M_5$ each independently represents a hydrogen atom or a monovalent countercation, and in the case where $M_1$, $M_2$, $M_3$, $M_4$ and $M_5$ represent the monovalent countercation, $M_1$, $M_2$, $M_3$, $M_4$ and $M_5$ represent a lithium ion, a sodium ion, a potassium ion or an ammonium ion.)

It is preferred that the azo compound represented by Formula (1) is an azo compound represented by the following Formula (6).

Formula (6)

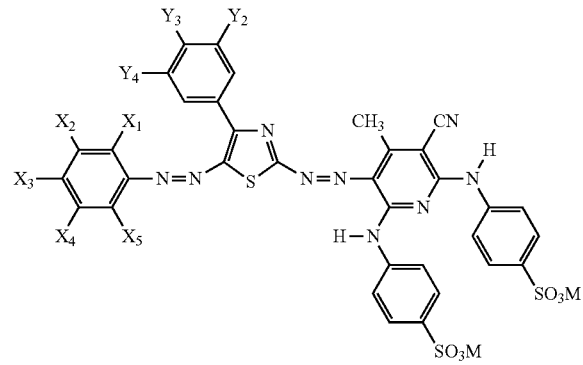

(In Formula (6), $X_1$, $X_2$, $X_3$, $X_4$ and $X_5$ each independently represents a hydrogen atom or a monovalent substituent. $Y_2$, $Y_3$ and $Y_4$ each independently represents a hydrogen atom or a monovalent substituent. M each independently represents a hydrogen atom or a monovalent countercation.)

Examples of $X_1$, $X_2$, $X_3$, $X_4$, $X_5$ and M in Formula (6) each independently have the same meaning as examples of $X_1$, $X_2$, $X_3$, $X_4$, $X_5$ and M in Formula (3-1), and preferred examples thereof are also the same.

Examples of $Y_2$, $Y_3$ and $Y_4$ in Formula (6) each independently have the same meaning as the examples of $Y_2$, $Y_3$ and $Y_4$ in Formula (1), and preferred examples thereof are also the same.

It is preferred that the azo compound represented by Formula (1) is an azo compound represented by the following Formula (7).

Formula (7)

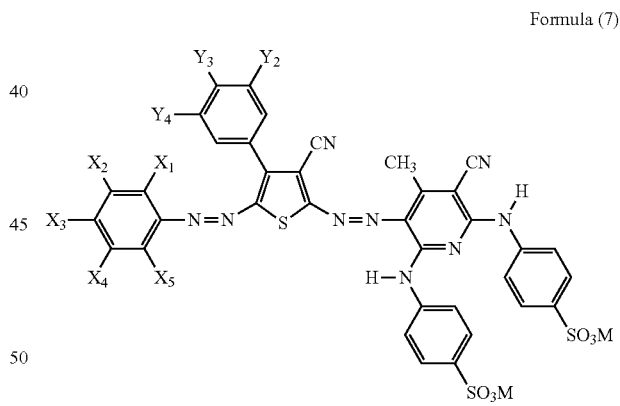

(In Formula (7), $X_1$, $X_2$, $X_3$, $X_4$ and $X_5$ each independently represents a hydrogen atom or a monovalent substituent. $Y_2$, $Y_3$ and $Y_4$ each independently represents a hydrogen atom or a monovalent substituent. M each independently represents a hydrogen atom or a monovalent countercation.)

Examples of $Y_2$, $Y_3$, $Y_4$, $X_1$ to $X_5$ and M in Formula (7) each independently have the same meaning as the examples of $Y_2$, $Y_3$, $Y_4$, $X_1$ to $X_5$ and M in Formula (6), and preferred examples thereof are also the same.

It is preferred that the azo compound represented by Formula (1) and (7) is an azo compound represented by the following Formula (8).

Formula (8)

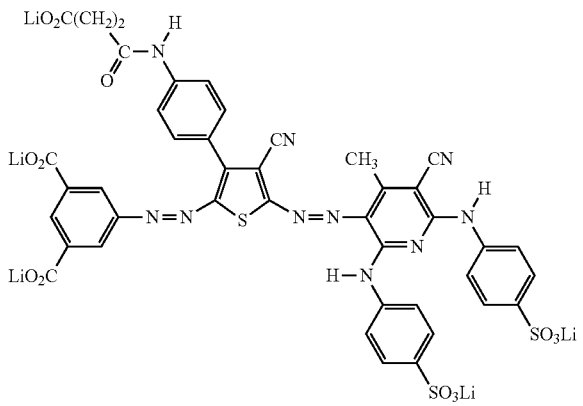

In the compound represented by Formulas (1), (2-1), (2-2), (3-1), (3-2), (4-1), (4-2), and (5) to (7), and Formula (8), a maximum absorption wavelength (λmax) of an absorption spectrum measured by using water as the solvent is preferably 550 nm or more and 700 nm or less, and particularly preferably 580 nm to 650 nm.

Further, in the present invention, it is preferred that the compound represented by Formulas (1), (2-1), (2-2), (3-1), (3-2), (4-1), (4-2), and (5) to (7), and Formula (8) have at least three or more ionic hydrophilic groups. The compound has more preferably 3 to 6 ionic hydrophilic groups, and still more preferably 4 to 5 ionic hydrophilic groups. Accordingly, the water solubility of the azo compound and the preservation stability of the aqueous solution of the present invention are improved, performance required as the water-soluble dye for inkjet recording black ink is satisfied at a high level, and there is an effect that an image quality of inkjet printed matter is further improved when the compound is used as ink for inkjet recording.

In the azo compound represented by Formulas (1), (2-1), (2-2), (3-1), (3-2), (4-1), (4-2), and (5) to (7), and Formula (8), it is preferred that at least one M is a lithium ion.

Further, in the present invention, even though the compound represented by Formulas (1), (2-1), (2-2), (3-1), (3-2), (4-1), (4-2) and (5) to (7), and Formula (8) includes isotope elements (for example, 2H, 3H, 13C, and 15N), the compound may be applied.

Hereinafter, specific examples of the compounds represented by Formulas (1), (2-1), (2-2), (3-1), (3-2), (4-1), (4-2), and (5) to (7), and Formula (8) will be described, but the compound used in the present invention is not limited to the following examples. M represents a hydrogen atom or a monovalent countercation (a lithium ion, a sodium ion, a potassium ion or an ammonium ion).

(BLACK-1)

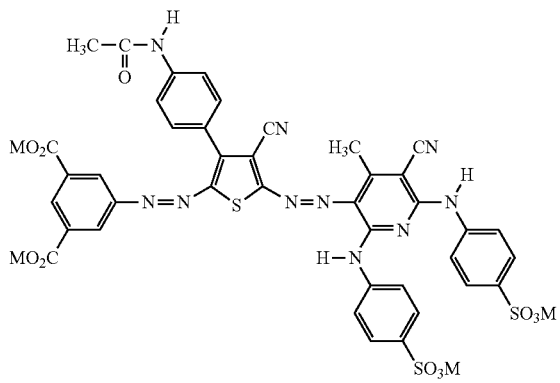

(BLACK-2)

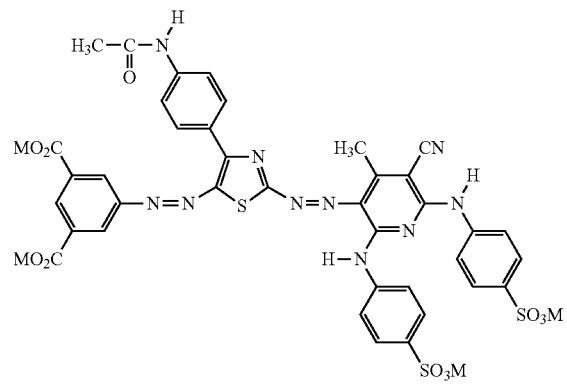

(BLACK-3)

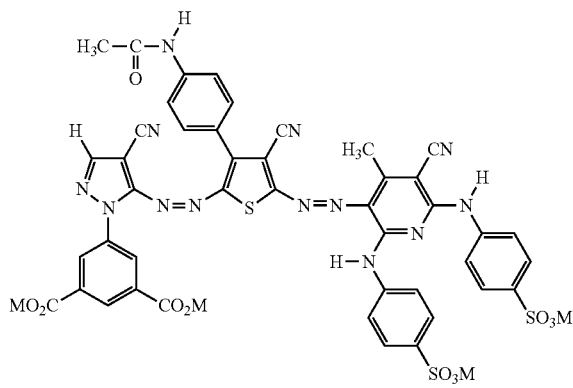

(BLACK-4)

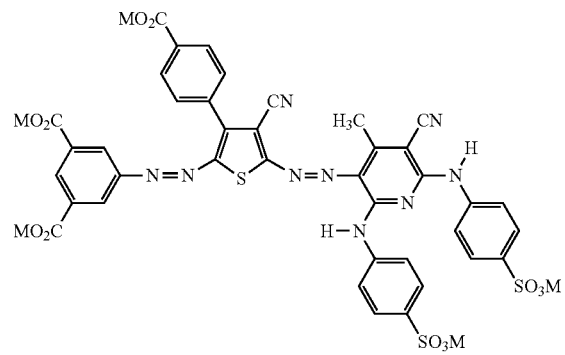

-continued
(BLACK-5)
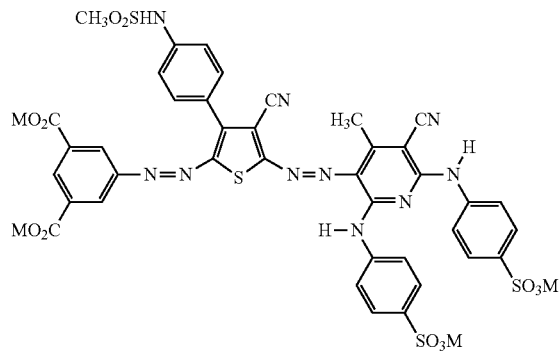
(BLACK-6)
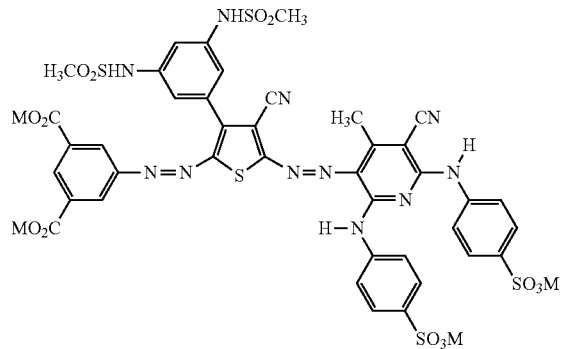
(BLACK-7)
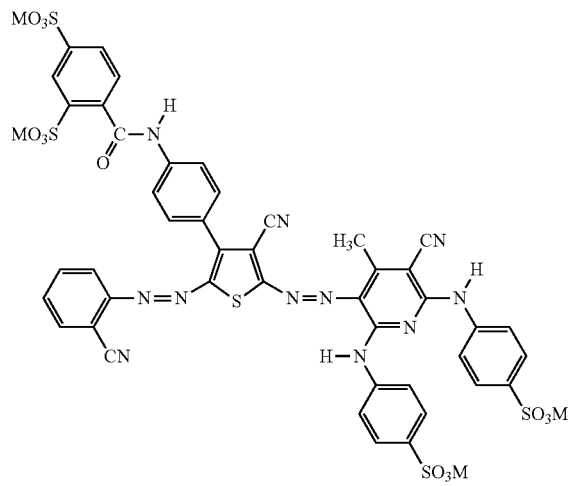
(BLACK-8)
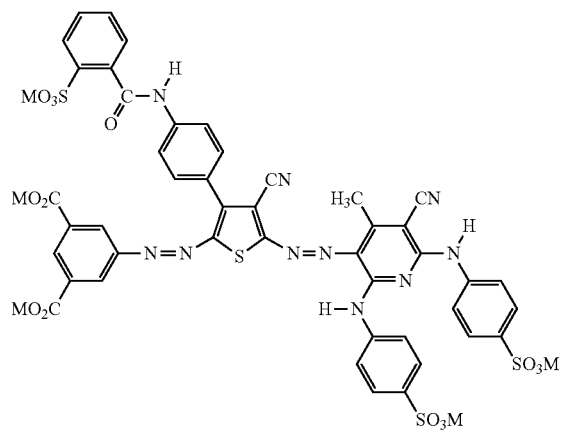
(BLACK-9)
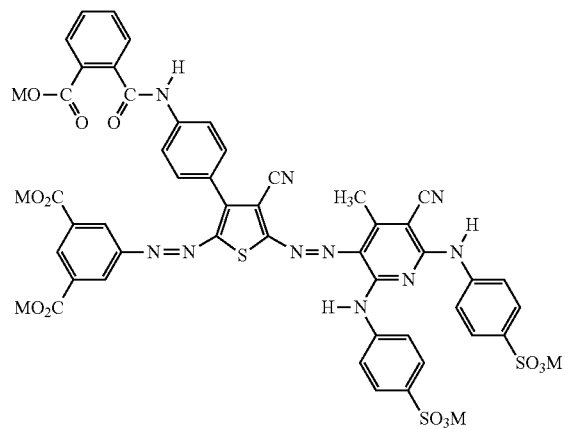
(BLACK-10)
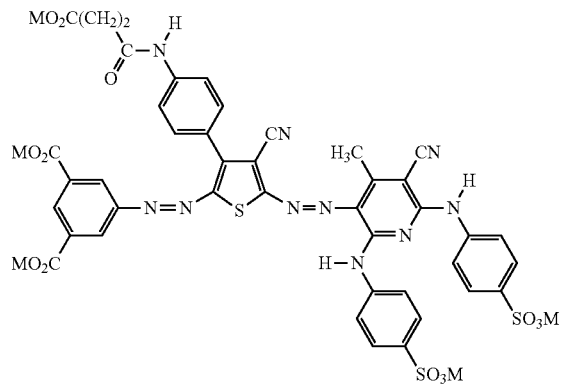

(BLACK-11)
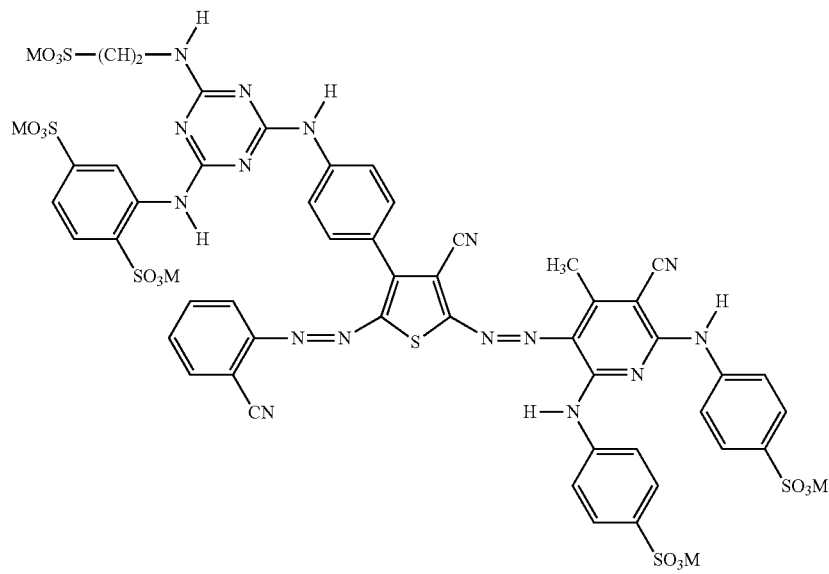
(BLACK-12)
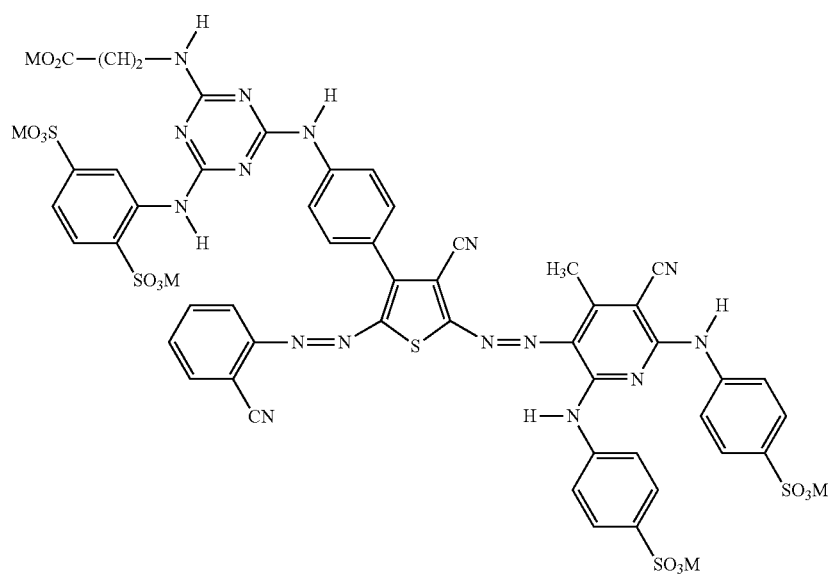
(BLACK-20)
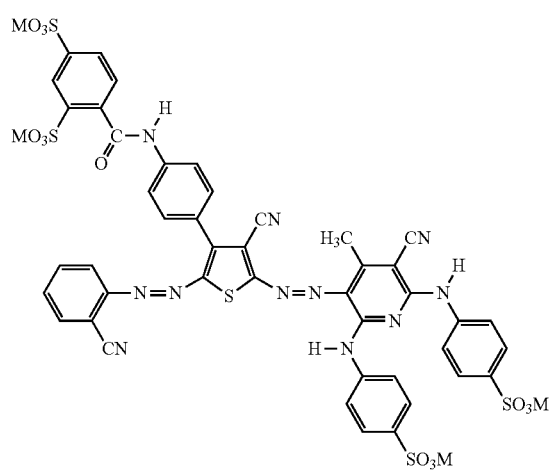
(BLACK-21)
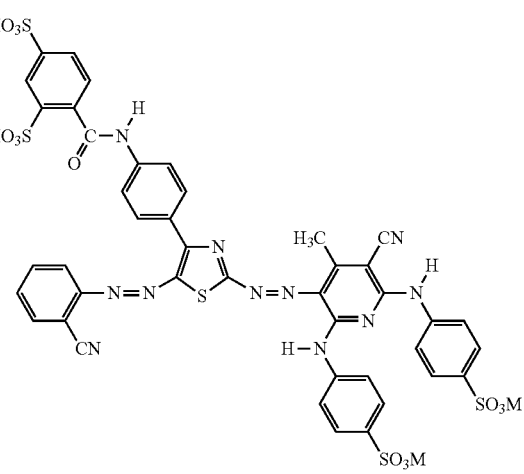

-continued (BLACK-22)

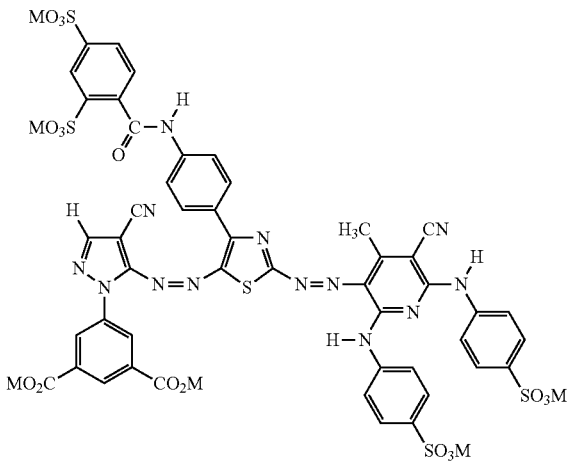

(BLACK-23)

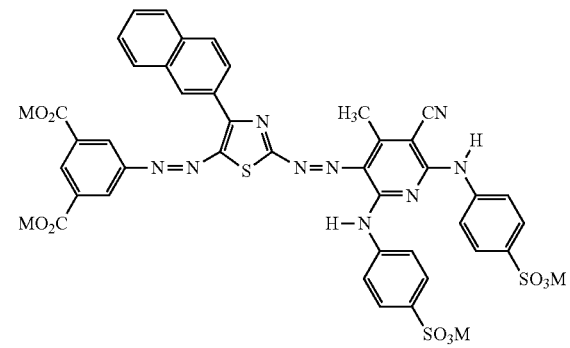

(BLACK-24)

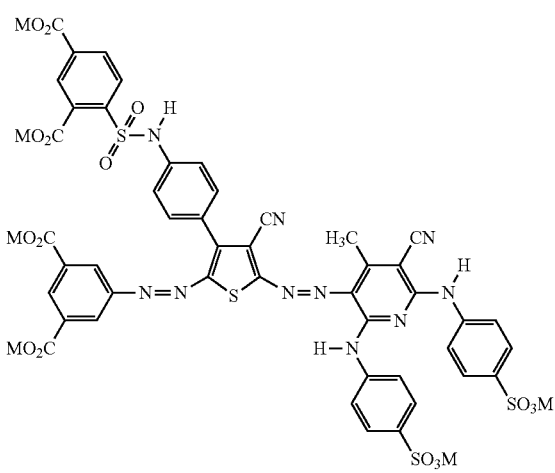

(BLACK-51)

(BLACK-52)

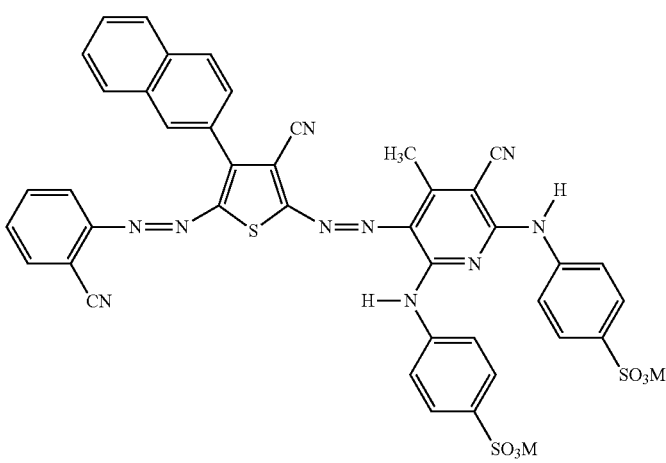

The azo compound represented by Formula (1) may be synthesized by a coupling reaction of a diazo component and a coupler, and is described in Japanese Patent Application Laid-Open No. 2003-306623 or Japanese Patent Application No. 2003-353498.

[(c) pH Adjusting Agent]

The aqueous solution of the present invention may further include (c) a pH adjusting agent.

A neutralizing agent (organic salt group, and inorganic alkali) may be used as the pH adjusting agent. It is preferred that the pH adjusting agent is added for the purpose of improving storage stability of ink for inkjet so that the pH of ink for inkjet is 7.0 to 9.0 at 25° C., and it is more preferred that the pH adjusting agent is added so that the pH is 7.5 to 8.5.

A desired pH may be obtained by setting the content of the pH adjusting agent to the aforementioned range.

Examples of the pH adjusting agent may include a basic matter such as an organic base and an inorganic base, and an acid matter such as an organic acid and an inorganic acid.

An inorganic compound such as sodium hydroxide, potassium hydroxide, lithium hydroxide, sodium carbonate, potassium carbonate, lithium carbonate, sodium hydrogen carbonate (sodium bicarbonate), potassium hydrogen carbonate, lithium hydrogen carbonate, sodium acetate, potassium acetate, sodium phosphate, and sodium phosphate monobasic, an organic base such as ammonia water, methylamine, ethylamine, diethylamine, triethylamine, ethanolamine, diethanolamine, triethanolamine, ethylenediamine, piperidine, diazabicyclooctane, diazabicycloundecene, pyridine, quinoline, pycoline, lutidine, and coridine, or an alkali metal salt of organic acid, such as lithium benzoate or potassium phthalate may be used as the basic compound.

An inorganic compound such as a hydrochloric acid, a sulfuric acid, a phosphoric acid, a boric acid, sodium hydrogen sulfate, potassium hydrogen sulfate, potassium dihydrogen phosphate, and sodium dihydrogen phosphate, or an organic compound such as acetic acid, tartaric acid, benzoic acid, trifluoroacetic acid, methanesulfonic acid, ethanesulfonic acid, benzenesulfonic acid, p-toluenesulfonic acid, saccharic acid, phthalic acid, picolinic acid, and quinolinic acid may be used as the acid compound.

The pH adjusting agent is preferably sodium hydrogen carbonate, potassium hydrogen carbonate, or lithium hydrogen carbonate, more preferably sodium hydrogen carbonate, or lithium hydrogen carbonate, and still more preferably lithium hydrogen carbonate.

Further, in the present invention, other colorants may be used together with the dye to perform adjustment for obtaining more preferred hue. A predetermined dye may be used as the dye used together. Examples of the yellow dye may include an aryl or heterylazo dye having heterocyclic rings such as substituted benzenes, substituted naphthalenes, pyrazolone, or pyridone, or chain-opening active methylene compounds as a coupling component (hereinafter, referred to as "coupler component"); an azomethine dye having a chain-opening active methylene compounds as the coupler component; a methine dye such as a benzylidene dye or a monomethineoxonol dye; or a quinone-based dye such as a naphthoquinone dye or an anthraquinone dye, and examples of the other dyes may include a quinophthalone dye, nitro and nitroso dyes, an acrydine dye, an acrydinone dye, or the like. Particularly, a dye S having the λmax of 350 nm to 500 nm is preferred to be used together, the aforementioned and following yellow dyes may be used, and among the dyes, an azo dye having 2 to 6 azo groups in one molecule is preferred. Meanwhile, in the present invention, a yellow pigment may be used.

Examples of the magenta dye may include an aryl or heterylazo dye having heterocyclic rings such as phenols, naphthols, anilines, pyridines, or pyrazines, or chain-opening active methylene compounds as the coupler component; an azomethine dye having a chain-opening active methylene compound as the coupler component; or an anthrapyridone dye. An azo dye or an anthrapyridone dye having a heterocyclic ring at a chromophore is particularly preferred.

Examples of the cyan dye may include an aryl or heterylazo dye having phenols, naphthols, anilines, or the like as the coupler component; an azomethine dye having heterocyclic rings such as phenols, naphthols, or pyrrolotriazoles as the coupler component; a polymethine dye such as a cyanine dye, an oxonol dye, or a melocyanine dye; a carbonium dye such as a diphenylmethane dye, a triphenylmethane dye, or a xanthene dye; a phthalocyanine dye; an anthraquinone dye; indigo and thioindigo dyes, or the like. The phthalocyanine dye is particularly preferred.

Because of a balance of fastness, a dye having an oxidation potential that is larger than 1.0 V or a dye having an association property is particularly preferred. Specific examples of the preferred dye used together may include a dye described in Japanese Patent Application Laid-Open No. 2003-360370.

In addition to the black dye, a known yellow dye and magenta dye may be used as the heterocyclic azo dye. The yellow dye and the magenta dye that are the heterocyclic azo dye have preferably at least one of the aforementioned properties (oxidation potential, and association property), and more preferably all properties. The oxidation potential of the dyes is larger than more preferably 1.1 V (vs SCE), and particularly preferably 1.15 V (vs SCE).

Examples of the yellow dye that is the heterocyclic azo dye may include matters described in Japanese Patent Application Laid-Open Nos. 2004-83903 (Paragraph Nos. [0048] to [0062]), 2003-277661 (Paragraph Nos. [0041] to [0050]), and 2003-277662 (Paragraph Nos. [0042] to [0047]), and US Patent Application Laid-Open No. US 2003/0213405 (Paragraph No. [0108]).

It is preferred that, in the case where the dye is water-soluble, the aqueous solution of the present invention is prepared by dissolution in an aqueous medium, and in the case where the dye is oil-soluble, the aqueous solution is prepared by dissolution and/or dispersion in an oleophilic medium and/or aqueous medium. The aqueous medium is a solvent including water as a main component, and includes an organic solvent such as a water-miscible organic solvent if necessary. The organic solvent may have a function as a viscosity reducing agent. The oleophilic medium includes an organic solvent as a main component.

The purpose of the aqueous solution of the present invention is not particularly limited, but preferably used for inkjet.

[Ink Composition]

The ink composition of the present invention includes the aqueous solution.

The content of the compound represented by Formula (1) in the ink composition is preferably 0.2% by mass to 20% by mass, more preferably 0.5% by mass to 10% by mass, and particularly preferably 1.0% by mass to 8.0% by mass.

The ink composition of the present invention includes the entire dye in a content of preferably 0.2% by mass to 20% by mass, more preferably 0.5% by mass to 10% by mass, and particularly preferably 1.0% by mass to 8.0% by mass.

The pH of the ink composition of the present invention at 25° C. is adjusted by the pH adjusting agent to preferably 7.0 to 10.0, and more preferably 7.5 to 9.5. In the case where the pH is 7.5 or more, the solubility of the dye may be improved to prevent a nozzle from being clogged. Further, if the pH is 9.5 or less, storage stability of ink over a long period of time is apt to be excellent.

The pH adjusting agent used in the ink composition may be exemplified by a matter used in the aqueous solution of the present invention, and is preferably lithium hydrogen carbonate, sodium hydrogen carbonate, or potassium hydrogen carbonate, and more preferably lithium hydrogen carbonate, or sodium hydrogen carbonate.

The purpose of the ink composition of the present invention is not particularly limited, and may be preferably used to prepare an ink composition for printing such as inkjet, an ink sheet in a thermosensitive recorded material, a color toner for an electronic dictionary, a color filter used in a display such as LCD or PDP or an imaging element such as CCD, a dyeing solution for dyeing various kinds of fibers, or the like, and an ink composition for inkjet recording is particularly preferred.

The method of preparing the ink composition may adopt the aqueous solution.

Black ink is suitable as the ink composition, but the ink composition is not limited to black ink, and may include a predetermined color of ink by mixing with another dye or pigment.

The method of preparing the ink composition includes a process of preparing a desired ink composition having the aforementioned range of viscosity by using at least the aqueous solution (hereinafter, referred to as "solution preparing process").

The solution preparing process is a process of preparing the ink composition for the desired purpose, including the aqueous solution obtained as described above having a predetermined viscosity, and the composition may be a final product or an intermediate product. The solution preparing process includes at least a process of diluting the aqueous solution by a medium, and preferably an aqueous medium. The aqueous solution including the oil-soluble dye is not particularly limited to the medium used in the dilution process, but is preferably emulsified and dispersed in the aqueous medium to be prepared as the aqueous ink composition. Various kinds of components may be included in the medium at a required concentration, the components may be separately added to the aqueous solution, and both may be combined.

Since the ink composition manufactured by the present invention is manufactured by using the aqueous solution where the concentration of the dye is high, solubility of the dye is improved as compared to the ink composition manufactured by a general method, and thus discharging stability is improved.

When the aqueous solution is manufactured, it is preferred that a process of removing dust, which is a solid by filtration, (filtering process) is added. In this work, a filter is used, and in this case, the filter having an effective diameter of 1 μm or less, and preferably 0.3 μm or less is used. Various matters may be used as the material of the filter, and particularly, in the case of the aqueous solution of the water-soluble dye, it is preferred to use the filter manufactured for the purpose of an aqueous solvent. Among the filters, it is particularly preferred to use a jacket type filter manufactured by using a polymer material, from which the dust is difficult to be generated. In a filtering method, a transport solution may pass through a jacket, and any one method of pressure filtration and vacuum filtration may be used.

In the present invention, a viscosity reducing agent may be used, and filtration treatment may be performed without resistance.

In the process of preparing the aqueous solution or the solution preparing process, various methods such as dissolution by stirring, dissolution by radiation of an ultrasonic wave, and dissolution by shaking may be used as a method of dissolving the dye or other components. Among the methods, the stirring method is particularly preferably used. In the case where the stirring is performed, various methods known in the art, such as fluidization stirring and stirring using shearing stress using an inversion agitator or a dissolver, may be used. Meanwhile, an stirring method using shearing stress to a vessel bottom surface like a magnetic agitator may be preferably used.

Subsequently, the dye used in the aqueous solution and the ink composition of the present invention will be described. The dye is not particularly limited, but it is preferred that the dye includes at least one azo compound represented by Formula (1) and having λmax of 500 nm to 700 nm and full width at half maximum (Wλ, ½) of 100 nm or more, preferably 120 nm or more and 500 nm or less, and more preferably 120 nm or more and 350 nm or less in an absorption spectrum of a diluted solution regulated to have absorbance of 1.0.

In the case where the azo compound represented by Formula (1) alone implements black where any color tone of B, G, and R is difficult to be emphasized regardless of an observation light source of "(good forming) black" having high image quality, it is possible to use the dye alone as a raw material of the aqueous solution or the ink composition, but a dye covering a region at which absorption of the dye is insignificant is generally used together therewith as a common ink composition. Generally, in the case of the ink composition using the azo compound represented by Formula (1), it is preferred that the ink composition be used together with another dye having main absorption (λmax is 350 nm to 500 nm) at a yellow region. Further, the ink composition can be manufactured together with yet another dye.

The other dye may be used in the aqueous solution, but is preferably used while being mixed with the ink composition when the ink composition is prepared from the viewpoint of storage stability.

In the present invention, the black ink composition satisfying the following conditions is preferred in order to satisfy requirements that 1) weather resistance is excellent and/or 2) a balance of black is not lost after discoloration.

First, a black rectangular sign of JIS code 2223 is printed as 48 points by using the black ink composition, and a reflection concentration ($D_{vis}$) obtained by measuring the sign by a status A filter (visual filter) is regulated as an initial concentration. Examples of a reflection concentration measuring device on which the status A filter is mounted may include an X-Rite concentration measuring device, and the like. Herein, in the case where the concentration of "black" is measured, the measured value by $D_{vis}$, as a standard observed reflection concentration is used. The printed matter is forcibly discolored by using an ozone discoloration test device always generating ozone at 5 ppm, and a forcible discoloration speed constant ($k_{vis}$) at a time (t) until the reflection concentration ($D_{vis}$) is 80% of an initial reflection concentration value is obtained from a relationship equation of "$0.8=\exp(-k_{vis} \cdot t)$".

In the present invention, the ink composition is manufactured so that the speed constant ($k_{vis}$) is $5.0 \times 10^{-2}$ [hour$^{-1}$] or less, preferably $3.0 \times 10^{-2}$ [hour$^{-1}$] or less, and more preferably $1.0 \times 10^{-2}$ [hour$^{-1}$] or less.

Further, the black rectangular sign of JIS code 2223 is printed as 48 points by using the black ink composition, and is defined as a concentration measured value measured by the status A filter, and reflection concentrations ($D_R$, $D_G$, $D_B$) of three colors of C (cyan), M (magenta), and Y (yellow) that are not $D_{vis}$, are regulated as the initial concentration. Herein, $D_R$, $D_G$, and $D_B$ represent a C reflection concentration by a red filter, an M reflection concentration by a green filter, and a Y reflection concentration by a blue filter. The printed matter is forcibly discolored by using the ozone discoloration test device always generating ozone at 5 ppm according to the aforementioned method, and the forcible discoloration speed constants ($k_R$, $k_G$, and $k_B$) at a time (t) until the reflection concentrations ($D_R$, $D_G$, and $D_B$) are 80% of an initial concentration value are determined similarly. In the case where a ratio (R) of maximum and minimum values is obtained by obtaining the three speed constants (for example, in the case where $k_R$ is the maximum value and the $k_G$ is the minimum value, $R=k_R/k_G$), the ink composition where the ratio (R) is 1.2 or less, preferably 1.1 or less, and more preferably 1.05 or less is produced.

Meanwhile, the used "printed matter obtained by printing the black rectangular sign of JIS code 2223 as 48 points" is obtained by printing an image having a size enough to cover an opening of a measuring device in order to provide the size enough to measure the concentration.

Further, as the aqueous solution of the present invention, in detail, the dye used in the ink composition, a dye where the azo group is bonded to the heterocyclic ring (hereinafter, referred to as "a heterocyclic azo dye") and an phthalocyanine dye having an association property (hereinafter, all the dyes used in the present invention, such as the heterocyclic azo dye and the phthalocyanine dye are referred to as the dye for the present invention) are preferred. It is preferred that the present invention includes at least one kind of the heterocyclic azo dye or the phthalocyanine dye, and other dyes and/or pigments may be used in combination therewith.

Further, it is preferred that the dye used in the present invention has the oxidation potential of 1.0 V (vs SCE) or more.

The oxidation potential value (Eox) may be easily measured by the person with ordinary skill in the art. This method is described in, for example, "New Instrumental Methods in Electrochemistry" (published by Interscience Publishers, Co., Ltd. in 1954) by P. Delahay, "Electrochemical Methods" (published by John Wiley & Sons, Co., Ltd. in 1980) by A. J. Bard, et al., or "Electrochemical Measurement Method" (published by GIHODO SHUPPAN Co., Ltd. in 1984) by Fujishima Akira, et al.

Specifically, the oxidation potential is measured as a value to SCE (saturated calomel electrode) by dissolving a subject sample in a concentration of $1\times10^{-2}$ mole/liter to $1\times10^{-6}$ mole/liter in a solvent, such as dimethylformamide or acetonitrile, including a support electrolyte such as sodium perchlorate or tetrapropylammonium perchlorate using various kinds of voltammetries (a method using polarography using a dropping mercury electrode, a cyclic voltammetry, and a rotation disk electrode, and the like). This value may be deflected by about several tens of milli volts due to effects such as a potential difference between solutions or solution resistance of the sample solution, but reproducibility of the potential may be ensured by providing the standard sample (for example, hydroquinone).

Meanwhile, in the present invention, the value (vs SCE) measured by using SCE (saturated calomel electrode) as a reference electrode, a graphite electrode as an operation electrode, and a platinum electrode as a counter electrode in N,N-dimethylformamide (the concentration of the dye is 0.001 mol/liter) including 0.1 mol/liter of tetrapropylammonium perchlorate as the support electrolyte is set as the oxidation potential of the dye.

The Eox value means the degree of easiness of moving of electrons from the sample to the electrode, and means that it is difficult to move the electrons from the sample to the electrode, in other words, it is difficult to perform oxidation, as the value is increased (the oxidation potential is increased). With regard to the structure of the compound, the oxidation potential is increased by introducing the electron-withdrawing group, and the oxidation potential is reduced by introducing an electron-donating group. In the present invention, it is preferred to increase the oxidation potential by introducing the electron-withdrawing group to the dye skeleton in order to reduce reactivity to ozone that is an electrophile.

Further, in the following evaluation method of the association property, the dye used in the present invention has $\epsilon 1/\epsilon 2$ of preferably 1.1 or more, more preferably 1.1 to 1.5, and particularly preferably 1.2 to 1.5.

Evaluation Method of the Association Property of the Dye

The association property of the dye may be evaluated as described below. The ratio $\epsilon 1/\epsilon 2$ of the molar extinction coefficient ($\epsilon 1$) of the solution absorption spectrum when 0.01 mmol/L of the dye solution is measured by using the cell having an optical path length of 1 cm and the molar extinction coefficient ($\epsilon 2$) of the solution absorption spectrum when 20 mmol/L of the dye solution is measured by using the cell having the optical path length of 5 μm becomes an index of the association property of the dye. As the value is increased, the dye is easily associated. The dye having the value of 1.1 or more exhibits excellent performance of ozone resistance and light resistance by association of the dye.

As the solvent used in the dye solution, ultrapure water having a specific resistance value of 18 MΩ·cm or more, such as deionized water is used if the dye is water-soluble, and if the dye is oil-soluble, in the case where the solution is a homogeneous solution, an organic solvent in which the dye is soluble is used, or measurement is performed as a dispersant or an emulsion in ultrapure water like the case of the water-soluble dye.

Examples of the dye used in the present invention are as follows. The dye may be used alone, or a plurality of dyes may be used in combination in order to ensure a color tone. Further, the ink compositions obtained from yellow, magenta, cyan and black ink stock solutions of the present invention may be used to form a monochromic image or form an image of a full color. In order to form the full color image, the ink composition having two colors of light and shade to each color may be used. Moreover, the ink composition having a middle color tone such as red, green, blue and violet may be used. The ink composition of the present invention may constitute an ink set for obtaining the full color image. Alternately, the ink composition may constitute a portion of the ink set. That is, a predetermined ink composition other than the present invention and the ink composition of the present invention may be combined in order to constitute the ink set.

Further, in the ink composition of the present invention, different colorants for obtaining the color tone may be used together in order to obtain the full color image.

In the present invention, predetermined matters may be used as the colorant used in the ink set or the colorant used together with the dye. Examples of the dye used together therewith may include the aforementioned dyes and the following matters.

The yellow dye may be, for example, an aryl or heterylazo dye having phenols, naphthols, anilines, pyrazolons, pyridones, and chain-opening active methylene compounds as the coupling component; an azomethine dye having the chain-opening active methylene compounds as the coupling component; a methine dye such as a benzylidene dye or a monomethineoxonol dye; a quinine-based dye such as a naphthoquinone dye and an anthraquinone dye, or the like, and the other kind of dye may be a quinophthalon dye, nitro and nitroso dyes, an acrydin dye, an acrydinone dye, or the like. These dyes may be a matter where a portion of chromophore is dissociated to have yellow, and in this case, the countercation may be an inorganic cation such as alkali metal or ammonium, an organic cation such as pyridinium or quaternary ammonium salt, or a polymer cation having the aforementioned cations as a partial structure.

The magenta dye may be, for example, an aryl or heterylazo dye having phenols, naphthols, and anilines as the coupling component; an azomethine dye having pyrazolons and pyrazolotriazoles as the coupling component; a methine dye such as an arylidene dye, a styryl dye, a melocyanine dye, and an oxonol dye; a carbonium dye such as a diphenylmethane dye, a triphenylmethane dye, and a xanthene dye; a quinone-based dye such as naphthoquinone, anthraquinone, and anthrapyridone; or a condensed polycyclic ring-based colorant such as a dioxazine dye, or the like. These dyes may be a matter where a portion of chromophore is dissociated to have magenta, and in this case, the counteraction may be an inorganic cation such as alkali metal or ammonium, an organic cation such as pyridinium or quaternary ammonium salt, or a polymer cation having the aforementioned cations as a partial structure.

The cyan dye may be, for example, an azomethine dye such as an endoaniline dye and an endophenol dye; a polymethine dye such as a cyanine dye, an oxonol dye, and a melocyanine dye; a carbonium dye such as a diphenylmethane dye, a triphenylmethane dye, and a xanthene dye; a phthalocyanine dye; an anthraquinone dye; an aryl or heterylazo dye having phenols, naphthols, and anilines as the coupling component; or indigo and thioindigo dyes. These dyes may be a matter where a portion of chromophore is dissociated to have cyan, and in this case, the counteraction may be an inorganic cation such as alkali metal or ammonium, an organic cation such as pyridinium or quaternary ammonium salt, or a polymer cation having the aforementioned cations as a partial structure.

Further, a water-soluble dye such as a direct dye, an acidic dye, an edible dye, a basic dye, and a reactive dye may be used together. Among the dyes, preferred examples thereof may include C.I. Direct Red 1, 2, 4, 9, 11, 23, 26, 31, 37, 39, 62, 63, 72, 75, 76, 79, 80, 81, 83, 84, 87, 89, 92, 95, 111, 173, 184, 207, 211, 212, 214, 218, 21, 223, 224, 225, 226, 227, 232, 233, 240, 241, 242, 243, 247, 254, C.I. Direct Violet 7, 9, 47, 48, 51, 66, 90, 93, 94, 95, 98, 100, 101, C.I. Direct Yellow 4, 8, 9, 11, 12, 27, 28, 29, 33, 35, 39, 41, 44, 50, 53, 58, 59, 68, 86, 87, 93, 95, 96, 98, 100, 106, 108, 109, 110, 120, 130, 132, 142, 144, 157, 161, 163, C.I. Direct Blue 1, 10, 15, 22, 25, 55, 67, 68, 71, 76, 77, 78, 80, 84, 86, 87, 90, 98, 106, 108, 109, 151, 156, 158, 159, 160, 168, 189, 192, 193, 194, 199, 200, 201, 202, 203, 207, 211, 213, 214, 218, 225, 229, 236, 237, 244, 248, 249, 251, 252, 264, 270, 280, 288, 289, 290, 291, C.I. Direct Black 9, 17, 19, 22, 32, 51, 56, 62, 69, 77, 80, 91, 94, 97, 108, 112, 113, 114, 117, 118, 121, 122, 125, 132, 146, 154, 166, 168, 173, 199, C.I. Acid Red 1, 8, 35, 42, 52, 57, 62, 80, 81, 82, 87, 94, 111, 114, 115, 118, 119, 127, 128, 131, 143, 144, 151, 152, 154, 158, 186, 245, 249, 254, 257, 261, 263, 266, 289, 299, 301, 305, 336, 337, 361, 396, 397, C.I. Acid Violet 5, 34, 43, 47, 48, 90, 103, 126, C.I. Acid Yellow 17, 19, 23, 25, 39, 40, 42, 44, 49, 50, 61, 64, 76, 79, 110, 127, 135, 143, 151, 159, 169, 174, 190, 195, 196, 197, 199, 218, 219, 222, 227, C.I. Acid Blue 9, 25, 40, 41, 62, 72, 76, 78, 80, 82, 87, 92, 106, 112, 113, 120, 127:1, 129, 138, 143, 175, 181, 185, 205, 207, 220, 221, 230, 232, 247, 249, 258, 260, 264, 271, 277, 278, 279, 280, 288, 290, 326, C.I. Acid Black 7, 24, 29, 48, 52:1, 172, C.I. Reactive Red 3, 6, 13, 17, 19, 21, 22, 23, 24, 29, 35, 37, 40, 41, 43, 45, 49, 55, 63, 106, 107, 112, 113, 114, 126, 127, 128, 129, 130, 131, 137, 160, 161, 174, 180, C.I. Reactive Violet 1, 3, 4, 5, 6, 7, 8, 9, 16, 17, 22, 23, 24, 26, 27, 33, 34, C.I. Reactive Yellow 2, 3, 13, 14, 15, 17, 18, 23, 24, 25, 26, 27, 29, 35, 37, 41, 42, C.I. Reactive Blue 2, 3, 5, 7, 8, 10, 13, 14, 15, 17, 18, 19, 21, 25, 26, 27, 28, 29, 38, 82, 89, 158, 182, 190, 203, 216, 220, 244, C.I. Reactive Black 4, 5, 8, 14, 21, 23, 26, 31, 32, 34, C.I. Basic Red 12, 13, 14, 15, 18, 22, 23, 24, 25, 27, 29, 35, 36, 38, 39, 45, 46, C.I. Basic Violet 1, 2, 3, 7, 10, 15, 16, 20, 21, 25, 27, 28, 35, 37, 39, 40, 48, C.I. Basic Yellow 1, 2, 4, 11, 13, 14, 15, 19, 21, 23, 24, 25, 28, 29, 32, 36, 39, 40, C.I. Basic Blue 1, 3, 5, 7, 9, 22, 26, 41, 45, 46, 47, 54, 57, 60, 62, 65, 66, 69, 71, C.I. Basic Black 8, and the like.

In addition to the dye represented by the aforementioned equation, dyes described in the following official gazettes may be preferably used. Japanese Patent Application Laid-Open Nos. H10-130557, H9-255906, H6-234944, and 117-97541, EP 982371, WO 00/43450, WO 00/43451, WO 00/43452, WO 00/43453, WO 03/106572, WO 03/104332, Japanese Patent Application Laid-Open Nos. 2003-238862, 2004-83609, 2002-302619, 2002-327131, and 2002-265809, WO 01/48090, WO 04/087815, WO 02/90441, WO 03/027185, WO 04/085541, Japanese Patent Application Laid-Open Nos. 2003-321627, 2002-332418, and 2002-332419, WO 02/059215, WO 02/059216, WO 04/087814, WO 04/046252, WO 04/046265, U.S. Pat. No. 6,652,637, WO 03/106572, WO 03/104332, WO 00/58407, Japanese Patent Nos. 3558213, 3558212, and 3558211, and Japanese Patent Application Laid-Open No. 2004-285351, WO 04/078860, Japanese Patent Application Laid-Open No. 2004-323605, and WO 04/104108.

Moreover, in the present invention, the pigment may be used together with the dye.

As the pigment used in the present invention, known matters described in various kinds of documents may be used in addition to a commercial matter. With regard to the documents, there are Color Index (edited by The Society of Dyers and Colourists), "Revisely Edited Pigment Handbook" edited by Japanese Pigment Technology Association (published in 1989), "Current Pigment Applied Technology" CMC Publishing Co., Ltd. (published in 1986), "Printing Ink Technology" CMC Publishing Co., Ltd. (published in 1984), Industrial Organic Pigments (VCH Verlagsgesellschaft, published in 1993) written by W. Herbst and K. Hunger, and the like. Specifically, the organic pigment may be an azo pigment (an azo lake pigment, an insoluble azo pigment, a condensed azo pigment, and a chelate azo pigment), a polycyclic pigment (a phthalocyanine-based pigment, an anthraquinone-based pigment, perylene and perynone-based pigments, an indigo-based pigment, a quinacridone-based pigment, a dioxazine-based pigment, an isoindolinone-based pigment, a quinophthalon-based pigment, a diketopyrrolopyrrole-based pigment, or the like), a dyeing lake pigment (a lake pigment of an acidic or basic dye), an azine pigment, or the like, and the inorganic pigment may be C.I. Pigment Yellow 34, 37, 42, and 53 that are a yellow pigment, C.I. Pigment Red 101, and 108 that are a red-based pigment, C.I. Pigment Blue 27, 29, and 17:1 that are a blue-based pigment, C.I. Pigment Black 7 that is a black-based pigment, magnetite, C.I. Pigment White 4, 6, 18, and 21 that are a white-based pigment, or the like.

The pigment having a preferred color tone for forming an image is preferably a phthalocyanine pigment as a blue to cyan pigment, an anthraquinone-based indanthrone pigment (for example, C.I. Pigment Blue 60 and the like), or a triarylcarbonium pigment that is dyeing lake pigments, and particularly most preferably a phthalocyanine pigment (preferred examples are copper phthalocyanine such as C.I. Pigment Blue 15:1, 15:2, 15:3, 15:4, and 15:6, monochloro to low chlorinated copper phthalocyanine, the pigment described in EP 860475 as aluminiumphthalocyanine, non-metal phthalocyanine that is C.I. Pigment Blue 16, and phthalocyanine where central metal is Zn, Ni, or Ti, or the like, and among the pigments, C.I. Pigment Blue 15:3, and 15:4, and aluminiumphthalocyanine are preferred).

The red to purple pigment is an azo pigment (preferred examples are C.I. Pigment Red 3, 5, 11, 22, 38, 48:1, 48:2, 48:3, 48:4, 49:1, 52:1, 53:1, 57:1, 63:2, 144, 146, and 184) or the like, and among the pigments, C.I. Pigment Red 57:1, 146, and 184), a quinacrydone-based pigment (preferred examples are C.I. Pigment Red 122, 192, 202, 207, and 209, C.I. Pigment Violet 19, and 42, and among the examples, C.I. Pigment Red 122 is preferred), a dyeing lake pigment-based triarylcarbonium pigment (preferred examples are xanthene-based C.I. Pigment Red 81:1, C.I. Pigment Violet 1, 2, 3, 27, and 39), a dioxazine-based pigment (for example, C.I. Pigment Violet 23, and 37), a diketopyrrolopyrrole-based pigment (for example, C.I. Pigment Red 254), a perylene pigment (for example, C.I. Pigment Violet 29), an anthraquinone-based pigment (for example, C.I. Pigment Violet 5:1, 31, and 33), and thioindigos (for example, C.I. Pigment Red 38, and 88) are preferably used.

The yellow pigment is preferably an azo pigment (preferred examples are C.I. Pigment Yellow 1, 3, 74, and 98 that are a monoazo pigment system, C.I. Pigment Yellow 12, 13, 14, 16, 17, and 83 that are a disazo pigment system, C.I. Pigment Yellow 93, 94, 95, 128, and 155 that are a azo system, and C.I. Pigment Yellow 120, 151, 154, 156, and 180 that are a benzimidazolon system, and the like, and among the examples, a matter where a benzidine-based compound is not used in a raw material is preferred), isoindoline and isoindolinone-based pigments (preferred examples are C.I. Pigment Yellow 109, 110, 137, 139, and the like), a quinophthalon pigment (preferred examples are C.I. Pigment Yellow 138 and the like), or a flavanthrone pigment (for example, C.I. Pigment Yellow 24 and the like).

The black pigment may be preferably an inorganic pigment (preferably, for example, carbon black, and magnetite) or aniline black. Moreover, an orange pigment (C.I. Pigment Orange 13, 16 and the like) or a green pigment (C.I. Pigment Green 7 and the like) may be used.

The pigment used in the present invention may be the aforementioned basic (bare) pigment or a pigment that is subjected to surface treatment. The surface treatment method may be considered as a method of performing a surface coat to a resin or a wax, a method of attaching a surfactant, a method of bonding a reactive material (for example, radicals and the like formed in a silane coupling agent, an epoxy compound, polyisocyanate, or diazonium salt) to a pigment surface, or the like, and is described in the following documents or patent documents.

(1) Properties and Application of Metal Soap (Saiwaishobo)
(2) Printing of Print Ink (CMC Publishing Co., Ltd. 1984)
(3) Current Pigment Applied Technology (CMC Publishing Co., Ltd. 1986)
(4) U.S. Pat. Nos. 5,554,739 and 5,571,311
(5) Japanese Patent Application Laid-Open Nos. H9-151342, 10-140065, 10-292143, and 11-166145

Particularly, a magnetic dispersible pigment prepared by operating the diazonium salt described in the US patent of (4) to carbon black or a capsulated pigment prepared by a method described in the Japanese patent of (5) can obtain dispersion stability while a dispersant is not used in a required amount or more in the ink composition, which is particularly effective.

In the present invention, the pigment may be dispersed by using the dispersant. The dispersant may be various matters known to be adjusted to the used pigment, for example, a surfactant type low dispersion dispersant or a polymer type dispersant. Examples of the dispersant may include matters described in Japanese Patent Application Laid-Open No. H3-69949, EP 549486, and the like. Further, when the dispersant is used, a pigment derivative that is called a synergist may be added in order to promote adsorption of the dispersant to the pigment. The particle diameter of the pigment used in the present invention is in a range of preferably 0.01 μm to 10 μm and more preferably 0.05 μm to 1 μm after dispersion.

As a method of dispersing the pigment, a known dispersing technology used to manufacture ink or a toner may be used. A dispersing machine may be a longitudinal type or transversal type agitator mill, an attritor, a colloid mill, a ball mill, a 3-roll mill, a pearl mill, a super mill, an impeller, a disperser, a KD mill, a dynatron, a pressure kneader, and the like. Details are described in "Current Pigment Applied Technology" (CMC Publishing Co., Ltd. 1986).

The water-soluble dye used in the present invention is preferably dyes such as a magenta dye described in the official gazette of Japanese Patent Application Laid-Open No. 2002-371214, a phthalocyanine dye described in the official gazette of Japanese Patent Application Laid-Open No. 2002-309118, or water-soluble phthalocyanine dyes of the official gazettes of Japanese Patent Application Laid-Open Nos. 2003-12952 and 2003-12956.

The ink composition of the present invention includes the dye in a medium and preferably an aqueous medium. Water or water and a solvent such as a water-miscible organic solvent, if necessary, is added to the aqueous medium. Meanwhile, the water-miscible organic solvent may be a viscosity reducing agent in an ink stock solution like the above.

The water-miscible organic solvent used in the present invention is a material having functions such as a drying preventing agent, a permeation promoting agent, and a wetting agent in an ink composition for inkjet recording in the art, and a high boiling point water-miscible organic solvent is mainly used. The compound may be alcohol (for example, methanol, ethanol, propanol, isopropanol, butanol, isobutanol, sec-butanol, t-butanol, pentanol, hexanol, cyclohexanol or benzylalcohol), polyvalent alcohols (for example, ethylene glycol, diethylene glycol, triethylene glycol, polyethylene glycol, propylene glycol, dipropylene glycol, polypropylene glycol, butylene glycol, hexanediol, pentanediol, glycerine, hexanetriol or thiodi glycol), a glycol derivative (for example, ethylene glycol monomethylether, ethylene glycol monoethylether, ethylene glycol monobutylether, diethylene glycol monomethylether, diethylene glycol monobutylether, propylene glycol monomethylether, propylene glycol monobutylether, dipropylene glycol monomethylether, triethylene glycol monomethylether, ethylene glycol diacetate, ethylene glycol monomethylether acetate, triethylene glycol monomethylether, triethylene glycol monoethylether or ethylene glycol monophenylether), amine (for example, ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine or tetramethylpropylenediamine), and other polar solvents (for example, formamide, N,N-dimethylformamide, N,N-dimethylacetamide, dimethylsulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile or acetone). Meanwhile, the water-miscible organic solvents may be used in combination of two or more thereof.

Among the compounds, the alcohol-based solvent is particularly preferred. Further, in the ink composition of the present invention, it is preferred that the water-miscible organic solvent having the boiling point of 150° C. or more is contained, and examples thereof include 2-pyrrolidone and the like selected from the above. The water-miscible organic solvent is included in the amount of preferably 5% by mass to 60% by mass and particularly preferably 10% by mass to 45% by mass based on the total amount of the ink composition.

The surfactant may be included in the ink composition of the present invention to adjust liquid properties of the ink composition, and thus, discharging stability of the ink composition may be improved to provide excellent effects such as improvement of water resistance of the image or prevention of spreading of the printed ink composition.

The surfactant may be, for example, an anionic surfactant such as sodium dodecyl sulfate, sodium dodecyloxy sulfonate, or sodium alkylbenzene sulfonate, a cationic surfactant such as cetylpyridinium chloride, trimethylcetylammonium chloride, or tetrabutylammonium chloride, a non-ionic surfactant such as polyoxyethylenenonylphenylether, polyoxyethylenenaphthylether, or polyoxyethyleneoctylphenylether, or the like. Among the surfactants, the non-ionic surfactant is preferably used.

The content of the surfactant is 0.001% by mass to 20% by mass, preferably 0.005% by mass to 10% by mass, and more preferably 0.01% by mass to 5% by mass based on the ink composition.

In the case where the dye is an oil-soluble dye, the ink composition of the present invention may be prepared by emulsifying and dispersing the ink stock solution where the oil-soluble dye is dissolved in the high boiling point organic solvent in the aqueous medium. The boiling point of the high boiling point organic solvent used in the present invention is 150° C. or higher and preferably 170° C. or higher.

Examples thereof may include ester phthalates (for example, dibutyl phthalate, dioctyl phthalate, dicyclohexyl phthalate, di-2-ethylhexyl phthalate, decyl phthalate, bis(2,4-di-tert-amylphenyl)isophthalate or bis(1,1-diethylpropyl)phthalate), esters of phosphates or phosphones (for example, diphenyl phosphate, triphenyl phosphate, tricredyl phosphate, 2-ethylhexyldiphenyl phosphate, dioctylbutyl phosphate, tricyclohexyl phosphate, tri-2-ethylhexyl phosphate, tridodecyl phosphate or di-2-ethylhexylphenyl phosphate), ester benzoate (for example, 2-ethylhexyl benzoate, 2,4-dichloro benzoate, dodecyl benzoate or 2-ethylhexyl-p-hydroxy benzoate), amides (for example, N,N-diethyldodecaneamide, N,N-diethyllaurylamide), alcohols or phenols (isostearyl alcohol, 2,4-di-tert-amylphenol or the like), aliphatic esters (for example, dibutoxyethyl succinate, di-2-ethylhexyl succinate, 2-hexyldecyl tetradecanoate, tributyl citrate, diethyl azelate, isostearyl lactate or trioctyl citrate), aniline derivatives (N,N-dibutyl-2-butoxy-5-tert-octylaniline or the like), chlorinated paraffins (paraffins having a chlorine content of 10% to 80%), ester trimethinates (for example, tributyl trimethinate), dodecylbenzene, diisopropylnaphthalene, phenols (for example, 2,4-di-tert-amylphenol, 4-dodecyloxyphenol, 4-dodecyloxycarbonylphenol, or 4-(4-dodecyloxyphenylsulfonyl)phenol), carboxylic acids (for example, 2-(2,4-di-tert-amylphenoxy butyrate, 2-ethoxyoctane decanoate), alkyl phosphates (for example, di-2(ethylhexyl)phosphate, or diphenyl phosphate), or the like. The high boiling point organic solvent may have a mass ratio of 0.01 to 3 multiple amount and preferably 0.01 to 1.0 multiple amount based on the oil-soluble dye.

The high boiling point organic solvent may be used alone, or may be used as a mixture of various kinds [for example, tricredyl phosphate and dibutyl phthalate, trioctyl phosphate and di(2-ethylhexyl)sebacate, or dibutylphthalate and poly (N-t-butylacrylamide)].

Examples of compounds other than the aforementioned examples of the high boiling point organic solvent used in the present invention and/or a method of synthesizing the high boiling point organic solvent are described in, for example, U.S. Pat. Nos. 2,322,027, 2,533,514, 2,772,163, 2,835,579, 3,594,171, 3,676,137, 3,689,271, 3,700,454, 3,748,141, 3,764,336, 3,765,897, 3,912,515, 3,936,303, 4,004,928, 4,080,209, 4,127,413, 4,193,802, 4,207,393, 4,220,711, 4,239,851, 4,278,757, 4,353,979, 4,363,873, 4,430,421, 4,430,422, 4,464,464, 4,483,918, 4,540,657, 4,684,606, 4,728,599, 4,745,049, 4,935,321, and 5,013,639, EP 276, 319A, 286,253A, 289,820A, 309,158A, 309,159A, 309,160A, 509,311A, and 510,576A, Eastern Germany Patent Nos. 147,009, 157,147, 159,573, and 225,240A, British Patent No. 2,091,124A, Japanese Patent Application Laid-Open Nos. S48-47335, 50-26530, 51-25133, 51-26036, 51-27921, 51-27922, 51-149028, 52-46816, 53-1520, 53-1521, 53-15127, 53-146622, 54-91325, 54-106228, 54-118246, 55-59464, 56-64333, 56-81836, 59-204041, 61-84641, 62-118345, 62-247364, 63-167357, 63-214744, 63-301941, 64-9452, 64-9454, and 64-68745, and Japanese Patent Application Laid-Open No. 111-101543, 1-102454, 2-792, 2-4239, 2-43541, 4-29237, 4-30165, 4-232946, and 4-346338, and the like.

The high boiling point organic solvent has a mass ratio of 0.01 to 3.0 multiple amount and preferably 0.01 to 1.0 multiple amount based on the oil-soluble dye.

In the present invention, it is preferred that the oil-soluble dye or the high boiling point organic solvent is emulsified and dispersed in the aqueous medium. When emulsification and dispersion are performed, from the viewpoint of emulsibility, a low boiling point organic solvent may be used in some cases. The low boiling point organic solvent is an organic solvent having a boiling point of about 30° C. or higher and 150° C. or lower at normal pressure. For example, esters (for example, ethylacetate, butylacetate, ethyl propionate, β-ethoxyethylacetate or methylcellosolve acetate), alcohols (for example, isopropyl alcohol, n-butyl alcohol or secondary butyl alcohol), ketones (for example, methylisobutylketone, methylethylketone or cyclohexanone), amides (for example, dimethylformamide or N-methylpyrrolidone), ethers (for example, tetrahydrofuran or dioxane), or the like are preferably used, but are not limited thereto.

The emulsification and dispersion are performed by dispersing an oil phase where the dye is dissolved in a mixture solvent of the high boiling point organic solvent and, in some cases, the low boiling point organic solvent in an aqueous phase including water as a main body to form oily fine drops (the oil layer may be used as the ink stock solution or a matter where the oil layer is dispersed in the aqueous phase may be used as the ink stock solution). In this case, the component such as a surfactant, a wetting agent, a dye stabilizer, an emulsion stabilizer, a preservative, and a mycostats may be added to any one or both of the aqueous phase and the oil phase if necessary. A method of adding the oil phase to the aqueous phase is generally used as the emulsification method, but a so-called phase inversion emulsification method, in which the aqueous phase is added dropwise on the oil phase, may be preferably used. Meanwhile, in the case where the dye is water-soluble and the component is oil-soluble, the emulsification method may be applied.

Various surfactants may be used when the emulsification and dispersion are performed. For example, an anionic surfactant such as fatty acid salt, alkyl ester sulfate, alkylbenzene sulfonate, alkylnaphthalene sulfonate, dialkyl sulfosuccinate, alkyl ester phosphate, naphthalene sulfonic acid formalin condensate, or polyoxyethylenealkyl ester sulfate, and a nonionic surfactant such as polyoxyethylenealkylether, polyoxyethylenealkylallylether, polyoxyethylene fatty acid ester, sorbitan fatty acid ester, polyoxyethylene sorbitan fatty acid ester, polyoxyethylenealkylamine, glycerine fatty acid ester, oxyethyleneoxypropylene block copolymer are preferred. Further, SURFYNOLS (Air Products & Chemicals, Co., Ltd.) that is an acetylene-based polyoxyethylene oxide surfactant is preferably used. Further, an amine oxide type ampholytic surfactant such as N,N-dimethyl-N-alkylamine oxide and the like is preferred. Moreover, a matter exemplified as a surfactant on pp. 37 to 38 of Japanese Patent Application Laid-Open No. S59-157,636 and Research Disclosure No. 308119 (1989) may be used.

Further, the water-soluble polymer may be added together with the surfactant in order to ensure stabilization directly after emulsification. Polyvinyl alcohol, polyvinyl pyrrolidone, polyethylene oxide, polyacrylic acid, polyacrylamide, or a copolymer thereof may be preferably used as the water-soluble polymer. Further, it is preferred to use a natural water-soluble polymer such as polysaccharides, casein, or gelatin. Moreover, polyvinyl, polyurethane, polyester, polyamide, polyurea, polycarbonate, or the like obtained by polymerization of ester acrylates, ester methacrylates, vinylesters, acrylamides, methacrylamides, olefines, styrenes, vinylethers or acrylonitriles not substantially dissolved in the aqueous medium may be used together in order to stabilize the dye dispersed material. It is preferred that the polymers contain —$SO_3$—, or —COO—. In the case where the polymers not substantially dissolved in the aqueous medium are used together, the polymer is used in the amount of preferably 20% by mass or less and more preferably 10% by mass or less based on the high boiling point organic solvent.

In the case where the oil-soluble dye or the high boiling point organic solvent is dispersed by emulsification and dispersion to form the aqueous ink composition, it is particularly important to control the particle size thereof. When an image is formed by inkjet, it is essential to reduce the average particle size in order to increase a color purity or concentration. The volumetric average particle diameter is preferably 1 µm or less and more preferably 5 nm to 100 nm.

A method of measuring the volumetric average particle diameter and the particle size distribution of the dispersed particles is a static light scattering method, a dynamic light scattering method, or a centrifugal precipitation method, and the volumetric average particle diameter and the particle size distribution of the dispersed particles may be easily measured by a known method such as a method described on pages 417 to 418 of Experimental Chemistry Lecture, $4^{th}$ ed. For example, dilution may be performed by distilled water so that the concentration of the particles in the ink composition is 0.1% by mass to 1% by mass, and the measurement may be easily performed by a commercial volumetric average particle diameter measuring device (for example, MICROTRAC UPA (manufactured by NIKKISO Co., Ltd.)). Moreover, the dynamic light scattering method using a laser Doppler effect is particularly preferred because the diameter of the particle having a small size can be measured.

The volumetric average particle diameter is an average particle diameter weighed in a particle volume, and obtained by dividing a multiple of the diameter of each particle and the volume of the particle by the total volume of the particles in a set of particles. The volumetric average particle diameter is described on page 119 of "Chemistry of Polymer Latex (written by Muroi Souichi, Polymer Publication Association)".

Further, it is apparent that the presence of coarse particles very significantly affects printing performance. That is, it can be seen that the coarse particles clog the nozzle of the head or form impurities even when the coarse particles do not clog the nozzle not to discharge the ink composition or to cause twisting of discharging, thus significantly affecting printing performance. In order to prevent this, it is important to suppress the number of particles having a size of 5 µm or more in 1 µl of the ink composition when the ink composition is formed to 10 or less and the number of particles having a size of 1 µm or more to 1000 or less. A known centrifugal method, fine filtration method, and the like may be used as a method of removing the coarse particles. The separation means may be used immediately after emulsification and dispersion are performed, or may be used after various kinds of components such as a wetting agent or a surfactant are applied to an emulsified and dispersed material and immediately before the components are filled in an ink cartridge. As an effective means of reducing the average particle size and removing coarse particles, a mechanical emulsifier may be used.

As the emulsifier, a known device such as a simple stirrer or impeller stirring type, an inline stirring type, a mill type such as a colloid mill, and an ultrasonic type may be used, and it is particularly preferred to use a high pressure homogenizer. The detailed mechanism of the high pressure homogenizer is described in U.S. Pat. No. 4,533,254, Japanese Patent Application Laid-Open No. H6-47264, and the like, and there are a GAULIN homogenizer (A. P. V GAULIN INC.), a microfluidizer (MICROFLUIDEX INC.), an altimizer (SUGINO MACHINE LIMITED) or the like as a commercial device.

Further, currently, a high pressure homogenizer having a mechanism where micronizing is performed in an ultra-high pressure jet stream as described in U.S. Pat. No. 5,720,551 is particularly useful to emulsification and dispersion of the present invention. Examples of the emulsifier using the ultra-high pressure jet stream may include DeBEE2000 (BEE INTERNATIONAL LTD.).

The pressure when emulsification is performed by the high pressure emulsification and dispersion device is 50 MPa or more, preferably 60 MPa or more, and more preferably 180 MPa or more.

For example, after emulsification is performed by an stirring emulsifier, as a method of performing passage through the high pressure homogenizer, a method of using two kinds or more emulsifiers together is particularly preferred method. Further, a method of performing emulsification and dispersion by the emulsifier once, adding the component such as the wetting agent or the surfactant, and performing passage through the high pressure homogenizer again while the ink composition is filled in the cartridge is a preferred method. In the case where the high boiling point organic solvent and the low boiling point organic solvent are included, it is preferred to remove the low boiling point solvent from the view points of stability of the emulsified material and safety sanitization. As the method of removing the low boiling point solvent, various kinds of known methods may be used according to a kind of solvent. That is, the method is a vaporization method, a vacuum vaporization method, an ultra filtration, or the like. It is preferred that a process of removing the low boiling point organic solvent is performed as soon as possible immediately after emulsification.

Meanwhile, a method of preparing the ink composition for inkjet is described in detail in each official gazette of Japanese Patent Application Laid-Open Nos. H5-148436, 5-295312, 7-97541, 7-82515, and 7-118584, which may be used to prepare the ink composition of the present invention.

A functional component for providing various functions to the ink composition may be included in the ink composition of the present invention. For example, the functional component may be various kinds of solvents, a drying preventing agent for preventing clogging of the nozzle by drying of the ink composition, a permeation promoting agent for allowing the ink composition to permeate through paper more well, a UV absorbent, an antioxidant, a viscosity regulator, a surface tension regulator, a dispersant, a dispersion stabilizer, a mycostats, a rust inhibitor, a pH adjusting agent, an antifoaming agent, a chelating agent, or the like, and in the ink composition of the present invention, the component may be appropriately selected and used in an appropriate amount. The functional components are a kind of compound and include a matter having one or two or more functions. Accordingly, in a mixing ratio of the following functional components, in the case where the functions overlap, treatment of the functional component is performed by independently calculating the compound to each functional component.

It is preferred that the drying preventing agent used in the present invention is a water-soluble organic solvent having vapor pressure that is lower than that of water. Specific examples thereof may include polyvalent alcohols represented by ethylene glycol, propylene glycol, diethylene glycol, polyethylene glycol, thiodi glycol, dithiodi glycol, 2-methyl-1,3-propandiol, 1,2,6-hexanetriol, an acetylene glycol derivative, glycerine, or trimethylolpropan, low alkylethers of polyvalent alcohol such as ethylene glycol monomethyl (or ethyl)ether, diethylene glycol monomethyl (or ethyl)ether, or triethylene glycol monoethyl (or butyl)ether, heterocyclic rings such as 2-pyrrolidone, N-methyl-2-pyrrolidone, 1,3-dimethyl-2-imidazolidinone, or N-ethylmorpholine, a sulfur-containing compound such as sulfolan, dimethylsulfoxide, or 3-sulfolene, a polyfunctional compound such as diacetone alcohol or diethanol amine, or a urea derivative. Among the examples, polyvalent alcohol such as glycerine or diethylene glycol is more preferred. Further, the drying preventing agent may be used alone or two kinds or more may be used together. It is preferred that the drying preventing agent is included in the amount of 10% by mass to 50% by mass in the ink composition.

As the permeation promoting agent used in the present invention, alcohols such as ethanol, isopropanol, butanol, di(tri)ethylene glycol monobutylether, or 1,2-hexanediol, sodium lauryl sulfate, sodium oleate, a non-ionic surfactant, or the like may be used. If the aforementioned permeation promoting agent is included in the amount of 10% by mass to 30% by mass in the ink composition, there is a sufficient effect, and it is preferred to use the permeation promoting agent in the addition amount not causing spreading of print and print-through.

As the UV absorbent used to improve a preservation property of the image in the present invention, a compound absorbing UV to emit fluorescence, that is, a so-called fluorescent brightening agent, which is represented by a benzotriazole-based compound described in the official gazettes of Japanese Patent Application Laid-Open Nos. S58-185677 and 61-190537, and Japanese Patent Application Laid-Open Nos. S2-782, 5-197075, and 9-34057, a benzophenone-based compound described in the official gazettes of Japanese Patent Application Laid-Open No. H46-2784, Japanese Patent Application Laid-Open No. H5-194483, and U.S. Pat. No. 3,214,463, a cinnamic acid-based compound described in the official gazettes of Japanese Patent Publication Nos. S48-30492 and 56-21141, and Japanese Patent Application Laid-Open No. H10-88106, a triazine-based compound described in the official gazettes of Japanese Patent Application Laid-Open Nos. H4-298503, 8-53427, 8-239368, and 10-182621, and Japanese Patent Application Laid-Open No. H8-501291, a compound described in Research Disclosure No. 24239, and stibene and benzooxazole-based compounds may be used.

In the present invention, as the antioxidant used in order to improve a preservation property of the image, various kinds of organic and metal complex-based discoloration prevention agents may be used. The organic discoloration prevention agent is hydroquinones, alkoxyphenols, dialkoxyphenols, phenols, anilines, amines, indanes, cromanes, alkoxyanilines, heterocyclics, or the like, and the metal complex is a nickel complex, a zinc complex, or the like. More specifically, the compound described in the patent cited in Paragraphs I to J of VII of Research Disclosure No. 17643, Research Disclosure Nos. 15162, the left column on page 650 of Research Disclosure No. 18716, page 527 of Research Disclosure No. 36544, page 872 of Research Disclosure No. 307105, and Research Disclosure No. 15162, or a compound included in Formula of a representative compound and examples of the compounds described on pages 127 to 137 of the official gazette of Japanese Patent Application Laid-Open No. S62-215272 may be used.

The rust inhibitor used in the present invention may be, for example, an acid sulfite salt, sodium thiosulfate, thioglycolic acid ammon, diisopropylammonium nitrite, pentaerythritol tetranitrate, dicyclohexylammonium nitrite, benzotriazole, or the like. It is preferred that the rust inhibitor is used in the amount of 0.02% by mass to 5.00% by mass in the ink composition.

Conductivity of the ink composition of the present invention is in a range of 0.01 S/m to 10 S/m. Among the ranges, the preferred range is 0.05 S/m to 5 S/m.

The conductivity may be measured by an electrode method using commercial saturated potassium chloride. The conductivity may be mainly controlled by an ion concentration in the aqueous solution. In the case where the salt concentration is high, desalination may be performed by using an ultrafilter membrane or the like. Further, in the case where conductivity is adjusted by adding the salt, the conductivity may be adjusted by adding various organic salts or inorganic salts.

As the inorganic salt, an inorganic compound such as potassium halide, sodium halide, sodium sulfate, potassium sulfate, sodium hydrogen sulfate, potassium hydrogen sulfate, sodium nitrate, potassium nitrate, sodium hydrogen carbonate, potassium hydrogen carbonate, sodium phosphate, sodium phosphate dibasic, boric acid, potassium dihydrogen phosphate, or sodium dihydrogen phosphate, or an organic compound such as sodium acetate, potassium acetate, potassium tartarate, sodium tartarate, sodium benzoate, potassium benzoate, sodium p-toluenesulfonate, potassium saccharate, potassium phthalate, sodium picolate may be used.

Further, conductivity may be adjusted by selecting the component of the aqueous medium as described below.

It is preferred that the viscosity of the ink composition of the present invention is 1 mPa·s to 30 mPa·s at 25° C. The viscosity is more preferably 2 mPa·s to 15 mPa·s, and particularly preferably 2 mPa·s to 10 mPa·s. If the viscosity is more than 30 mPa·s, a fixability speed of the recorded image is reduced, thus reducing discharging performance. If the viscosity is less than 1 mPa·s, since the recorded image is spread, a quality thereof is reduced.

The viscosity may be arbitrarily adjusted by the addition amount of the ink solvent. The ink solvent is, for example, glycerine, diethylene glycol, triethanolamine, 2-pyrrolidone, diethylene glycol monobutylether, triethylene glycol monobutylether or the like.

Further, a viscosity regulator may be used. The viscosity regulator may be, for example, a water-soluble polymer such as celluloses and polyvinyl alcohol, a non-ionic surfactant, or the like. More details are described in Ch. 9 of "Viscosity Adjustment Technology" (Technical Information Institute Co., Ltd. 1999) and pages 162 to 174 of "Chemicals for Inkjet Printer (98 enlarged)-Investigation of trend and prospect of development of materials-" (CMC, 1997).

The method of measuring the viscosity of the solution is described in detail in Z8803 of JIS, and the viscosity may be easily measured by a viscometer of a commercial product. For example, a rotation type is a B type viscometer or an E type viscometer of TOKYO KEIKI INC. In the present invention, the viscosity was measured by a vibration VM-100A-L type of Yamaichi Electronics Co., Ltd. at 25° C. The unit of the viscosity is pascal·sec (Pa·s), but millipascal·sec (mPa·s) is generally used.

Surface tension of the ink composition used in the present invention is any one of dynamic and static surface tensions, but is preferably 20 mN/m to 50 mN/m and more preferably 20 mN/m to 40 in N/m at 25° C. If the surface tension is more than 50 mN/m, printing quality is significantly reduced from the viewpoints of discharging stability, spreading in mixing colors, and mustaches. Further, if the surface tension of the ink composition is 20 mN/m or less, printing defects may occur due to attachment of the ink composition to the hard surface while discharging is performed.

Various kinds of cationic, anionic, non-ionic and betaine-based surfactants may be added for the purpose of adjusting the surface tension. Further, the surfactants may be used in combination of two or more thereof.

As the static surface tension measuring method, a capillary rise method, a dropping method, a ring transfer method, or the like are known, but in the present invention, as the static surface tension measuring method, a vertical plate method is used. If a thin plate of glass or platinum is partially immersed in a solution and vertically suspended, the surface tension of the solution downwardly acts according to the contact length of the solution and the plate. This force may be balanced with regard to upward force to measure the surface tension.

Further, as the dynamic surface tension measuring method, for example, as described in "New Experimental Chemistry Lecture, Vol. 18, Interface and Colloid" [MARUZEN CO., LTD., pp. 69 to 90 (1977)], a vibration jet method, a meniscus falling method, a maximum bubble pressure method, and the like are known, and a liquid membrane breaking method as described in the official gazette of Japanese Patent Application Laid-Open No. H3-2064 is known, but in the present invention, a bubble pressure differential pressure method is used as the dynamic surface tension measuring method. Hereinafter, a measuring principle and a method thereof will be described.

If bubbles are generated in the solution agitated to be homogenized, a new gas-liquid interface is formed to allow molecules of the surfactant in the solution to gather at the water surface at a constant rate. When the bubble rate (generating rate of bubbles) is changed, if the generating rate is reduced, since more surfactant molecules gather at the surfaces of bubbles, the maximum bubble pressure immediately before the bubbles burst may be reduced to detect the maximum bubble pressure (surface tension) to the bubble rate. The preferred measurement of the dynamic surface tension may be a method of generating bubbles in a solution by using two large and small probes to measure a differential pressure of two probes in a maximum bubble pressure state, thus calculating the dynamic surface tension.

The amount of the nonvolatile component in the ink composition of the present invention is preferably 10% by mass to 70% by mass based on the total amount of the ink composition from the viewpoints of discharging stability or print image quality of the ink composition, various kinds of fastnesses of the image, spreading of the image after printing, or a reduction in stickiness of a print surface, and more preferably 20% by mass to 60% by mass from the viewpoints of discharging stability of the ink composition or a reduction in spreading of the image after printing.

Herein, the nonvolatile component means a liquid or solid component or a high molecular weight component having a boiling point of 150° C. or more under 1 atmosphere. The nonvolatile component of the ink composition for inkjet is a dye, a high boiling point solvent, a polymer latex added if necessary, a surfactant, a dye stabilizer, a mycostats, a buffering agent, or the like, and since most of the nonvolatile components other than the dye stabilizer reduce dispersion stability of the ink composition and are present on inkjet image-receiving paper even after printing, stabilization by association of the dyes on the image-receiving paper is hindered to worsen various kinds of fastnesses of the image portion or spreading of the image under the high humidity condition.

In the present invention, the high molecular weight compound can be included. Herein, the high molecular weight compound represents all polymer compounds having a number average molecular weight of 5000 or more contained in the ink composition. The polymer compounds may be a water-soluble polymer compound substantially dissolved in the aqueous medium, a water dispersible polymer compound such as a polymer latex or a polymer emulsion, an alcohol-soluble polymer compound dissolved in polyvalent alcohol used as an auxiliary solvent, or the like, but any matter substantially homogeneously dissolved or dispersed in the ink composition is included in the high molecular weight compound of the present invention.

Specific examples of the water-soluble polymer compound may include a water-soluble polymer such as polyvinyl alcohol, silanol denatured polyvinyl alcohol, carboxymethyl cellulose, hydroxyethyl cellulose, polyvinyl pyrrolidone, polyalkylene oxide such as polyethylene oxide or polypropylene oxide, a polyalkylene oxide derivative, a natural water-soluble polymer such as polysaccharides, starch, cationized starch, casein, or gelatin, an aqueous acryl resin such as polyacrylic acid, polyacrylamide, a copolymer thereof, an aqueous alkyde resin, or a water-soluble polymer compound having —$SO_3$— and —COO— groups in a molecule thereof and substantially dissolved in the aqueous medium.

Further, the polymer latex may be a styrene-butadiene latex, a styrene-acryl latex, a polyurethane latex, or the like. Moreover, the polymer emulsion may be an acryl emulsion or the like. The water-soluble polymer compound can be used either alone or in combination of two kinds or more thereof.

The water-soluble polymer compound is a viscosity regulator as described above, and is used to adjust the viscosity of the ink composition in a viscosity region where a discharging property is favorable, and if the addition amount thereof is large, the viscosity of the ink composition is increased to reduce discharging stability of the ink composition, such that the nozzle is easily clogged by the precipitate over time with regard to the ink composition.

The addition amount of the polymer compound of the viscosity regulator depends on the molecular weight of the added compound (the addition amount may be reduced as the molecular weight is increased), but the addition amount is 0% by mass to 5% by mass, preferably 0% by mass to 3% by mass, and more preferably 0% by mass to 1% by mass based on the total amount of the ink composition.

Further, in the present invention, a dispersant, various kinds of aforementioned cationic, anionic, non-ionic and betaine-based surfactants as a dispersion stabilizer, fluorine and silicon-based compounds as an antifoaming agent, a chelating agent represented by EDTA, or the like may be used if necessary.

The reflection type media that is a print medium suitable used in the present invention will be further described. The reflection type media may be a recording paper, a recording film, or the like. In the recording paper and the recording film, a support is formed of a chemical pulp such as LBKP or NBKP, a mechanical pulp such as GP, PGW, RMP, TMP, CTMP, CMP or CGP, a used-paper pulp such as DIP, or the like, and, if necessary, a matter manufactured by various kinds of devices such as a fourdrinier paper machine or a rotoformer paper machine by mixing additives known in the art, such as a pigment, a binder, a sizing agent, a fixability agent, a cationic agent, a strength additive for paper, or the like may be used. In addition to the aforementioned support, any matter of a synthetic paper and a plastic film sheet may be used as the support, and it is preferred that the thickness of the support is 10 μm to 250 μm and the basis weight thereof is 10 g/m$^2$ to 250 g/m$^2$.

An image-receiving material of the ink composition and the ink set of the present invention may be obtained by forming an image-receiving layer and a back coat layer on the support, or after a size press or an anchor coat layer is formed by starch, polyvinyl alcohol, or the like, the image-receiving material may be obtained by forming the image-receiving layer and the back coat layer. Further, the support may be subjected to planarization treatment by a calender device such as a machine calender, a TG calender, or a soft calender.

As the support, a paper or plastic film where polyolefins (e.g., polyethylene, polystyrene, polybutene and a copolymer thereof) or polyethylene terephthalates are laminated on both surfaces thereof is more preferably used. It is preferred that a white pigment (e.g., titanium oxide or zinc oxide) or a coloring dye (e.g., cobalt blue, navy blue or neodymium oxide) be added to polyolefins.

A porous material or an aqueous binder is included in the image-receiving layer formed on the support. Further, it is preferred that the pigment is included in the image-receiving layer, and a white pigment is preferred as the pigment. The white pigment may be an inorganic white pigment such as calcium carbonate, kaolin, talc, clay, diatomite, synthetic amorphous silica, aluminum silicate, magnesium silicate, calcium silicate, aluminum hydroxide, alumina, lithopone, zeolite, barium sulfate, calcium sulfate, titanium dioxide, zinc sulfide, or zinc carbonate, an organic pigment such as a styrene-based pigment, an acrylic pigment, a urea resin, or a melamine resin, or the like. A porous white inorganic pigment is particularly preferred, and synthetic amorphous silica having a large fine pore area or the like is particularly suitable. Any one of silicic acid anhydride obtained by a dry manufacturing method (gas phase method) and water-containing silicic acid obtained by a wet manufacturing method can be used as synthetic amorphous silica.

As the recording paper including the pigment in an image-receiving layer, specifically, matters disclosed in Japanese Patent Application Laid-Open Nos. 1110-81064, 10-119423, 10-157277, 10-217601, and 11-348409, Japanese Patent Application Laid-Open Nos. 2001-138621, 2000-43401, 2000-211235, 2000-309157, 2001-96897, and 2001-138627, Japanese Patent Application Laid-Open Nos. H11-91242, 8-2087, 8-2090, 8-2091, 8-2093, 8-174992, and 11-192777, Japanese Patent Application Laid-Open No. 2001-301314, and the like may be used.

The aqueous binder included in the image-receiving layer may be a water-soluble polymer such as polyvinyl alcohol, silanol denatured polyvinyl alcohol, starch, cationic starch, casein, gelatin, carboxymethyl cellulose, hydroxyethyl cellulose, polyvinylpyrrolidone, polyalkylene oxide, or a polyalkylene oxide derivative, a water dispersible polymer such as a styrenebutadiene latex or an acryl emulsion, or the like. The aqueous binder may be used either alone or in combination of two kinds or more thereof. In the present invention, among the polymers, polyvinyl alcohol or silanol denatured polyvinyl alcohol is particularly suitable from the viewpoints of an attachment property to the pigment and peeling resistance of an ink-receiving layer.

The image-receiving layer may include a mordant, a insolubilizer, a light resistance improving agent, a gas resistance improving agent, a surfactant, a hardening agent, or other additives in addition to the pigment and the aqueous binder.

It is preferred that a mordant added to the image-receiving layer be immobilized. To this end, a polymer-mordant is preferably used.

The polymer-mordant is described in each official gazette of Japanese Patent Application Laid-Open Nos. S48-28325, 54-74430, 54-124726, 55-22766, 55-142339, 60-23850, 60-23851, 60-23852, 60-23853, 60-57836, 60-60643, 60-118834, 60-122940, 60-122941, 60-122942, and 60-235134, Japanese Patent Application Laid-Open No. H1-161236, and each specification of U.S. Pat. Nos. 2,484,430, 2,548,564, 3,148,061, 3,309,690, 4,115,124, 4,124,386, 4,193,800, 4,273,853, 4,282,305, and 4450224. An image-receiving material including the polymer-mordant described on pages 212 to 215 of the official gazette of Japanese Patent Application Laid-Open No. H1-161236 is particularly preferred. If the polymer-mordant described in the same official gazette is used, an image having excellent image quality may be obtained, and light resistance of the image is improved.

The insolubilizer is effective to insolubilization of the image, and it is particularly preferred that a cation resin is an insolubilizer. The cation resin may be polyamidepolyamineepichlorohydrin, polyethyleneimine, polyaminesulfone, dimethyldiallylammonium chloride polymer, cation polyacrylamide, or the like. The content of the cation resin is preferably 1% by mass to 15% by mass and particularly preferably 3% by mass to 10% by mass based on the total solid of the ink-receiving layer.

The light resistance improving agent and the gas resistance improving agent may be a phenol compound, a hindered phenol compound, a thioether compound, a thiourea compound, a thiocyanic acid compound, an amine compound, a hindered amine compound, a TEMPO compound, a hydrazine compound, a hydrazide compound, an amidine compound, a vinyl group-containing compound, an ester compound, an amide compound, an ether compound, an alcohol compound, a sulfuric acid compound, saccharides, a water-soluble reducing compound, organic acid, inorganic acid, hydroxy group-containing organic acid, a benzotriazole compound, a benzophenone compound, a triazine compound, a heterocyclic compound, a water-soluble metal salt, an organic metal compound, a metal complex, or the like.

Specific examples of the compounds may include matters described in Japanese Patent Application Laid-Open No. H10-182621, Japanese Patent Application Laid-Open No. 2001-260519, Japanese Patent Application Laid-Open No. 2000-260519, Japanese Patent Publication No. H4-34953, Japanese Patent Publication No. H4-34513, Japanese Patent Publication No. H4-34512, Japanese Patent Application Laid-Open No. H11-170686, Japanese Patent Application Laid-Open No. S60-67190, Japanese Patent Application Laid-Open No. H7-276808, Japanese Patent Application Laid-Open No. 2000-94829, Japanese Patent Application Laid-Open No. H8-512258, Japanese Patent Application Laid-Open No. H11-321090, and the like.

The surfactant acts as a coating aid, a peeling improving agent, a slipping preventing agent, or an antistatic agent. The surfactant is described in each official gazette of Japanese Patent Application Laid-Open Nos. S62-173463 and 62-183457.

An organic fluoro compound may be used instead of the surfactant. It is preferred that the organic fluoro compound is hydrophobic. Examples of the organic fluoro compound include a fluorine-based surfactant, an oil phase fluorine-based compound (e.g., fluorine oil), and a solid type fluorine compound resin (e.g., a tetrafluoroethylene resin). The organic fluoro compound is described in each official gazette of Japanese Patent Publication No. 557-9053 (8th to 17th columns), and Japanese Patent Application Laid-Open Nos. S61-20994 and 62-135826.

As the hardening agent, materials and the like described on page 222 of the official gazette of Japanese Patent Application Laid-Open No. H1-161236, Japanese Patent Application Laid-Open No. 119-263036, Japanese Patent Application Laid-Open No. H10-119423, and Japanese Patent Application Laid-Open No. 2001-310547 may be used.

The other additives added to the image-receiving layer may be a pigment dispersant, a thickener, an antifoaming agent, a dye, a fluorescent brightening agent, a preservative, a pH adjusting agent, a matting agent, or the like. Meanwhile, the ink-receiving layer may have one layer or two layers.

The back coat layer can be provided into the recording paper and the recording film, and the component that may be added to the layer may be a white pigment, an aqueous binder, or other components.

The white pigment included in the back coat layer may be, for example, a white inorganic pigment such as precipitated calcium carbonate, ground calcium carbonate, kaolin, talc, calcium sulfate, barium sulfate, titanium dioxide, zinc oxide, zinc sulfide, zinc carbonate, satin white, aluminum silicate, diatomite, calcium silicate, magnesium silicate, synthetic amorphous silica, colloidal silica, colloidal alumina, pseudo-boehmite, aluminum hydroxide, alumina, lithopone, zeolite, hydrate halloysite, magnesium carbonate, or magnesium hydroxide, an organic pigment such as a styrene-based plastic pigment, an acrylic plastic pigment, polyethylene, microcapsules, a urea resin, or a melamine resin, or the like.

The aqueous binder included in the back coat layer may be a water-soluble polymer such as a styrene/maleate copolymer, a styrene/acrylate copolymer, polyvinyl alcohol, silanol denatured polyvinyl alcohol, starch, cationic starch, casein, gelatin, carboxymethyl cellulose, hydroxyethyl cellulose, or polyvinylpyrrolidone, a water dispersible polymer such as a styrenebutadiene latex or an acryl emulsion, or the like. The other component included in the back coat layer may be an antifoaming agent, a defoaming agent, a dye, a fluorescent brightening agent, a preservative, an insolubilizer, or the like.

A polymer fine particle dispersed material may be added to a constitutional layer (a white layer is included) of the inkjet recording paper and the recording film. The polymer fine particle dispersed material is used for the purpose of improvement in physical properties of the layer, such as dimensional stabilization, curling prevention, attachment prevention, and crack prevention of the layer. The polymer fine particle dispersed material is described in each official gazette of Japanese Patent Application Laid-Open Nos. S62-245258, 62-136648, and 62-110066. If the polymer fine particle dispersed material having a low glass transition temperature (40° C. or below) is added to the layer including the mordant, cracks or curling of the layer may be prevented. Further, even though the polymer fine particle dispersed material having a high glass transition temperature is added to the white layer, curling may be prevented.

The ink composition of the present invention may be used for the purpose other than inkjet recording. For example, the ink composition can be used in a material for a display image, a material forming an image of an interior decoration material, and a material forming an image of an exterior decoration material.

The material for the display image represents various kinds of matters such as posters, wall paper, decorating properties (decorative matters, dolls or the like), leaflets for commercial propaganda, packaging paper, wrapping materials, paper bags, vinyl bags, package materials, signs, drawings or attached images on lateral surfaces of transportation means (automobiles, buses, trams or the like), or suits having a logo. In the case where the dye of the present invention is a material forming a display image, the image includes all patterns by the dye recognized by humans, such as abstract designs, characters, and geometric patterns, in addition to the image having a narrow meaning.

The interior decoration material represents various kinds of matters such as wall paper, decorating properties (decorative matters, dolls or the like), members of lighting fixtures, members of furniture, and design members of floors or ceilings. In the case where the dye of the present invention is a material forming an image, the image includes all patterns by the dye recognized by humans, such as abstract designs, characters, and geometric patterns, in addition to the image having a narrow meaning.

The exterior decoration material represents various kinds of matters such as wall materials, roofing materials, signs, gardening materials, exterior decorating properties (decorative matters, dolls or the like), and members of external lighting fixtures. In the case where the dye of the present invention is a material forming an image, the image includes all patterns by the dye recognized by humans, such as abstract designs, characters, and geometric patterns, as well as the image having a narrow meaning.

In the aforementioned purpose, examples of the media on which the pattern is formed may include various matters such as paper, fibers, cloths (non-woven fabrics are included), plastics, metal, and ceramics. The dyeing type is performed such that a colorant is fixed by mordancy, printing, or a form of a reactive dye into which a reactive group is introduced. Among the types, it is preferred that dyeing is performed by the mordancy type.

In manufacturing the ink stock solution or the ink composition, ultrasonic vibration may be applied to a process of dissolving the additive such as the dye or the like.

The ultrasonic vibration is to remove bubbles by applying ultrasonic wave energy that is the same as or more than energy applied to a recording head in advance during a process of manufacturing the ink composition in order to prevent the ink composition from generating bubbles by pressure applied by the recording head.

The ultrasonic vibration adopts an ultrasonic wave generally having a vibration number of 20 kHz or more, preferably 40 kHz or more, and more preferably 50 kHz. Further, energy applied to liquid by the ultrasonic vibration is generally $2\times10^7$ J/m$^3$ or more, preferably $5\times10^7$ J/m$^3$ or more, and more preferably $1\times10^8$ J/m$^3$ or more. Further, a providing time of the ultrasonic vibration is generally about 10 min to 1 hour.

A process of providing the ultrasonic vibration always exhibits an effect after the dye is added to the medium. Even though the ultrasonic vibration is applied after the completed ink composition is preserved, the effect is exhibited. However, in the case of provision of the ultrasonic vibration when the dye is dissolved and/or dispersed in the medium, a bubble removing effect is large and dissolving and/or dispersion of the colorant in the medium by the ultrasonic vibration are promoted, which is preferred.

That is, at least the process of providing the ultrasonic vibration may be performed in any case of during and after the process of dissolving and/or dispersing the dye in the medium. In other words, at least the process of providing the ultrasonic vibration may be arbitrarily performed once or more until a product is obtained after the ink composition is prepared.

In the exemplary embodiment, the process of dissolving and/or dispersing the dye in the medium preferably has a process of dissolving the dye in a portion of the entire medium and a process of mixing the residual medium therewith, it is preferred to provide the ultrasonic vibration to at least one process, and it is more preferred to provide at least the ultrasonic vibration to the process of dissolving the dye in a portion of the entire medium.

The process of mixing the residual solvent therewith may be a single process or a plurality of processes. Further, it is preferred to use heat deaeration or reduced pressure deaeration together while manufacturing the ink composition by the present invention because a bubble removing effect of the ink composition is increased. It is preferred that the heat deaeration process or the reduced pressure deaeration process is performed together with or after the process of mixing the residual medium therewith. In the process of providing the ultrasonic vibration, means of generating ultrasonic vibration may be a known device such as a ultrasonic wave dispersion device.

When the ink stock solution or the ink composition of the present invention is manufactured, a process of removing dust that is a solid by filtration, which is performed after the solution is prepared is important. In this work, a filter is used, and in this case, the filter having an effective diameter of 1 μm or less, preferably 0.3 μm or less and 0.05 μm or more, and particularly preferably 0.3 μm or less and 0.25 μm or more is used. Various matters may be used as the material of the filter, and particularly, in the case of the ink composition of the water-soluble dye, it is preferred to use the filter manufactured for the purpose of an aqueous solvent. Among the filters, it is particularly preferred to use a filter manufactured by using a polymer material, from which the dust is difficult to be generated. In the filtration method, passage through the filter by a transport liquid may be performed, and any one method of pressure filtration and vacuum filtration may be used as the filtration method.

After the filtration, there are many cases where the solution receives the air. Since there are many cases where bubbles caused by the air are a factor of scattering the image in inkjet recording, it is preferred to separately perform the aforementioned defoaming process. In the defoaming method, the solution may be left after filtration, and various methods such as ultrasonic wave defoaming or vacuum defoaming using commercial devices and the like may be used as the defoaming method. In the case of defoaming by the ultrasonic wave, a defoaming operation may be performed for preferably 30 sec to 2 hours and more preferably 5 min to about 1 hour.

It is preferred that this work is performed by using a space such as a clean room or a clean bench in order to prevent mixing of dust during the work. In the present invention, it is particularly preferred that this work is performed in a space having the degree of cleaning of 1000 class or less. Herein, "the degree of cleaning" means a value measured by a dust counter.

In the present invention, a drop application volume on the recorded material of the ink composition is 0.1 pl or more and 100 pl or less. The drop application volume is in a range of preferably 0.5 pl or more and 50 pl or less, and particularly preferably 2 pl or more and 50 pl or less.

[Inkjet Recording Method, Ink Cartridge for Inkjet Recording, Inkjet Recording Device, and Inkjet Record]

The inkjet recording method of the present invention is a method of forming a colored image (simply called an image) on a recording target material by using ink for inkjet recording.

In the present invention, the inkjet recording method is not limited as long as image recording is performed by an inkjet printer by using the ink composition or the ink set of the present invention, and is used in a known manner, for example, a charge control manner discharging an ink composition using electrostatic force, a drop-on-demand manner (pressure pulse manner) using vibration pressure of a piezo element, a sound inkjet manner discharging an ink composition using radiation pressure by changing an electric signal into a sound beam and radiating the beam to the ink composition, a thermal inkjet (Bubble Jet®) manner using pressure generated by heating an ink composition to form bubbles, and the like.

In the inkjet recording method, a manner of injecting an ink composition that is called photo ink at a low concentration in a plurality of small volumes, a manner of improving an image by using a plurality of ink compositions having substantially the same color and different concentrations, and a manner of using a colorless transport ink composition are included. The drop application volume of the ink composition is mainly controlled by a print head.

For example, in the case of the thermal inkjet manner, it is possible to control the drop application volume by the structure of the print head. That is, drops having a desired size may be applied by changing an ink room, a heating portion, and a size of a nozzle. Further, even in the thermal inkjet manner, it is possible to apply drops having a plurality of sizes by ensuring a plurality of print heads having heating portions or nozzles having different sizes. In the case of the drop-on-demand manner using the piezo element, like the thermal inkjet manner, it is possible to change the drop application volume due to the structure of the print head, but as described below, it is possible to apply drops having a plurality of sizes on the print head having the same structure by controlling a waveform of a driving signal driving the piezo element.

It is preferred that a discharging frequency is 1 KHz or more when the drops of the ink composition of the present invention are applied to the recorded material.

In order to record an image having high image quality like a picture, a drop application density needs to be 600 dpi (the number of dots per 1 inch) or more to reproduce the image having high sharpness by small ink drops.

Meanwhile, in the application of the drops of the ink composition by the head having a plurality of nozzles, in a type where recording paper and the head move in orthogonal directions to perform recording, there are limits in that the number of heads that may be simultaneously driven is about several tens to 200, and several hundreds even though the head that is called a line head is a fixed type. This is because there is a limit in driving power or heat generated in the head affects the image not to simultaneously drive a plurality of head nozzles.

Herein, it is possible to increase a recording rate by increasing a driving frequency. In the case of the thermal inkjet manner, it is possible to control the drop application frequency by controlling a frequency of a head driving signal heating the head.

In the case of the piezo manner, it is possible to control the drop application frequency by controlling a frequency of a signal driving a piezo. Driving of the piezo head will be described. The drop application size, the drop application rate, and the drop application frequency are determined by a printer controller, and thus, an image signal to be printed becomes a signal driving the print head. The driving signal is supplied to the print head. The drop application size, the drop application rate, and the drop application frequency are controlled by the signal driving the piezo. Herein, the drop application size and the drop application rate are determined by the shape and the amplitude of the driving waveform, and the frequency is determined by a repetition period of the signal.

If the drop application frequency is set to 10 kHz, the head is driven every 100 microseconds, and recording of one line is finished at 400 microseconds. The recording paper may be printed at a rate of one paper per 1.2 sec by setting a moving rate of the recording paper so that the recording paper moves by 1/600 inches, that is, about 42 microns, per 400 microseconds.

The present invention relates to an ink cartridge for inkjet recording, in which the aforementioned ink for inkjet recording is filled.

The constitution of the printing device and the constitution of the printer used in the present invention is suitably an aspect disclosed in, for example, Japanese Patent Application Laid-Open No. H11-170527. Further, the ink cartridge is suitably a matter disclosed in, for example, Japanese Patent Application Laid-Open No. H5-229133. The constitution of absorption, a cap covering a printing head during absorption, and the like are suitably a matter disclosed in, for example, Japanese Patent Application Laid-Open No. H7-276671. Further, it is suitable to provide the filter for removing bubbles as disclosed in Japanese Patent Application Laid-Open No. H9-277552 around the head.

Further, it is suitable that the surface of the nozzle is subjected to water repelling treatment as described in the official gazette of Japanese Patent Application Laid-Open No. 2002-292878. The purpose may be a printer connected to a computer, or a device specified to print a picture.

In the inkjet recording method applied to the present invention, an average drop application rate may be 2 msec or more and preferably 5 m/sec or more when the ink composition is dropwisely applied to a recorded material. The drop application rate is controlled by controlling a shape and an amplitude of a waveform driving the head. Further, it is possible to perform drop application in a plurality of sizes by the same head by differentially using a plurality driving waveforms.

Hereinafter, the recording paper and the recording film used to perform inkjet printing by using ink of the present invention will be described.

In the recording paper and the recording film, a support is formed of a chemical pulp such as LBKP or NBKP, a mechanical pulp such as GP, PGW, RMP, TMP, CTMP, CMP, or CGP, a used-paper pulp such as DIP, or the like, and, if necessary, a matter manufactured by various kinds of devices such as a fourdrinier paper machine or a rotoformer paper machine by mixing additives known in the art, such as a pigment, a binder, a sizing agent, a fixability agent, a cationic agent, a strength additive for paper, or the like may be used. In addition to the aforementioned support, any matter of a synthetic paper and a plastic film sheet may be used, and it is preferred that the thickness of the support is 10 μm to 250 μm and the basis weight thereof is 10 g/m² to 250 g/m². The ink-receiving layer and the back coat layer may be formed on the support, or after a size press or an anchor coat layer is formed by starch, polyvinyl alcohol, or the like, the ink-receiving layer and the back coat layer may be formed. Further, the support may be subjected to planarization treatment by a calender device such as a machine calender, a TG calender, or a soft calender. In the present invention, paper and plastic films where polyolefins (e.g., polyethylene, polystyrene, polyethylene terephthalate, polybutene, and a copolymer thereof) are laminated on both surfaces thereof are more preferably used as the support. It is preferred that a white pigment (e.g., titanium oxide or zinc oxide) or a coloring dye (e.g., cobalt blue, navy blue or neodymium oxide) is added to polyolefins.

The inkjet record of the present invention is obtained by forming a colored image on a recording target material by using ink for inkjet recording of the present invention. Herein, formation of the image is suitably performed by adopting the inkjet recording method using the inkjet recording device.

Hereinafter, the present invention will be described in detail by the Examples, but the present invention is not limited thereto.

EXAMPLE

Hereinafter, the present invention will be described in more detail by the Examples. Materials, reagents, ratios, devices, operations, and the like described in the following Examples may be appropriately modified without departing from the spirit of the present invention. Therefore, the scope of the present invention is not limited to the following specific examples. Meanwhile, in the following Examples, "%" and "part" represent "% by mass" and "parts by mass", respectively, and "molecular weight" represents "mass average molecular weight", unless explicitly described to the contrary. Meanwhile, in the following synthesis schemes, M represents a monovalent countercation.

Synthesis Example 1

The synthesis scheme of BLACK-21 (M=Li) is as follows.

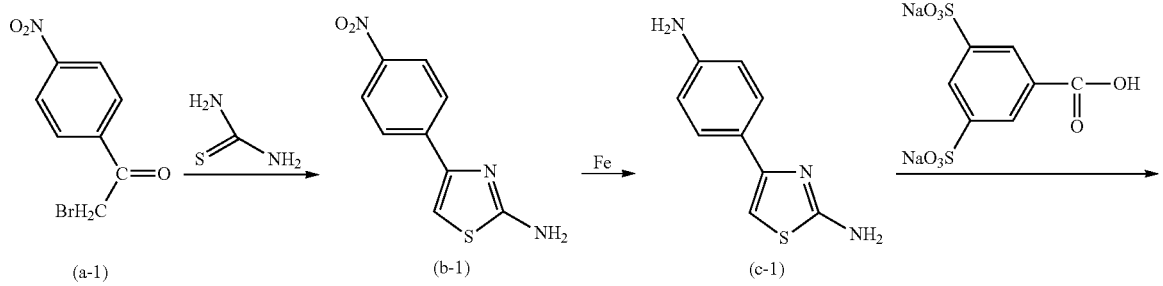

-continued
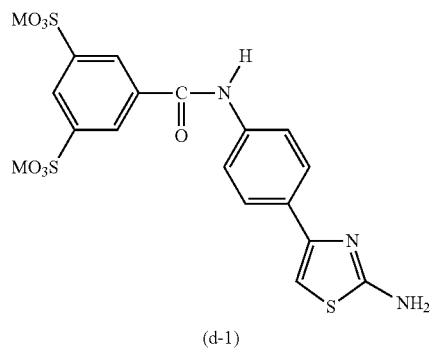
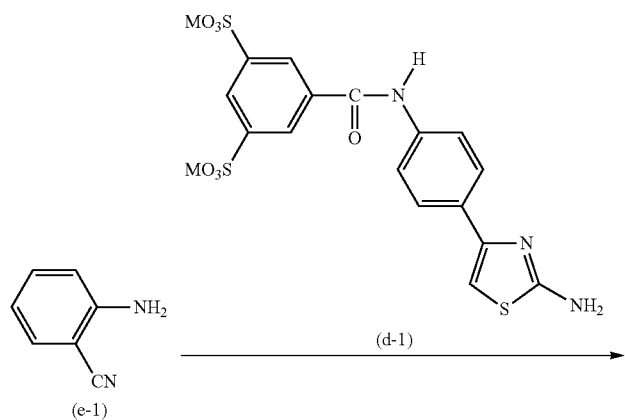
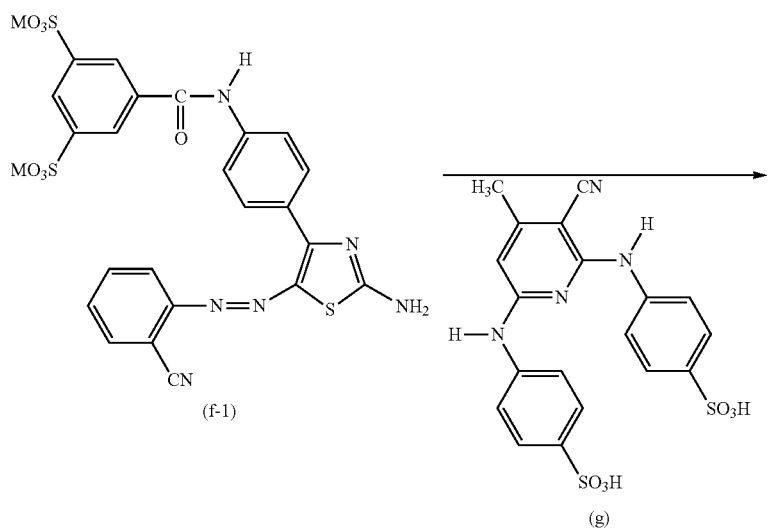

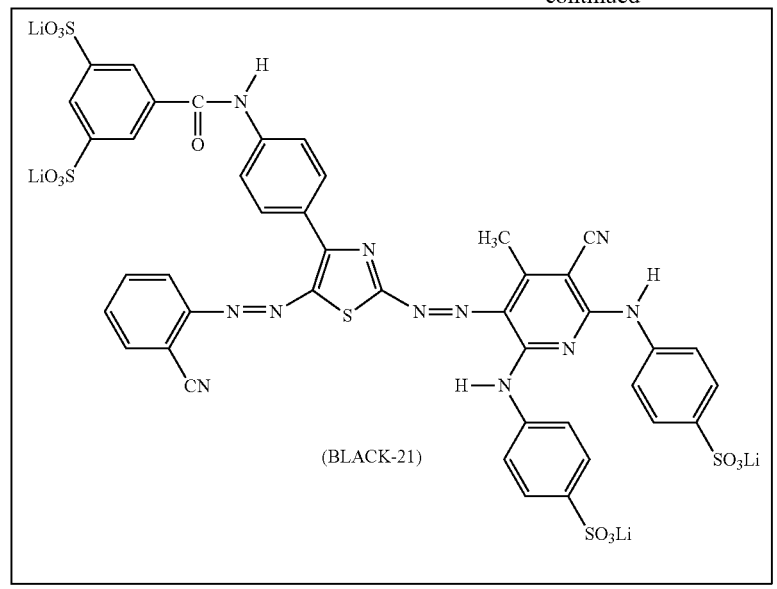

(BLACK-21)

(1) Synthesis of Intermediate (b-1):

40.0 g of 2-bromo-4'-nitroacetophenone (a-1; a product manufactured by Wako Pure Chemical Industries, Ltd.) was added to 120 ml of the aqueous solution of 12.5 g of thiourea, and stirred at 70° C. for 5 hours. After the crystal was separated by filtration, 400 ml of 5% sodium hydroxide aqueous solution was added, and stirred at room temperature for 3 hours, and the crystal was then separated by filtration. After drying was performed at 50° C., 35.5 g of a yellow crystal of Intermediate (b-1) was obtained.

(2) Synthesis of the Intermediate (c-1):

57.0 g of reduced iron, 5.0 g of ammonium chloride, 35 ml of water, and 250 ml of isopropyl alcohol were refluxed for 30 min, and 22.0 g of the intermediate (b-1) was added thereto, and refluxed and stirred for 1 hour. After the filtration, the filtrate was concentrated and dried to obtain 15.0 g of a yellow crystal of Intermediate (c-1).

(3) Synthesis of the Intermediate (d-1):

12.0 g of 1-ethyl-3-(3-dimethylaminopropyl)-carbodiimido hydrochloride (a product manufactured by Tokyo Chemical Industry Co., Ltd.) was added to a solution of 9.6 g of Intermediate (c-1), 19.5 g of 3,5-disulfobenzoic acid, 100 ml of water and 90 ml of acetonitrile, and stirred at room temperature for 4 hours. 30.0 g of lithium chloride was added, and the precipitated crystal was separated by filtration to obtain 20.0 g of a yellow crystal of Intermediate (d-1).

(4) Synthesis of Intermediate (f-1):

2.6 ml of concentrated hydrochloric acid was added to 12 g of 2-aminobenzonitrile (e-1; a product manufactured by Tokyo Chemical Industry Co., Ltd.) and 10 ml of water, and 3 ml of the aqueous solution including 0.7 g of sodium nitrite was added at 5° C. or below. The resultant solution was stirred as it was for 30 minutes, and 4.7 g of Intermediate (d-1) was added to the solution dissolved, in 50 ml of water and 25 ml of methanol at 20° C. or below. The solution was stirred as it was for 2 hours, and the precipitated crystal was separated by filtration to obtain 4.9 g of a brown crystal of Intermediate (f-1). The isolation yield was 73%.

(5) Synthesis of BLACK-21:

The pH of a solution of 4.9 g of Intermediate (f-1), 3.7 g of Intermediate (g), and 30 ml of water was set to 2.0 or less by hydrochloric acid, and 3.3 ml of isoamyl nitrite was added thereto and stirred at 40° C. for 2 hours. After the reaction was finished, the pH was adjusted to 8.4 by lithium hydroxide, 200 ml of isopropyl alcohol was added, and the precipitated crystal was separated by filtration to obtain 6.7 g of a black crystal (BLACK-21).

Synthesis Example 2

The synthesis scheme of BLACK-20 (M=Li) is as follows.

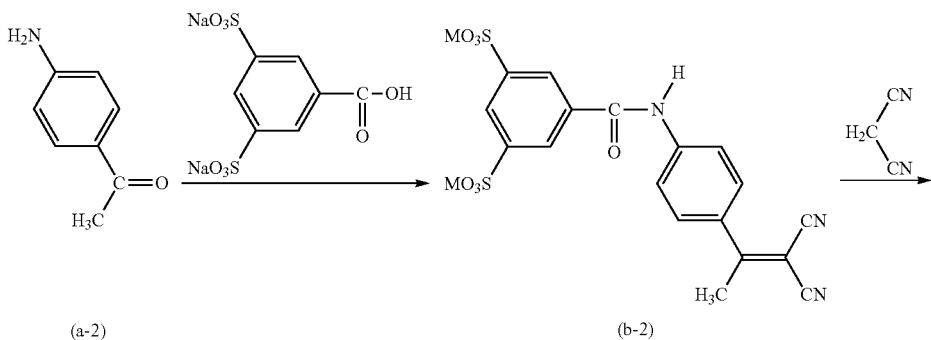

(a-2)    (b-2)

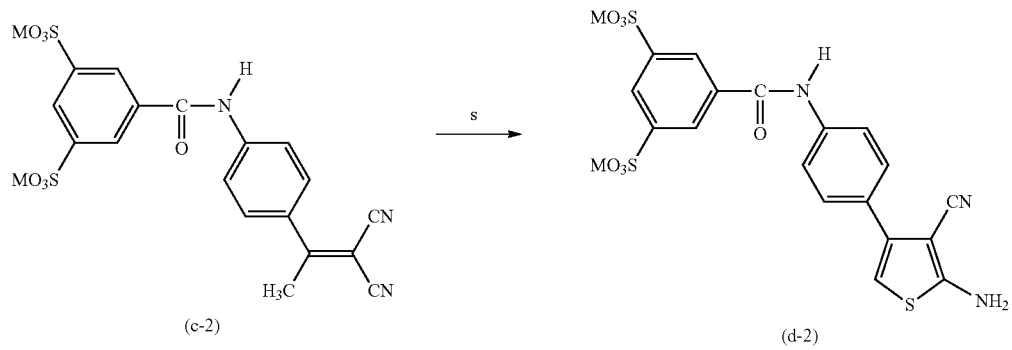
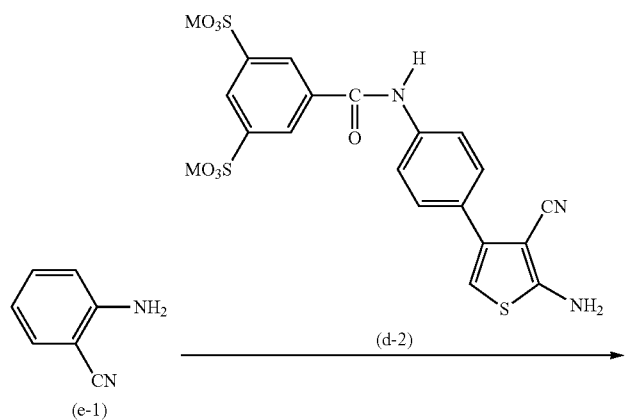
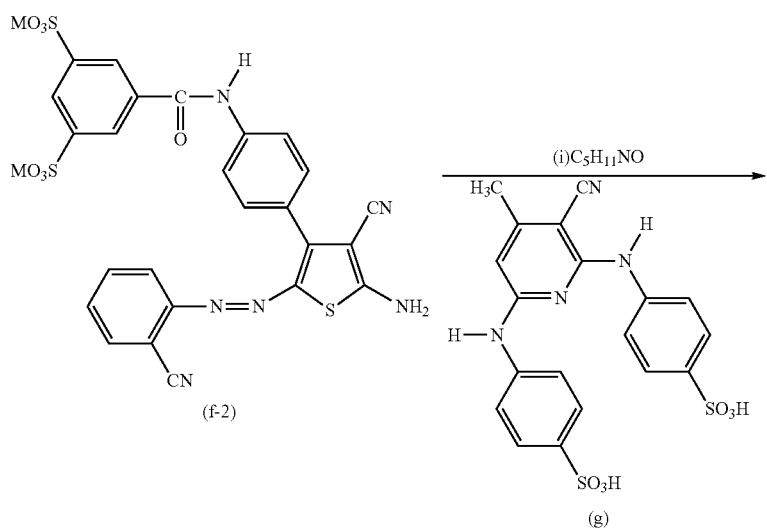

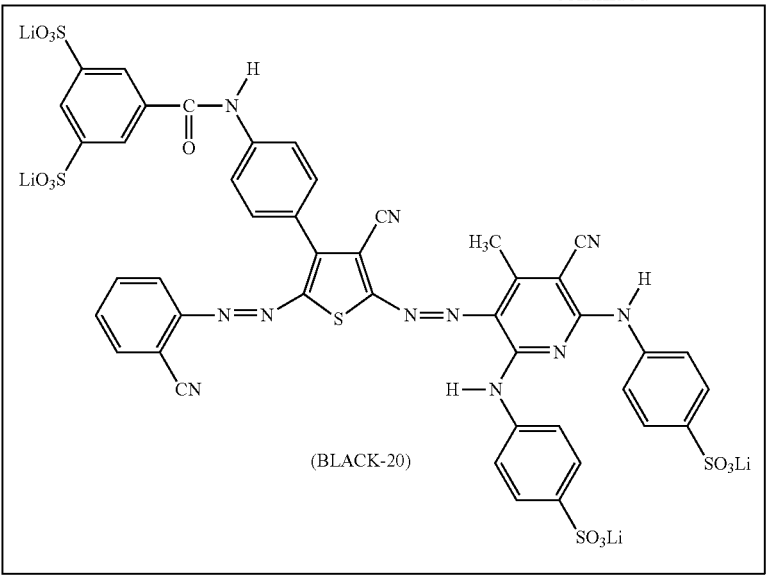

(BLACK-20)

(1) Synthesis of Intermediate (b-2):

13.5 g of p-aminoacetophenone (a-2; a product manufactured by Tokyo Chemical Industry Co., Ltd.) and 28.2 g of 3,5-disulfobenzoic acid were added to 100 mL of water and 100 mL of acetonitrile and completely dissolved by stirring at room temperature. 19.1 g of 1-ethyl-3-(3-dimethylaminopropyl)-carbodiimido hydrochloride (a product manufactured by Tokyo Chemical Industry Co., Ltd.) was added and stirred at room temperature for 4 hours. The reaction mixture was subjected to dust removal by filtration, and 50 g of lithium chloride was added at room temperature. The crystal was separated by filtration, washed twice with 100 mL of isopropanol, and dried at 80° C. to obtain 28.8 g of a white crystal of (b-2).

(2) Synthesis of Intermediate (c-2):

28.0 g of Intermediate (b-2), 13.9 g of malononitrile, 2.2 g of ammonium acetate, and 50 mL of toluene were put into a three-necked flask equipped with a Dean-Stark trap, and heated under reflux with stirring in an oil bath at 130° C. After 1 hour, the resultant was left standing to be cooled to room temperature, the solvent was distilled off under reduced pressure, and 50 mL of isopropanol was added to the residue. The crystal was separated by filtration, and then washed twice with 50 mL of isopropanol. Drying was performed at 80° C. to obtain 20.1 g of a brown crystal of (c-2).

(3) Synthesis of Intermediate (d-2):

19.0 g of Intermediate (c-2), 1.5 g of sulfur, and 1.4 g of lithium acetate were suspended in 100 mL of dimethylacetamide, and stirred at room temperature for 4 hours. After 8.4 g of lithium acetate and 200 mL of methanol were added, dust removal by filtration was performed to obtain 256.3 g of 7.4 wt % brown solution of Intermediate (d-2).

(4) Synthesis of Intermediate (f-2):

10.0 ml of concentrated hydrochloric acid was added to 5.0 g of 2-aminobenzonitrile (e-1; a product manufactured by Tokyo Chemical Industry Co., Ltd.) and 50 ml of water, and 12.5 ml of an aqueous solution of 2.9 g of sodium nitrite was added at the internal temperature of 5° C. or below. After stirring was performed at the internal temperature of 5° C. or below for 90 minutes, 0.5 g of amide sulfate was added, and subsequently stirred at the internal temperature of 5° C. for 15 minutes to obtain the diazonium solution. Separately, 256.3 g of Intermediate (d-2) was cooled to the internal temperature of 4° C., and the aforementioned diazonium solution was then added dropwise at the internal temperature of 6° C. or below for 30 minutes. After stirring at the internal temperature of 5° C. or below for 2 hours, the internal temperature was increased to 35° C. After stirring for 1.5 hours, the crystal was separated by filtration, and washed twice with 100 mL of isopropyl alcohol. Drying was performed at 80° C. to obtain 23.3 g of a brown colored crystal of Intermediate (f-2).

(5) Synthesis of BLACK-20:

The pH of a solution of 23.0 g of Intermediate (f-2), 16.7 g of Intermediate (g), and 135 ml of water was set to 2.0 or below by hydrochloric acid, and 14.9 ml of isoamyl nitrite was added thereto and stirred at 40° C. for 2 hours. After the reaction was finished, the pH was adjusted to 8.4 by lithium hydroxide, 900 ml of isopropyl alcohol was added, and the precipitated crystal was separated by filtration. After the obtained crystal was completely dissolved in the mixture solvent of 250 mL of water and 250 mL of methanol, 1000 mL of isopropanol was added dropwise. The crystal was separated by filtration, and then washed twice with 100 mL of isopropanol. The crystal was dissolved in 200 mL of water, 600 mL of isopropanol was added dropwise, and the precipitated crystal was separated by filtration. The crystal was washed twice with 100 mL of isopropanol and then dried at 80° C. to obtain 5.8 g of a black crystal of BLACK-20.

Synthesis Example 3
The synthesis scheme of BLACK-22 (M=Li) is as follows.
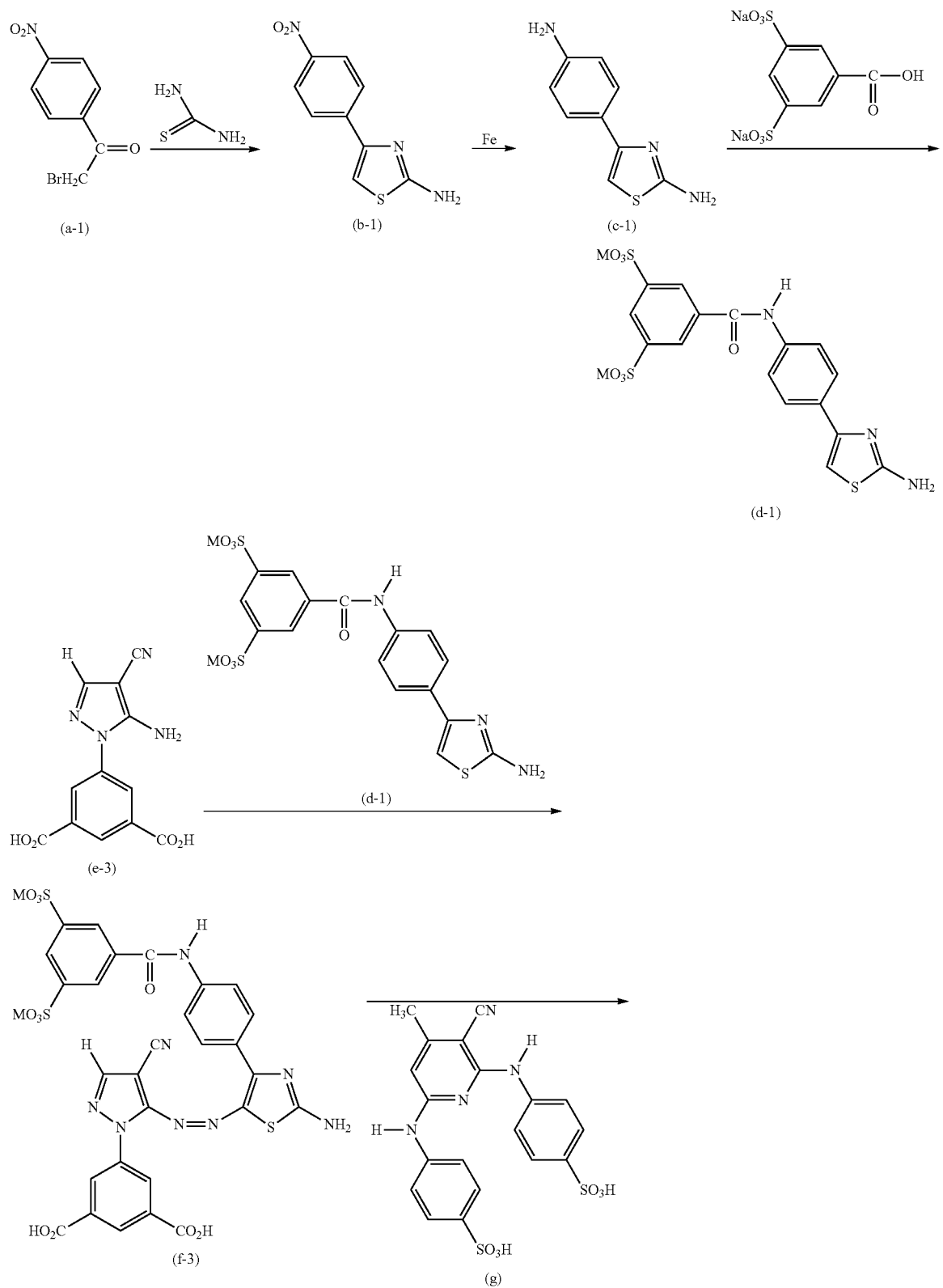

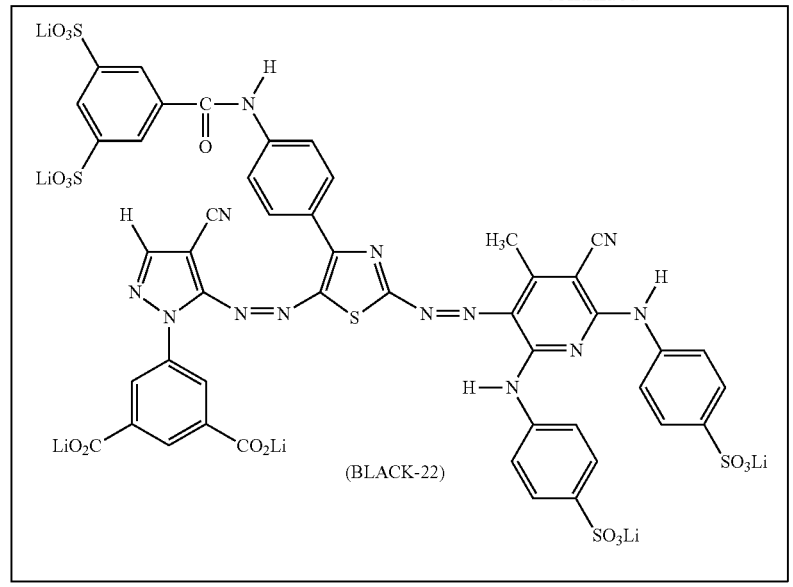

(BLACK-22)

(1) Synthesis of Intermediates (b-1), (c-1) and (d-1):

Synthesis was performed by the method described in Synthesis Example (1).

(2) Synthesis of Intermediate (f-3):

7 g of nitrosyl sulfuric acid was added to a solution of 13 ml of concentrated sulfuric acid and 59 ml of acetic acid at 5° C. or below, and then, 5.4 g of the intermediate (e-3) was added, and stirred as it was for 1 hour to obtain the diazonium solution. Separately, the solution in which 9.3 g of Intermediate (d-1) was dissolved in 50 ml of dimethylacetamide and 50 ml of methyl alcohol was prepared, and the diazonium solution thus obtained was added thereto at 30° C. or below. Stirring was performed as it was at room temperature for 2 hours, and the precipitated crystal was separated by filtration to obtain 6.3 g of a brown crystal of Intermediate (f-3).

(3) Synthesis of BLACK-22:

The pH of a solution of 6.3 g of Intermediate (f-3), 3.9 g of Intermediate (g) and 60 ml of water was set to 2.0 or below by hydrochloric acid, and 3.4 ml of isoamyl nitrite was added thereto and stirred at 40° C. for 2 hours. After the reaction was finished, the pH was adjusted to 8.4 by lithium hydroxide, 200 ml of isopropyl alcohol was added, and the precipitated crystal was separated by filtration. Further, dissolution was performed in 50 ml of water and 50 ml of methyl alcohol, 200 ml of isopropyl alcohol was added, and the precipitated crystal was separated by filtration to obtain 5.2 g of a black crystal of BLACK-22.

Synthesis Example 4

The synthesis scheme of BLACK-2 (M=Li) is as follows.

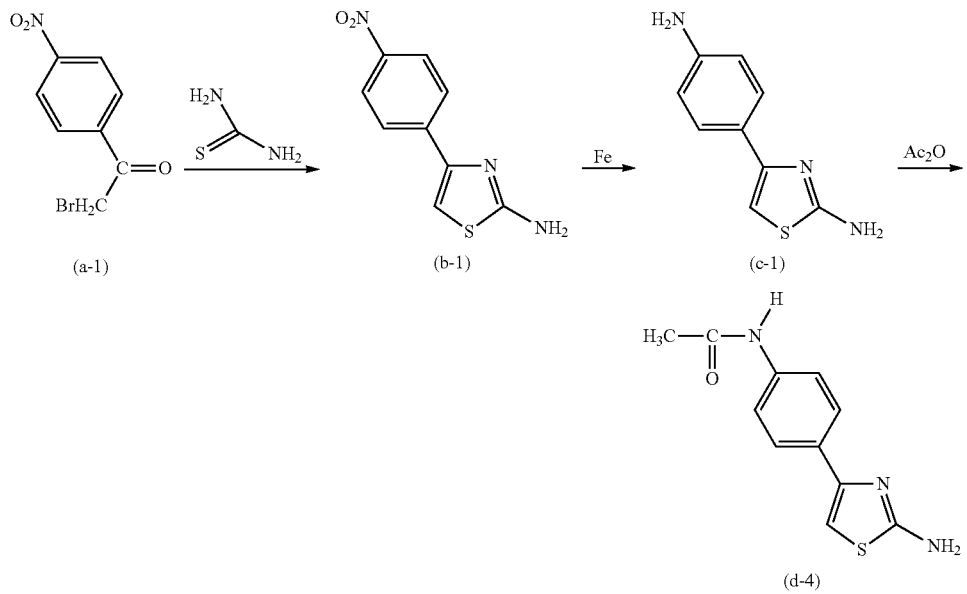

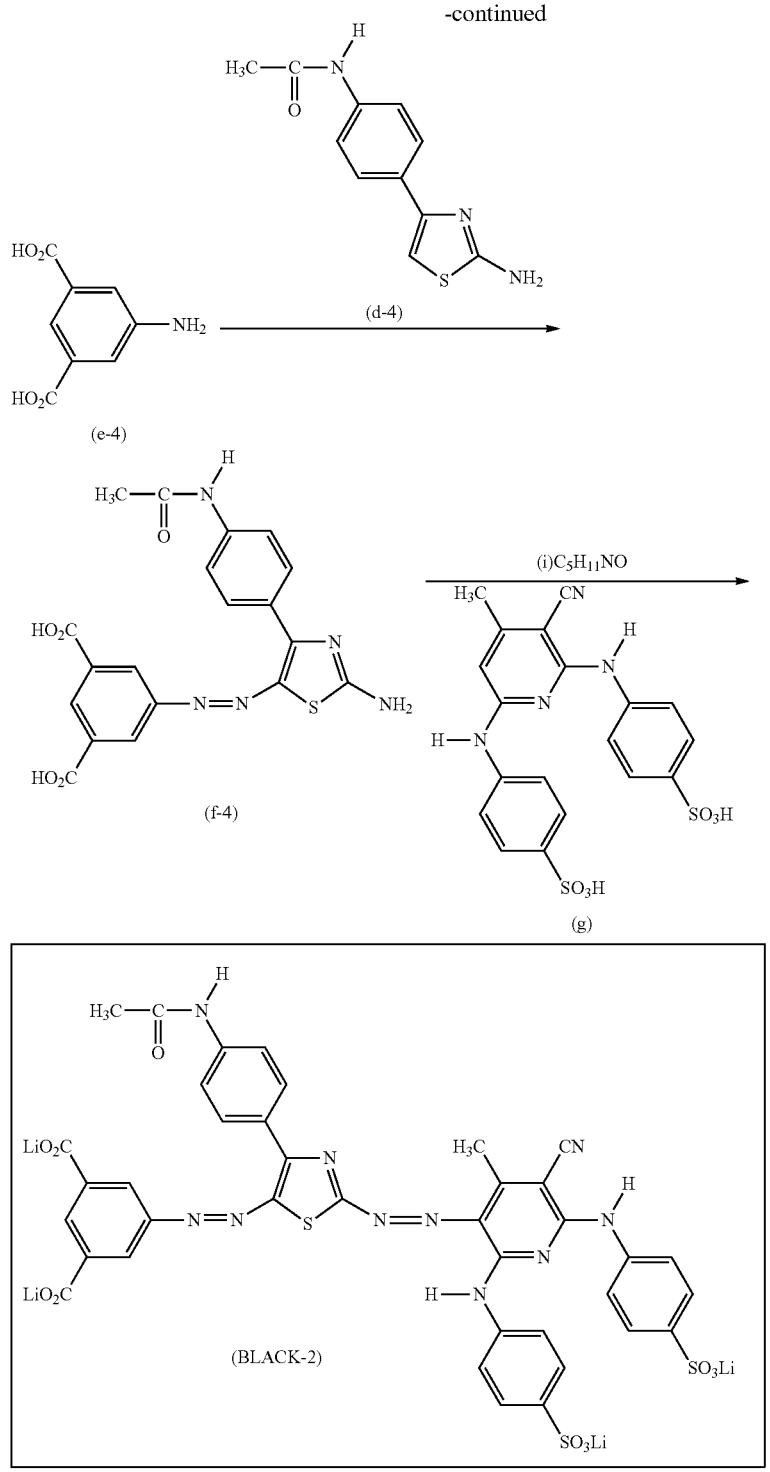

(1) Synthesis of Intermediates (b-1) and (c-1):
Synthesis was performed by the method described in Synthesis Example (1).

(2) Synthesis of Intermediate (d-4):
9.6 g of Intermediate (c-1) was added to 125 ml of acetone, and stirred and dissolved at the internal temperature of 50° C. After cooling was performed in an ice bath to the internal temperature of 4° C., 5.6 g of acetic anhydride was added dropwise for 15 minutes. After the temperature was increased to room temperature, 50 mL of water was added, and acetone was distilled off under reduced pressure. The crystal was separated by filtration, washed twice with 50 mL of water, and dried at 80° C. for 6 hours to obtain 9.9 g of a white crystal of Intermediate (d-4).

(3) Synthesis of Intermediate (f-4):
4.2 g of Intermediate (e-4) was added to 23 mL of water, and stirred at room temperature, and 5.9 mL of 12 N hydrochloric acid was added dropwise. 4.8 mL of the aqueous solution of 1.6 g of sodium nitrite was added dropwise while maintaining the internal temperature at 5° C. or below. After stirring was performed at the internal temperature of 5° C. or below for 2 hours, 0.1 g of urea was added, and stirred at that temperature for 15 minutes to obtain the diazonium solution. Separately, 4.5 g of Intermediate (d-4) and 11.5 g of lithium acetate were dissolved in 67 mL of methanol and 12 mL of dimethylacetamide, and cooled to the internal temperature of 2° C. The aforementioned diazonium solution was added dropwise at the internal temperature of 5° C. or below. After stirring was performed at the internal temperature 5° C. or below for 1.5 hours, 23 mL of isopropyl alcohol was added dropwise. The crystal was separated by filtration, and then washed with 100 mL of isopropyl alcohol. The crystal was added to 20 mL of water, and stirred at the internal temperature of 50° C. for 30 min, and then, 60 mL of isopropyl alcohol was added dropwise. The crystal was separated by filtration, and then washed with isopropyl alcohol. Drying was performed at 80° C. to obtain 7.6 g of a brown crystal of Intermediate (f-4).

(4) Synthesis of BLACK-2:

The pH of a solution of 7.6 g of Intermediate (f-4), 8.0 g of Intermediate (g), and 150 mL of water was adjusted to 2 or below by 12 N hydrochloric acid, and 12.2 g of isoamyl nitrite was added dropwise at the internal temperature of 35° C. to 40° C. After stirring at the internal temperature 40° C. for 4 hours, 30 mL of methanol and subsequently 17.4 g of lithium chloride were added. Further, 116 mL of isopropyl alcohol was added dropwise and cooled to room temperature. The crystal was separated by filtration, and then washed with 100 mL of isopropyl alcohol. 116 mL of water was added to the crystal, and the internal temperature was increased to 40° C. 348 mL of isopropyl alcohol was added dropwise for 20 min, stirred for 15 min, and then cooled to the internal temperature of 25° C. After the crystal was separated by filtration, 23.2 g of the obtained crystal was added to 116 mL of water, and the pH was adjusted to 8.3 with addition of 4 M lithium hydroxide aqueous solution. 487 mL of isopropyl alcohol was added dropwise thereto, and the crystal was separated by filtration. The isolated crystal was washed with 100 mL of isopropyl alcohol, and then dried at 80° C. 7.0 g of a black crystal of BLACK-2 was obtained.

Synthesis Example 5A

The synthesis scheme of BLACK-1 (M=Li) is as follows.

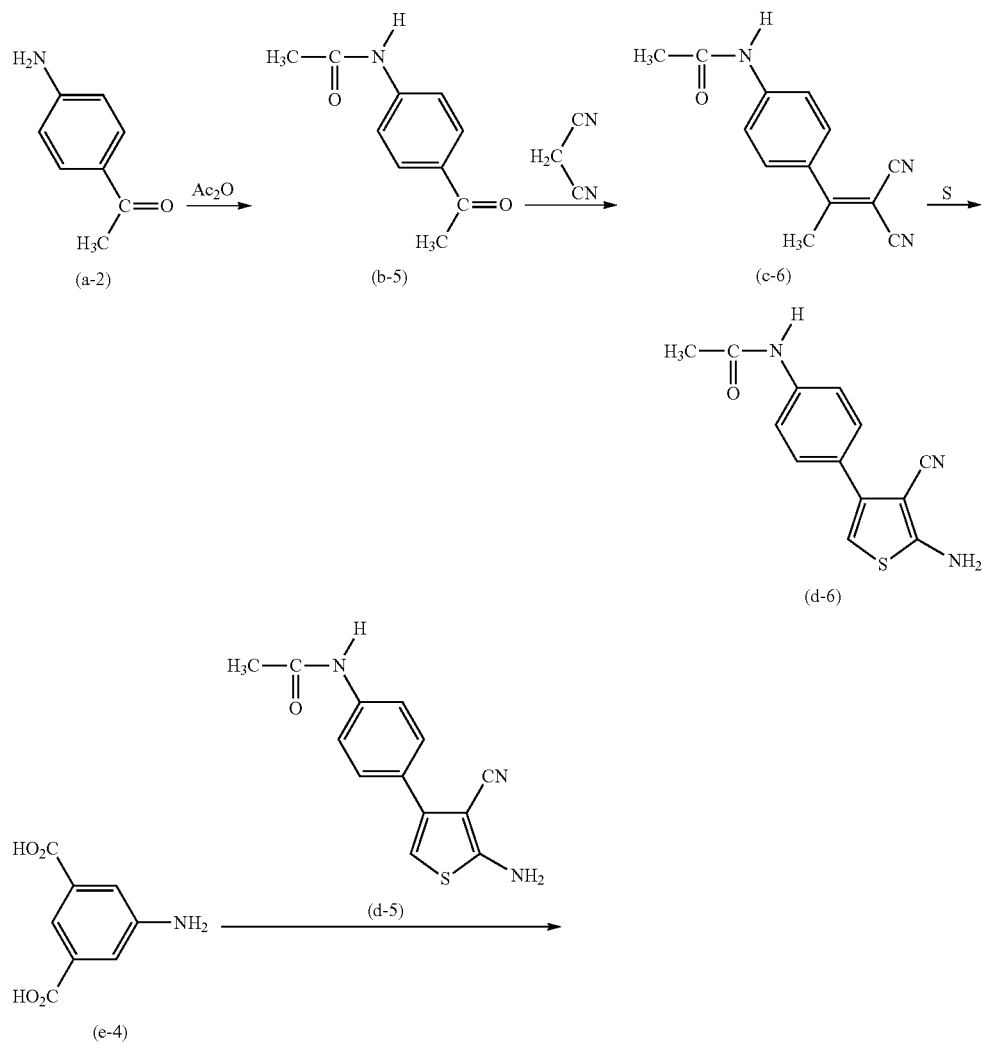

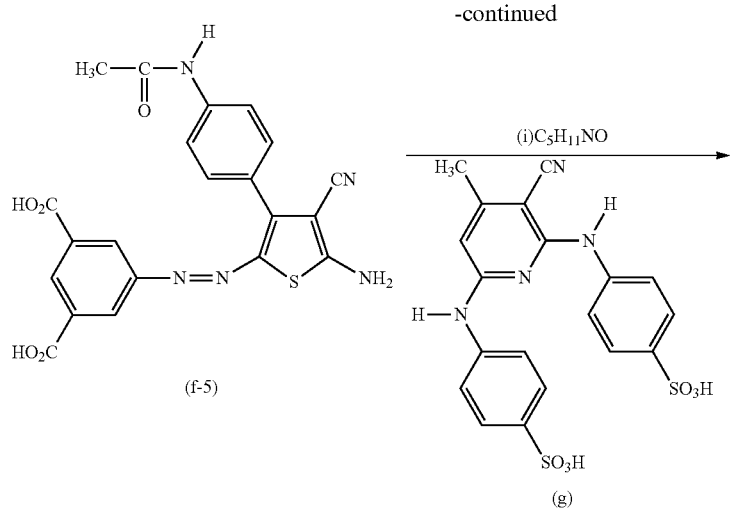

(f-5)             (g)

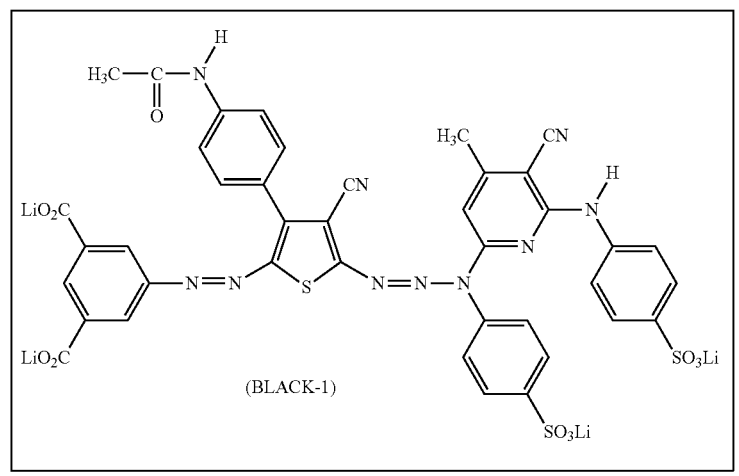

(BLACK-1)

(1) Synthesis of Intermediate (b-5):

20.3 g of p-aminoacetophenone (a-2; a product manufactured by Tokyo Chemical Industry Co., Ltd.) was added to 150 mL of acetonitrile, and completely dissolved by stirring at room temperature. Subsequently, 13.4 mL of pyridine was added, and the internal temperature was maintained at 4° C. in an ice bath. 11.8 g of acetic anhydride was added dropwise, and stirred at the internal temperature of 4° C. for 15 minutes. 300 mL of water, and subsequently, 5 mL of 12 N hydrochloric acid were added to the reaction solution, and the crystal was separated by filtration. After washing with 100 mL of water, drying was performed at 80° C. to obtain 18.6 g of a white crystal of Intermediate (b-5).

(2) Synthesis of Intermediate (c-5):

17.7 g of Intermediate (b-5), 7.3 g of malononitrile, 4.6 mL of acetic acid, 1.5 g of ammonium acetate, and 20 mL of toluene were put into 100 mL three-necked flask equipped with a Dean-Stark trap, and refluxed in an oil bath at 125° C. After stirring for 1 hour, 4.6 mL of acetic acid and 1.5 g of ammonium acetate were further added, and stirred under a reflux condition for 2 hours. After cooling in the air, 30 mL of methanol was added, and stirred in an ice bath for 30 minutes. The crystal was separated by filtration, washed with 20 mL of cold methanol, and dried. 12.1 g of a white crystal of Intermediate (c-5) was obtained.

(3) Synthesis of Intermediate (d-5):

1.5 g of sulfur was added to a solution of 11.3 g of Intermediate (c-5) and 20 mL of ethanol 20 mL, and 6.6 mL of triethylamine was then added dropwise. After stirring was performed at the internal temperature of 50° C. for 30 minutes, 500 mL of ethyl acetate and 300 mL of water were added, followed by stirring and then liquid separation. 200 mL of the saline solution was added to the organic layer, followed by stirring and then liquid separation, and magnesium sulfate was added to the organic layer and dried. After the organic solvent was distilled off, 50 mL of isopropanol was added, suspended, and stirred and the crystal was sparated by filtration. Drying was performed at 80° C. to obtain 8.1 g of a white crystal of Intermediate (d-5).

(4) Synthesis of Intermediate (f-5):

18.1 g of Intermediate (e-4) was added to 100 mL of water, and stirred at room temperature, and 25.7 mL of 12 N hydrochloric acid solution was added dropwise. 21 mL of an aqueous solution of 6.9 g of sodium nitrite was added dropwise at the internal temperature of 5° C. or below, and stirred for 2 hours. 0.7 g of urea was added, and stirred at the internal temperature of 5° C. for 15 minutes to obtain the diazonium solution. Separately, 25.7 g of Intermediate (d-5) and 30.0 g of lithium acetate were dissolved in 200 mL of methanol and 70 mL of dimethylacetamide, and the aforementioned diazonium solution was added dropwise at the internal temperature of 5° C. or below for 25 min. After stirring for 2 hours, 200 mL of isopropyl alcohol was added dropwise and the crystal was separated by filtration. After washing with 100 mL of isopropyl alcohol, the crystal was added to 150 mL of water, and stirred at the internal temperature of 50° C. for 30 minutes. After 400 mL of isopropyl alcohol was added dropwise, the crystal was separated by filtration, and washed with isopropyl alcohol. Drying was performed at 80° C. to obtain 35.0 g of a brown crystal of Intermediate (f-5).

(5) Synthesis of BLACK-1:

After the pH of a solution of 23.0 g of Intermediate (f-5), 27.6 g of Intermediate (g), and 460 mL of water was adjusted to 2 or below by 12 N hydrochloric acid, 17.6 g of isoamyl nitrite was added dropwise at the internal temperature of 25° C., and thereafter, stirring was performed at the internal temperature of 25° C. for 6 hours. The crystal separated by filtration with addition of 69.0 g of lithium chloride to the mixture solution, and then washed with 100 mL of isopropyl alcohol. The isolated crystal was added to 400 mL of water, and stirred at the internal temperature of 40° C. 700 mL of isopropyl alcohol was added dropwise thereto for 30 min. After stirring for 15 minutes, cooling was performed to the internal temperature of 25° C. and the crystal was separated by filtration. The obtained crystal was added to 100 mL of water, and stirred at the internal temperature of 40° C., and 300 mL of isopropyl alcohol was added dropwise. After cooling was performed to the internal temperature of 25° C., the crystal was separated by filtration. The isolated crystal was dissolved in the mixture solvent of 80 mL of water and 80 mL of methanol at the internal temperature of 40° C., and 300 mL of isopropyl alcohol was added dropwise. The precipitated crystal was separated by filtration, and then added to 50 mL of water, and 4 M lithium hydroxide aqueous solution was added until the pH was 8.3. 200 mL of isopropyl alcohol was added dropwise thereto. The precipitated crystal was separated by filtration, and then washed with 100 mL of isopropyl alcohol. Drying was performed at 80° C. to obtain 2.0 g of a black crystal of BLACK-1.

Synthesis Example 5B

The synthesis scheme of BLACK-1 (M=Li) is as follows.

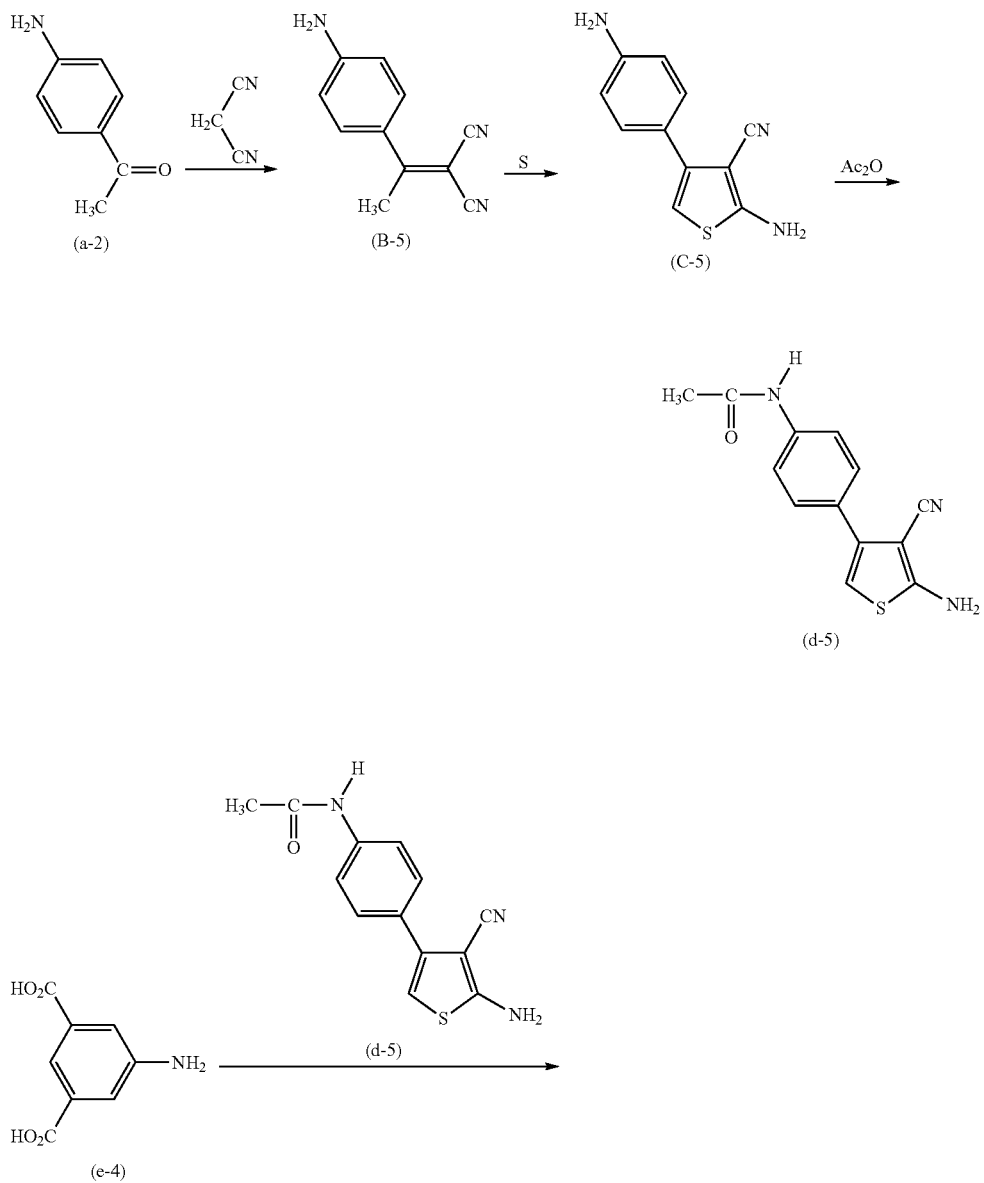

-continued

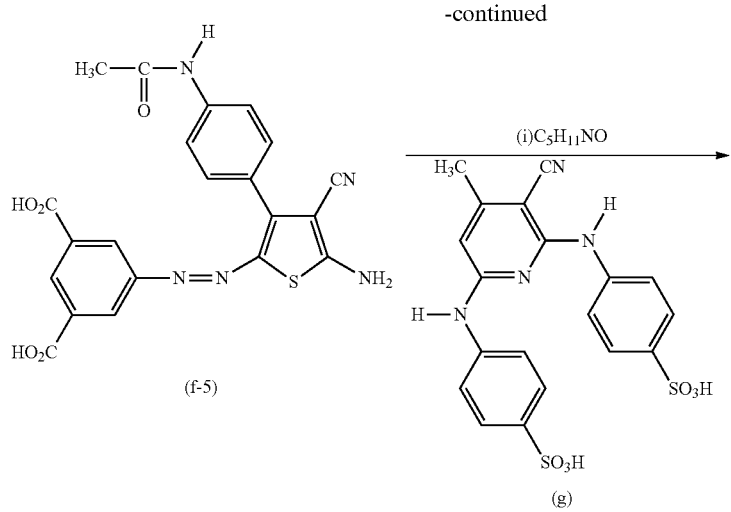

(f-5)

(g)

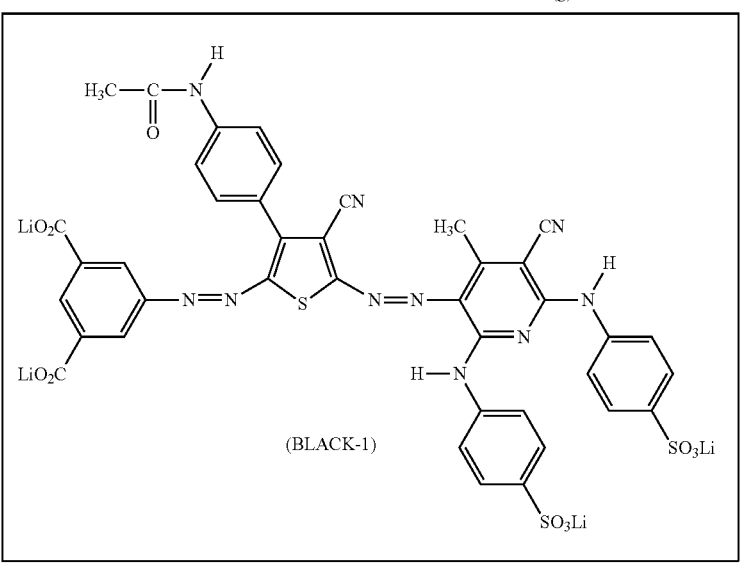

(BLACK-1)

(1) Synthesis of Intermediate (B-5):

14.1 g of aminoacetophenone (a-2), 8.3 g of malononitrile, 8.4 g of ammonium acetate, 9.8 g of acetic acid, and 50 mL of toluene were put into a three-necked flask equipped with a Dean-Stark trap, and increased to the internal temperature of 100° C. After stirring for 2 hours, cooling was performed to the internal temperature of 25° C. and the precipitated crystal was separated by filtration. The crystal was washed twice with 100 mL of isopropanol and then dried at 80° C. to obtain 18.4 g of Intermediate (B-5) as a yellow crystal.

(2) Synthesis of Intermediate (C-5):

13.3 g of Intermediate (B-5) and 4.6 g of sulfur were suspended in 270 mL of dimethylacetamide, 130 mL of acetonitrile, and 130 mL of water, and stirred at room temperature. 12.3 g of sodium hydrogen carbonate was added, and the temperature was increased to 40° C. After stirring for 1 hour and left standing to be cooled to room temperature, dust removal by filtration was performed to obtain 509.8 g of a 3.1 wt % brown solution of Intermediate (C-5).

(3) Synthesis of Intermediate (d-5):

192.7 g of the 3.1 wt % tea colored solution of Intermediate (C-5) was stirred at room temperature, and 2.8 g of acetic anhydride was added. After stirring for 30 minutes, 0.2 g of acetic anhydride was further added. After stirring for 70 minutes, 5.5 g of lithium acetate was added to obtain 199.6 g of a 5.1 wt % brown solution of Intermediate (d-5).

(4) Synthesis of Intermediate (f-5):

7.4 g of 5-aminoisophthalic acid (e-4) was suspended in 75 mL of water, and 10.0 mL of 12 N hydrochloric acid was added dropwise at room temperature. After cooling in an ice bath to the internal temperature of 4° C., 5.7 mL of an aqueous solution of 2.8 g of sodium nitrite was added dropwise at the internal temperature of 5° C. or below, and stirred for 2 hours. Thereafter, 0.5 g of amide sulfate was added, and stirred at the internal temperature of 5° C. for 15 minutes to obtain the diazonium solution. Separately, 199.6 g of Intermediate (d-5) was cooled to the internal temperature of 4° C., and the aforementioned diazonium solution was then added dropwise at the internal temperature of 6° C. or below for 25 minutes. After stirring at the internal temperature of 5° C. or below for 2 hours, the internal temperature was increased to 40° C. After stirring for 1.5 hours, the crystal was separated by filtration, and washed twice with 50 mL of isopropyl alcohol. Drying was performed at 80° C. to obtain 14.1 g of a brown crystal of Intermediate (f-5).

(5) Synthesis of BLACK-1:

The pH of the solution of 14.0 g of Intermediate (f-5), 16.8 g of Intermediate (g), and 280 mL of water was adjusted to 2 or below by 12 N hydrochloric acid, and 10.7 g of isoamyl nitrite was added dropwise at the internal temperature of 25° C. After stirring at the internal temperature of 25° C. for 6 hours, 4 M lithium hydroxide aqueous solution was added dropwise until the pH was 8.3. Subsequently, 840 mL of isopropyl alcohol was added dropwise, and the crystal was separated by filtration, and then washed twice with 200 mL of isopropanol. The isolated crystal was added to 500 mL of water, and stirring was performed at the internal temperature of 40° C. 1000 mL of isopropyl alcohol was added dropwise thereto for 30 minutes. After stirring for 15 minutes, cooling was performed to the internal temperature of 25° C. and the crystal was separated by filtration. The obtained crystal was added to 400 mL of water, and stirred at the internal temperature of 40° C., and 800 mL of isopropyl alcohol was added dropwise. After cooling to the internal temperature of 25° C., the crystal was separated by filtration, and then washed twice with 200 mL of isopropyl alcohol. Drying was performed at 80° C. to obtain 17.6 g of a black crystal of BLACK-1.

Synthesis Example 6

The synthesis scheme of BLACK-23 (M=Li) is as follows.

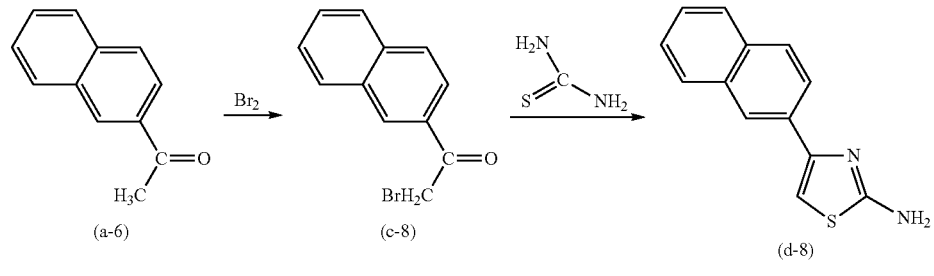

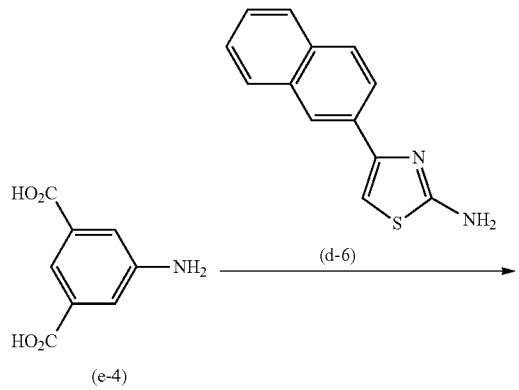

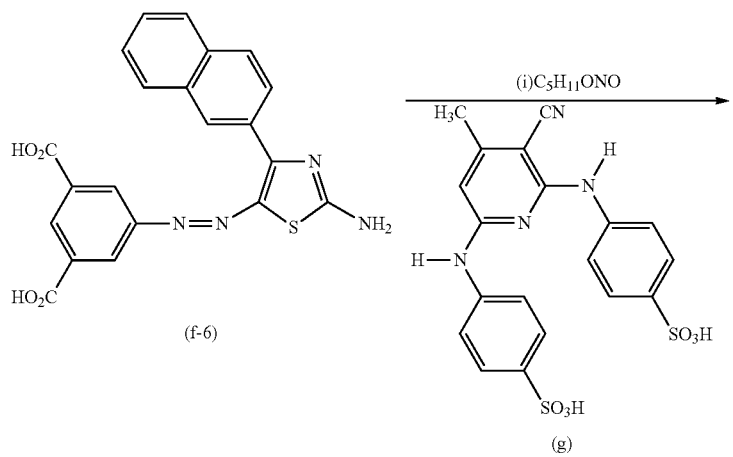

-continued

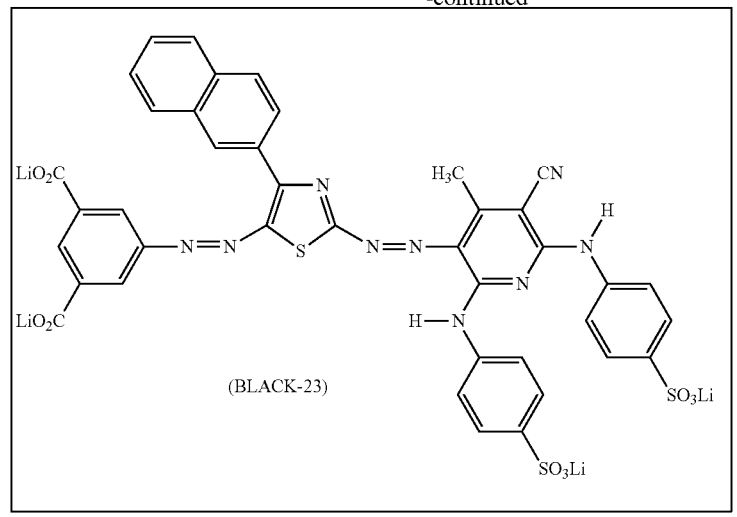

(BLACK-23)

(1) Synthesis of Intermediate (c-6):

A solution of 12.7 g of acetonaphthone and 50 mL of acetic acid was stirred at the internal temperature of 15° C., and 4.2 mL of bromine was added dropwise. The temperature was increased to room temperature, and stirring was then performed for 1 hour. The reaction mixture was added to 200 g of ice water and the crystal was separated by filtration. Washing was performed with 50 mL of water to obtain 22.5 g of a wet cake of Intermediate (c-6).

(2) Synthesis of Intermediate (d-6):

22.5 g of the wet cake of Intermediate (c-6) was suspended in 110 mL of water, and 5.7 g of thiourea was added. After stirring at the internal temperature of 95° C. for 2 hours, cooling was performed to room temperature. After the reaction solution was neutralized by 25% ammonia water, the crystal was separated by filtration, and washed with 50 mL of water. The crystal was suspended in 10 mL of methanol and 10 mL of ethanol, and stirred under reflux for 30 minutes. After cooling to the internal temperature of 15° C., the crystal was separated by filtration to obtain 5.4 g of a white crystal of Intermediate (d-6).

(3) Synthesis of Intermediate (f-6)

4.2 g of 5-aminoisophthalic acid (e-4) was suspended in 23 mL of water, and 6.5 mL of 12 N hydrochloric acid was added dropwise at room temperature. After cooling in an ice bath to the internal temperature of 4° C., 5.4 mL of an aqueous solution of 1.8 g of sodium nitrite was added dropwise while maintaining the internal temperature at 0° C. to 4° C., followed by stirring at the internal temperature of 5° C. or below for 2 hours. Thereafter, 0.1 g of urea was added, and stirred at the internal temperature of 5° C. for 15 minutes to obtain the diazonium solution.

Separately, 4.5 g of Intermediate (d-6) and 10.0 g of lithium acetate were dissolved in 50 mL of methanol and 14 mL of dimethylacetamide, and cooled to the internal temperature of 4° C., and the diazonium solution was added dropwise at the internal temperature of 5° C. or below for 15 min. After stirring was performed for 1.5 hours while maintaining the internal temperature at 5° C. or below, 60 mL of isopropyl alcohol was added dropwise. The crystal was separated by filtration, and then washed with 100 mL of isopropyl alcohol. The crystal was dissolved in 20 mL of water, and 60 mL of isopropyl alcohol was added dropwise at the internal temperature of 50° C. The crystal was separated by filtration, washed with 50 mL of isopropyl alcohol, and dried at 80° C. to obtain 7.8 g of a brown crystal of Intermediate (f-6).

(4) Synthesis of BLACK-23

7.0 g of Intermediate (f-6) and 7.7 g of Intermediate (g) were added to 32 mL of dimethylacetamide at the internal temperature of 40° C., and 3.0 g of isoamyl nitrite was added dropwise thereto. After stirring at the internal temperature 40° C. for 4 hours, 32 mL of isopropyl alcohol was added, and cooled to the internal temperature of 25° C. The precipitated crystal was separated by filtration, and washed with 50 mL of isopropyl alcohol. The obtained crystal was added to 56 mL of water at the internal temperature of 40° C., and 224 mL of isopropyl alcohol was added dropwise for 20 minutes and stirred for 15 minutes. After cooling to the internal temperature of 25° C., the crystal was separated by filtration, the obtained crystal was added to 19 mL of water and stirred, and 4 M lithium hydroxide aqueous solution was added until the pH was 8.3. 80 mL of isopropyl alcohol was added dropwise thereto. The precipitated crystal was separated by filtration, and washed with 30 mL of isopropyl alcohol. Drying was performed at 80° C. to isolate 1.1 g of a black crystal of BLACK-23.

Synthesis Example 7

A synthesis scheme of BLACK-11 (M:Li/Na≈70/30 (mol/mol)) is as follows.

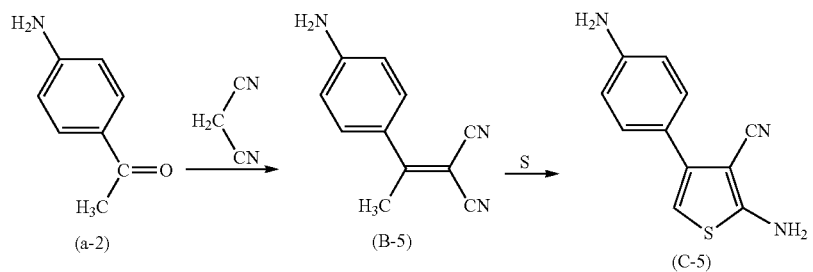
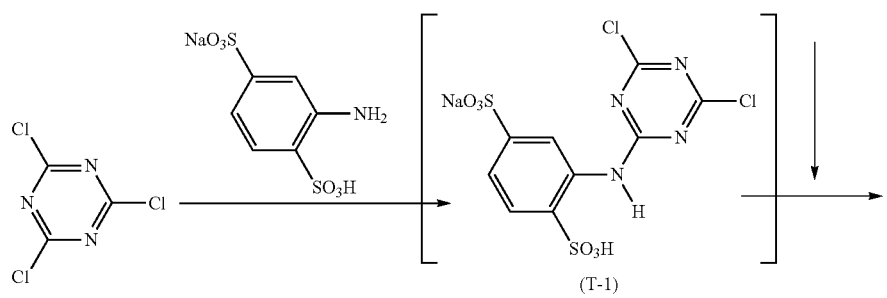
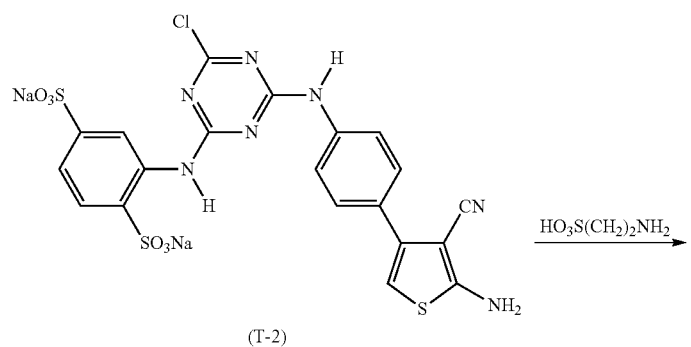
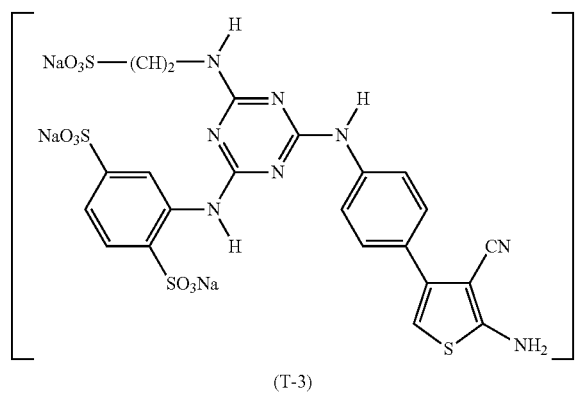

-continued
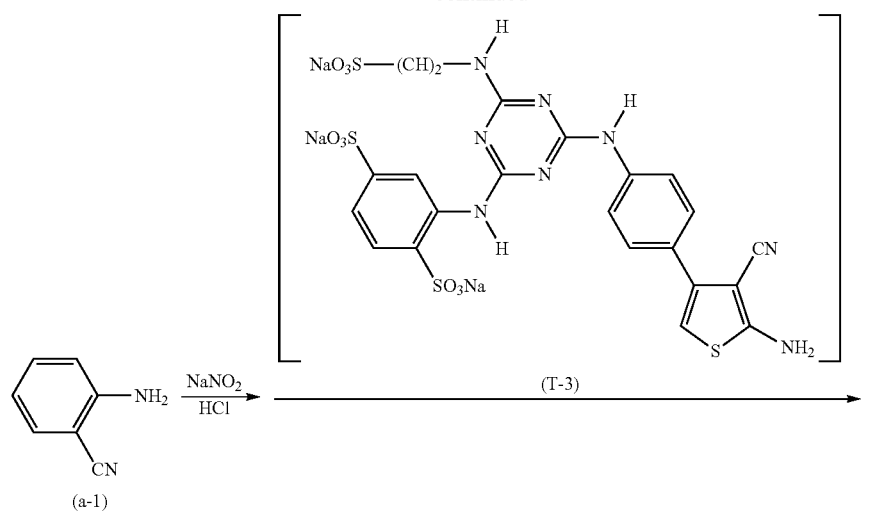
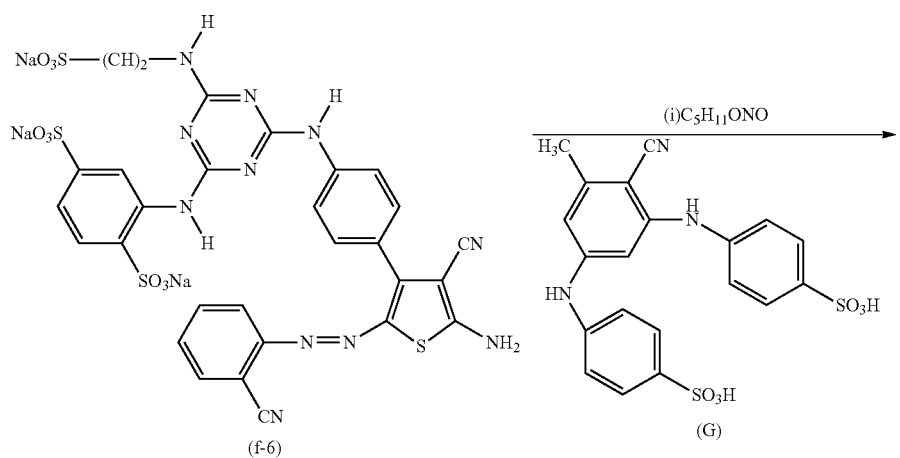
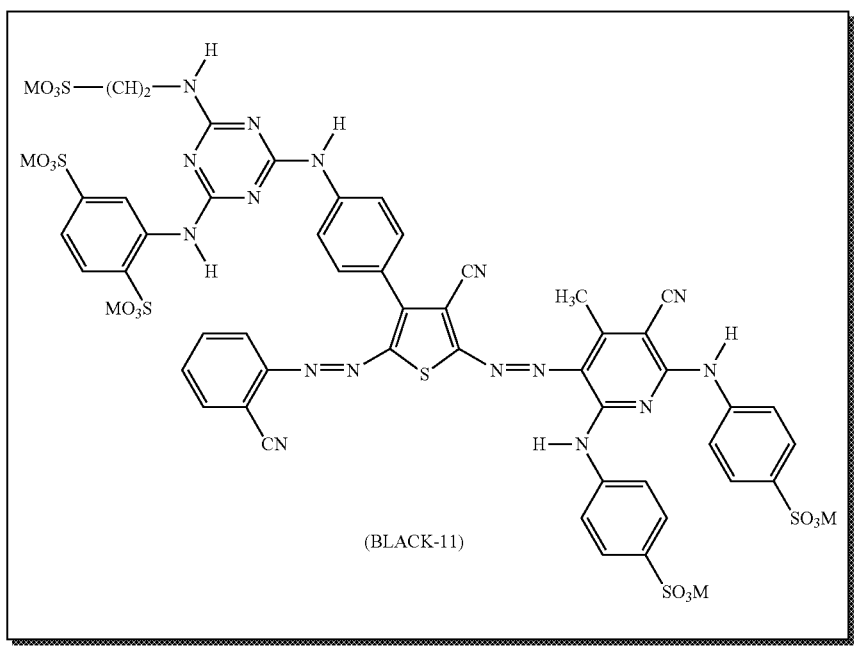

(1) Synthesis of Intermediate (B-5):

After 8.5 g of aminoacetophenone (a-2), 4.9 g of malononitrile, 26.5 mL of toluene, 5.0 g of ammonium acetate, and 5.9 g of acetic acid were added at room temperature, the internal temperature was increased to 100° C., and stirring was performed at the same temperature for 3 hours. After the reaction solution was cooled to 40° C., 31.8 mL of methanol was poured to be added, and stirred for 20 minutes, and the reaction solution was filtered. Washing was performed with 42.4 mL of isopropyl alcohol, and drying was performed at 60° C. for 8 hours. 11.1 g of (II-5) was obtained.

(2) Synthesis of Intermediate (C-5):

After 8.0 g of (B-5), 2.8 g of sulfur, 7.4 g of sodium hydrogen carbonate, 160 mL of dimethylacetamide, 80 mL of acetonitrile, and 80 mL of water were mixed at room temperature, the internal temperature was increased to 40° C., and stirring was performed at the same temperature for 1 hour. After the reaction solution was cooled to 25° C., an insoluble material was filtered to obtain (C-5) in a solution state.

(3) Synthesis of Intermediate (T-1):

100 mL of acetone was cooled to the internal temperature of 0° C., and 18.4 g of cyanuric chloride was added. Subsequently, 27.5 g of 2,5-disulfoaniline and 10.6 g of sodium carbonate were dissolved in 95 g of water, and added dropwise at the internal temperature of 0° C. to 4° C. or below for 30 minutes. After stirring at the internal temperature of 0° C. to 5° C. for 2.5 hours, 200 mL of methanol and 200 mL of isopropyl alcohol were added dropwise at the internal temperature of 5° C. or below, and the precipitated insoluble material was filtered to obtain (T-1) in a solution state.

(4) Synthesis of Intermediate (T-2):

While (T-1) obtained in Example (3) was maintained at the internal temperature of 20° C., 240.0 g of (C-5) was added dropwise. After the dropwise addition of (C-5), the internal temperature was increased to 30° C., and stirring was performed for 2.0 hours. 2.3 L of isopropyl alcohol was added dropwise at the internal temperature of 30° C. to 35° C. for 1 hour, and stirred at the same temperature for 30 min. The reaction solution was filtered, washed with isopropyl alcohol, and dried to obtain 24.0 g of (T-2).

(5) Synthesis of Intermediate (T-3):

8.0 g of taurine and 6.8 g of sodium carbonate were completely dissolved in 650 mL of water at room temperature, and 24.0 g of (T-2) was added as a powder to the solution. The internal temperature was increased to 100° C., and stirring was performed at the same temperature for 1.5 hours. The reaction solution was cooled to the internal temperature of 25° C. to obtain the intermediate (T-3) in a solution state.

(6) Synthesis of Intermediate (f-6):

58 mL of water was added to 4.4 g of 2-aminobenzonitrile (e-1), and stirred at room temperature, 10.5 mL of 12 M hydrochloric acid solution was added dropwise, and the reaction solution was cooled to the internal temperature of 0° C. While the internal temperature was maintained at 0° C. to 4° C., a 25% aqueous solution of 2.8 g of sodium nitrite was added dropwise, and stirred at the internal temperature of 0° C. to 5° C. for 1.5 hours. Thereafter, 0.4 g of urea was added and stirred for 15 min to obtain a diazonium salt solution. Separately from the diazonium salt solution, 300 mL of water was added to Intermediate (T-3) and cooled to the internal temperature of 2° C., the adjusted aforementioned diazonium salt solution was added dropwise at the internal temperature of 2° C. to 4° C. for 15 minutes. The internal temperature was maintained at 2° C. to 4° C. and stirring was performed for 2 hours to obtain (f-6) in a solution state.

(7) Synthesis of BLACK-11:

(f-6) obtained in Example (6) was stirred at room temperature, 17.7 g of the intermediate (g) was completely dissolved in 60 mL of water and added dropwise. 4.5 g of isoamyl nitrite was added dropwise at the internal temperature of 22° C., and stirred at the same temperature for 30 minutes. Thereafter, 0.2 g of isoamyl nitrite was further added dropwise, and stirred at the internal temperature of 22° C. for 2 hours. After the reaction solution was subjected to dust removal by filtration to remove insoluble material, 183 mL of dimethylacetamide was added to the reaction solution, and 1.1 L of isopropyl alcohol was added dropwise for 30 minutes. The slurry type reaction solution was filtered, and washed with 2 L of methanol to obtain coarse BLACK-11.

220 mL of water was added to the coarse powder, and dissolved therein, and 370 mL of isopropyl alcohol was added dropwise and filtered again to obtain a wet cake. The wet cake was completely dissolved in 220 mL of water, 1 N-lithium hydroxide aqueous solution was added to adjust the pH value to 8.3 (25° C.), and 100 mL of methanol was added to perform dust removal by filtration. The internal temperature of the solution was increased to 40° C., 300 mL of saturated LiCl isopropyl alcohol solution was added dropwise at the same temperature, and the precipitated crystal was filtered to obtain the wet crystal. 170 mL of water and 100 mL of methanol were added to the obtained wet crystal, and 430 mL of saturated LiCl isopropyl alcohol solution was added dropwise with stirred at the internal temperature of 40° C. and the precipitated crystal was separated by filtration. After washing with 500 mL of isopropyl alcohol, drying was performed at 40° C. for 12 hours to obtain 11.3 g of precise BLACK-11 (M:Li/Na≈70/30 (mol/mol)).

Further, the $L_1$ salt type ion exchange resin (manufactured by ORGANO CORPORATION, IR-120B was a $L_1$ type) was used with regard to the obtained BLACK-11 (M:Li/Na≈70/30 (mol/mol)) to obtain BLACK-11 (M:Li (that is, M is completely Li)).

[Preparation of the Aqueous Solution]

The aqueous solution of the present invention is called "the ink stock solution" herein.

Meanwhile, the pH of the aqueous solution was adjusted to 8.1 to 8.3 by using a 4 mol/L aqueous solution of lithium hydroxide.

Example-1

100 g of the compound (BLACK-21) (M=Li) of the present invention was dissolved in 900 g of ultrapure water with stirring at room temperature, and then added in divided portions to be dissolved, and 0.1 g of the preservative (PROXEL XL-II: manufactured by Fuji Film Imaging Colorant, Co., Ltd.) was added as a solid. The pH was adjusted to 8.2 (25° C.) by using a 4 mol/L aqueous solution of lithium hydroxide, and subsequently, unnecessary material was filtered by using a 0.2 μm membrane filter to obtain an ink stock solution-1.

Example-2

An ink stock solution-2 was obtained by performing the same operation as in Example-1, except that BLACK-20 (M=Li) was used instead of the compound (BLACK-21) of the present invention.

Example-3

An ink stock solution-3 was obtained by performing the same operation as in Example-1, except that BLACK-22 (M=Li) was used instead of the compound (BLACK-21) of the present invention.

Example-4

An ink stock solution-4 was obtained by performing the same operation as in Example-1, except that BLACK-2 (M=Li) was used instead of the compound (BLACK-21) of the present invention.

Example-5

An ink stock solution-5 was obtained by performing the same operation as in Example-1, except that BLACK-1 (M=Li) was used instead of the compound (BLACK-21) of the present invention.

Example-6

An ink stock solution-6 was obtained by performing the same operation as in Example-1, except that BLACK-23 (M=Li) was used instead of the compound (BLACK-21) of the present invention.

Example-7

An ink stock solution-7 was obtained by performing the same operation as in Example-1, except that BLACK-11 (M:Li/Na≈70/30 (mol/mol) was used instead of the compound (BLACK-21) of the present invention.

Example-8

0.1 g of lithium hydrogen carbonate (pH adjusting agent) was dissolved in 900 g of ultrapure water while stirring at room temperature, and subsequently, 100 g of the compound (BLACK-21) (M=Li) of the present invention was added in divided portions to be dissolved while stirring at room temperature, and 0.1 g of the preservative (PROXEL XL-11) was added as a solid. The pH was adjusted to 8.1 (25° C.) by using a 4 mol/L aqueous solution of lithium hydroxide, and subsequently, unnecessary material was filtered by using a 0.2 μm membrane filter to obtain an ink stock solution-8.

Example-9

An ink stock solution-9 was obtained by performing the same operation as in Example-8, except that BLACK-20 (M=Li) was used instead of the compound (BLACK-21) of the present invention.

Example-10

An ink stock solution-10 was obtained by performing the same operation as in Example-8, except that BLACK-22 (M=Li) was used instead of the compound (BLACK-21) of the present invention.

Example-11

An ink stock solution-11 was obtained by performing the same operation as in Example-8, except that BLACK-2 (M=Li) was used instead of the compound (BLACK-21) of the present invention.

Example-12

An ink stock solution-12 was obtained by performing the same operation as in Example-8, except that BLACK-1 (M=Li) was used instead of the compound (BLACK-21) of the present invention.

Example-13

An ink stock solution-13 was obtained by performing the same operation as in Example-8, except that BLACK-23 (M=Li) was used instead of the compound (BLACK-21) of the present invention.

Example-14

An ink stock solution-14 was obtained by performing the same operation as in Example-8, except that BLACK-11 (M:Li/Na 70/30 (mol/mol) was used instead of the compound (BLACK-21) of the present invention.

Example-15

An ink stock solution-15 was obtained by performing the same operation as in Example-1, except that the pH was not adjusted to 8.2 but 10.0.

Example-16

An ink stock solution-16 was obtained by performing the same operation as in Example-14, except that BLACK-11 (M:Li) was used instead of the compound (BLACK-11) (M:Li/Na 70/30 (mol/mol)) of the present invention.

Comparative Example-1

A comparative ink stock solution-01 was obtained by performing the same operation as in Example-8, except that the following compound (Dye-01) was used instead of the compound (BLACK-21) of the present invention.

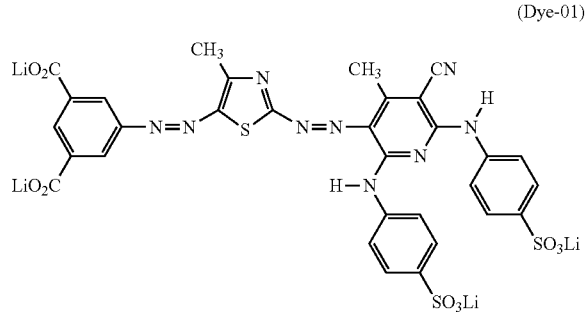

(Dye-01)

Comparative Example-2

A comparative ink stock solution-02 was obtained by performing the same operation as in Example-8, except that the following compound (Dye-02) was used instead of the compound (BLACK-21) of the present invention.

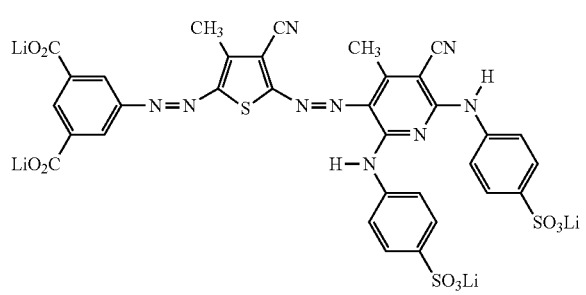

(Dye-02)

Comparative Example-3

A comparative ink stock solution-03 was obtained by performing the same operation as in Example-8, except that the following compound (Dye-03) was used instead of the compound (BLACK-21) of the present invention.

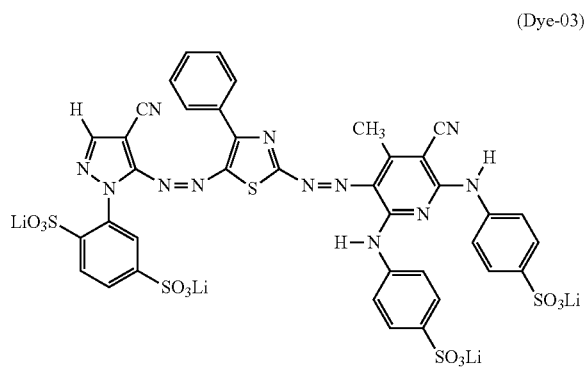

(Dye-03)

[Test Method of Storage Stability of the Ink Stock Solution]

The following levels were set with regard to a change in pH value based on a pH value (solution temperature of 25° C.) immediately after the ink stock solution was prepared and a pH value (solution temperature of 25° C.) after a forcible heat elapsed time test (7 days at 60° C.).

A: A difference between the pH values before and after the forcible heat elapsed time test is less than 0.3

B: A difference between the pH values before and after the forcible heat elapsed time test is 0.3 or more and less than 0.5

C: A difference between the pH values before and after the forcible heat elapsed time test is 0.5 or more and less than 0.7

D: A difference between the pH values before and after the forcible heat elapsed time test is 0.7 or more The following levels were set with regard to a change in ABS value based on the ABS (absorbance) value after the ink stock solution immediately after preparation of the ink stock solution was diluted by ultra-pure water to 1/5000 and the ABS value after the ink stock solution after the forcible heat elapsed time test (7 days at 60° C.) was diluted by ultra-pure water to 1/5000.

A: A difference between the ABS values before and after the forcible heat elapsed time test is less than 0.05

B: A difference between the ABS values before and after the forcible heat elapsed time test is 0.05 or more and less than 0.10

C: A difference between the ABS values before and after the forcible heat elapsed time test is 0.10 or more and less than 0.15

D: A difference between the ABS values before and after the forcible heat elapsed time test is 0.15 or more The ink stock solutions prepared in Examples-1 to 16 and Comparative Examples 1 to 3 were each stored at 60° C. for one week. Changes in liquid physical properties of the ink stock solution before and after the forcible heat elapsed time test are shown in the following Table 1.

TABLE 1

| | | Change in pH value (25° C.) | Change in asorbance (Aquous solution) |
|---|---|---|---|
| Example-1 | Ink stock solution-1 | B | A |
| Example-2 | Ink stock solution-2 | B | A |
| Example-3 | Ink stock solution-3 | B | A |
| Example-4 | Ink stock solution-4 | B | A |
| Example-5 | Ink stock solution-5 | B | A |
| Example-6 | Ink stock solution-6 | B | A |
| Example-7 | Ink stock solution-7 | A | A |
| Example-8 | Ink stock solution-8 | A | A |
| Example-9 | Ink stock solution-9 | A | A |
| Example-10 | Ink stock solution-10 | A | A |
| Example-11 | Ink stock solution-11 | A | A |
| Example-12 | Ink stock solution-12 | A | A |
| Example-13 | Ink stock solution-13 | A | A |
| Example-14 | Ink stock solution-14 | A | A |
| Example-15 | Ink stock solution-15 | B | B |
| Example-16 | Ink stock solution-16 | A | A |
| Comparative Example-1 | Comparative Ink stock solution-01 | C | C |
| Comparative Example-2 | Comparative Ink stock solution-02 | C | C |
| Comparative Example-3 | Comparative Ink stock solution-03 | C | D |

[Preparation of the Ink Composition]

Each ink composition was prepared based on the compositions shown in the following Tables 2-1 and 2-2. In the preparation method, the ink stock solution including the dye and the preservative was prepared in the same manner as in Example 1, the residual components were added thereto, diluted, and stirred at ambient temperature for 30 minutes, the pH thereof was adjusted to 8.2 (25° C.) by a 4 mol/L aqueous solution of lithium hydroxide, and the obtained solution was filtered by using the membrane filter having a mesh size of 1.0 μm to obtain each ink composition. Meanwhile, in Tables 2-1 and 2-2, the numerical value of each component represents % by mass of each component in the case where the mass of the ink composition is 100%, and "the residual" representing the amount of water represents the amount that is added to those of the components other than water to make the total sum of 100%.

Examples-21 to 43

Comparative Examples-21 to 24

Water-soluble ink for inkjet was prepared by using constitution of ink shown in Tables 2-1 and 2-2. The water-soluble dye for black ink adopted the compounds represented by the following Formulas (BLACK-1) to (BLACK-12) as an example of the azo colorant of the present invention. Further, from the viewpoint of hue adjustment, the compounds represented by the following Formulas (YELLOW-1) to (YELLOW-4) were used together as the dye for the complementary color.

In the following Tables 2-1 and 2-2, M of BLACK-1 to 10, 12, 51, and 52 is Li.

TABLE 2-1

|  | B-1 | B-2 | B-3 | B-4 | B-5 | B-6 | B-7 | B-8 | B-9 | B-10 | B-11 | B-12 |
|---|---|---|---|---|---|---|---|---|---|---|---|---|
| BLACK-1 | 6.0 | 6.0 | 6.0 | 6.0 |  |  |  | 4.0 | 4.0 | 4.0 |  |  |
| BLACK-2 |  |  |  |  | 6.0 | 6.0 |  |  |  |  |  |  |
| BLACK-3 |  |  |  |  |  |  | 6.0 |  |  |  |  |  |
| BLACK-4 |  |  |  |  |  |  |  | 2.0 |  |  |  |  |
| BLACK-5 |  |  |  |  |  |  |  |  | 2.0 |  |  |  |
| BLACK-6 |  |  |  |  |  |  |  |  |  | 2.0 |  |  |
| YELLOW-1 | 1.0 |  |  |  |  |  |  |  |  |  | 1.0 |  |
| YELLOW-2 |  | 1.0 |  |  |  |  |  |  |  |  |  | 1.0 |
| YELLOW-3 |  |  | 1.0 |  | 1.0 |  | 1.0 | 1.0 | 1.0 | 1.0 |  |  |
| YELLOW-4 |  |  |  | 1.0 |  | 1.0 |  |  |  |  |  |  |
| BLACK-13 |  |  |  |  |  |  |  |  |  |  | 6.0 |  |
| BLACK-14 |  |  |  |  |  |  |  |  |  |  |  | 6.0 |
| Glycerin | 8.0 | 8.0 | 8.0 | 8.0 | 8.0 | 8.0 | 8.0 | 8.0 | 8.0 | 8.0 | 8.0 | 8.0 |
| Triethylene glycol | 1.0 | 1.0 | 1.0 | 1.0 | 1.0 | 1.0 | 1.0 | 1.0 | 1.0 | 1.0 | 1.0 | 1.0 |
| Propylene glycol | 0.5 | 0.5 | 0.5 | 0.5 | 0.5 | 0.5 | 0.5 | 0.5 | 0.5 | 0.5 | 0.5 | 0.5 |
| 1,2-hexanediol | 2.0 | 2.0 | 2.0 | 2.0 | 2.0 | 2.0 | 2.0 | 2.0 | 2.0 | 2.0 | 2.0 | 2.0 |
| TEGmBE (*1) | 8.0 | 8.0 | 8.0 | 8.0 | 8.0 | 8.0 | 8.0 | 8.0 | 8.0 | 8.0 | 8.0 | 8.0 |
| OLFINE E1010 (*2) | 1.5 | 1.5 | 1.5 | 1.5 | 1.5 | 1.5 | 1.5 | 1.5 | 1.5 | 1.5 | 1.5 | 1.5 |
| 2-Pyrrolidone | 4.0 | 4.0 | 4.0 | 4.0 | 4.0 | 4.0 | 4.0 | 4.0 | 4.0 | 4.0 | 4.0 | 4.0 |
| Proxel XL-II | 0.2 | 0.2 | 0.2 | 0.2 | 0.2 | 0.5 | 0.2 | 0.2 | 0.2 | 0.2 | 0.2 | 0.2 |
| Lithium hydrogen carbonate | 0.1 | 0.1 | 0.1 | 0.1 | 0.1 | 0.1 | 0.1 | 0.1 | 0.1 | 0.1 | 0.1 | 0.1 |
| Water | Remainer | Remainer | Remainer | Remainer | Remainer | Remainer | Remainer | Remainer | Remainer | Remainer | Remainer | Remainer |

(*1): Triethylene glycol monobutyl ether
(*2): manufactured by Nissin Chemical Industry Co., Ltd.

TABLE 2-2

|  | B-13 | B-14 | B-15 | B-16 | B-17 | B-18 | B-19 | B-20 | B-21 | B-22 | B-23 | B-24 | B-25 | B-26 | B-27 |
|---|---|---|---|---|---|---|---|---|---|---|---|---|---|---|---|
| BLACK-7 | 6.0 |  |  |  |  |  |  |  |  |  |  |  |  |  |  |
| BLACK-8 |  | 6.0 |  |  |  |  |  |  |  |  |  |  |  |  |  |
| BLACK-9 |  |  | 6.0 |  |  |  |  |  |  |  |  |  |  |  |  |
| BLACK-10 |  |  |  | 6.0 | 6.0 |  |  |  |  |  |  |  |  |  |  |
| BLACK-11 (*1) |  |  |  |  |  | 6.0 | 6.0 | 6.0 | 6.0 |  |  |  |  |  |  |
| BLACK-11 (*1) |  |  |  |  |  |  |  |  |  |  |  |  |  |  | 6.0 |
| BLACK-12 |  |  |  |  |  |  |  |  |  | 6.0 |  |  |  |  |  |
| BLACK-51 |  |  |  |  |  |  |  |  |  |  | 6.0 |  |  |  |  |
| BLACK-52 |  |  |  |  |  |  |  |  |  |  |  | 6.0 |  |  |  |
| YELLOW-1 |  |  |  |  |  |  | 1.0 |  |  |  |  |  |  |  |  |
| YELLOW-2 |  |  |  |  |  | 1.0 |  |  |  |  |  |  |  |  |  |
| YELLOW-3 | 1.0 | 1.0 | 1.0 | 1.0 |  |  |  | 1.0 |  | 1.0 | 1.0 | 1.0 | 1.0 | 1.0 | 1.0 |
| YELLOW-4 |  |  |  |  | 1.0 |  |  |  | 1.0 |  |  |  |  |  |  |
| BLACK-13 |  |  |  |  |  |  |  |  |  |  |  |  | 6.0 |  |  |
| BLACK-14 |  |  |  |  |  |  |  |  |  |  |  |  |  | 6.0 |  |
| Glycerin | 8.0 | 8.0 | 8.0 | 8.0 | 8.0 | 8.0 | 8.0 | 8.0 | 8.0 | 8.0 | 8.0 | 8.0 | 8.0 | 8.0 | 8.0 |
| Triethylene glycol | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| 1,2-hexanediol | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| Propylene glycol | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| TEGmBE (*3) | 8.0 | 8.0 | 8.0 | 8.0 | 8.0 | 8.0 | 8.0 | 8.0 | 8.0 | 8.0 | 8.0 | 8.0 | 8.0 | 8.0 | 8.0 |
| Proxel GXL (S) | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| Lithium hydrogen carbonate | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |

TABLE 2-2-continued
|  | B-13 | B-14 | B-15 | B-16 | B-17 | B-18 | B-19 | B-20 | B-21 | B-22 | B-23 | B-24 | B-25 | B-26 | B-27 |
|---|---|---|---|---|---|---|---|---|---|---|---|---|---|---|---|
| Water | Remainer | Remainer | Remainer | Remainer | Remainer | Remainer | Remainer | Remainer | Remainer | Remainer | Remainer | Remainer | Remainer | Remainer | Remainer |
*1: M:Li/Na ≈ 70/30 (mol/mol)
*2: M:Li
*3: Triethylene glycol monobutyl ether
*4: manufactured by Nissin Chemical Industry Co., Ltd.
(YELLOW-1):
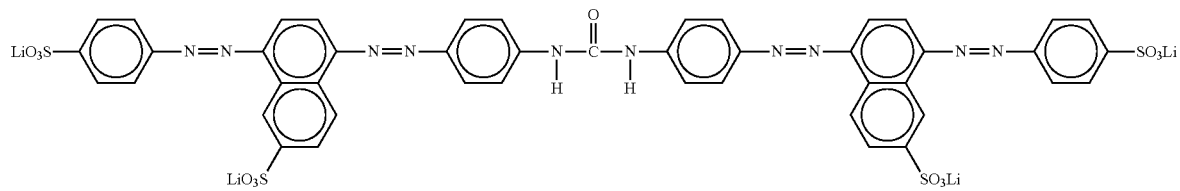
(YELLOW-2):
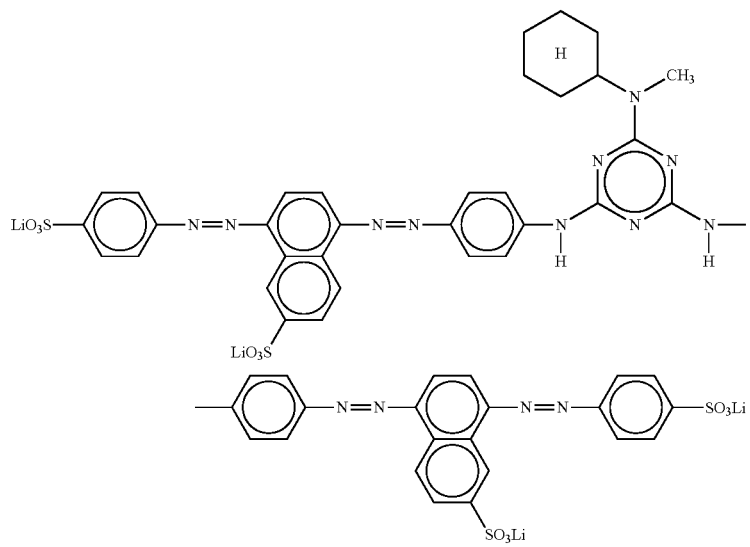
(YELLOW-3):
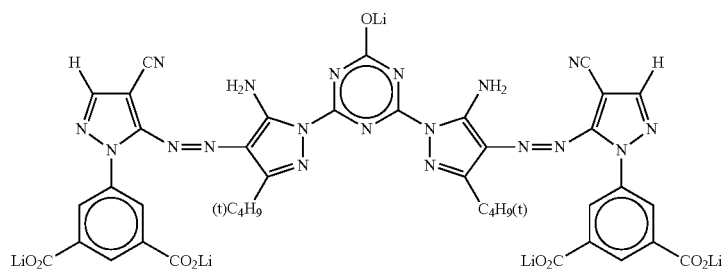
(YELLOW-4):
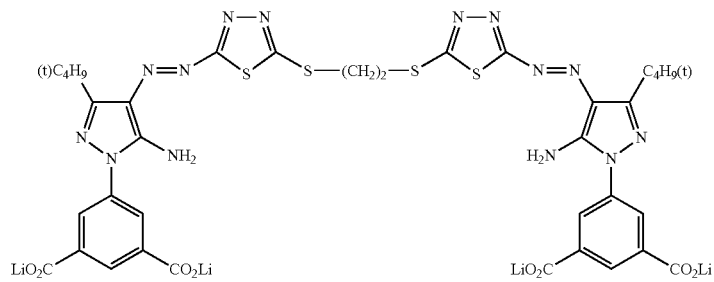

In addition, the following Formulas (BLACK-13) and (BLACK-14) were used as examples of the comparative dye other than the dyes represented by (BLACK-1) to (BLACK-12), (BLACK-51), and (BLACK-52) of the present invention.

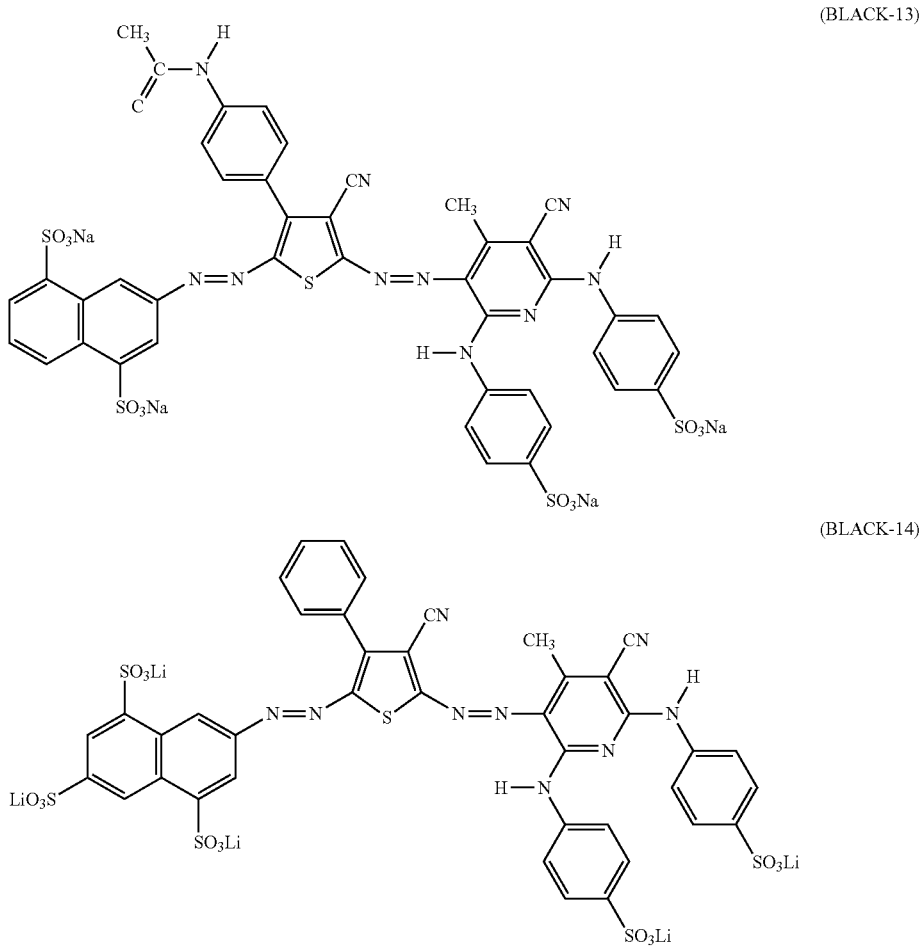

(BLACK-13)

(BLACK-14)

[Test Method of Storage Stability of Ink]

The following levels were set with regard to a change in pH value based on a pH value (solution temperature of 25° C.) immediately after the ink was prepared and a pH value (solution temperature of 25° C.) after the forcible heat elapsed time test (stored for 7 days at 60° C.).

A: A difference between the pH values before and after the forcible heat elapsed time test is less than 0.3

B: A difference between the pH values before and after the forcible heat elapsed time test is 0.3 or more and less than 0.5

C: A difference between the pH values before and after the forcible heat elapsed time test is 0.5 or more and less than 0.7

D: A difference between the pH values before and after the forcible heat elapsed time test is 0.7 or more The following levels were set with regard to a change in ABS value, based on the ABS (absorbance) value after the ink stock solution immediately after the ink solution was prepared was diluted by ultra-pure water to 1/4500 and the ABS value after the ink stock solution after the forcible heat elapsed time test (stored 7 days at 60° C.) was diluted by ultra-pure water to 1/4500.

A: A difference between the ABS values before and after the forcible heat elapsed time test is less than 0.05

B: A difference between the ABS values before and after the forcible heat elapsed time test is 0.05 or more and less than 0.10

C: A difference between the ABS values before and after the forcible heat elapsed time test is 0.10 or more and less than 0.15

D: A difference between the ABS values before and after the forcible heat elapsed time test is 0.15 or more Ink compositions B-01 to B-27 prepared based on the compositions described in Tables 2-1 and 2-2 were each stored at 60° C. for 3 days (forcible heat elapsed time test). A change in liquid physical properties of the ink composition before and after the forcible heat elapsed time test is shown as storage stability of ink in the following Table 3.

The image fastness (light resistance and ozone gas resistance) and the image quality (bronzing) were evaluated by printing monochromic image pattern of each color and green, red, and grey image patterns, which were formed of yellow, magenta, cyan and black and having concentrations stepwisely changed so that the OD value of each color was 0.7 to 1.8 on the exclusive recording medium for inkjet (picture paper <Gloss> (trade name, manufactured by Seiko Epson Corporation)) by using inkjet printer Stylus Color 880™ (trade name, manufactured by Seiko Epson Corporation) and the ink set.

[Test Method of Ozone Resistance]

The record was exposed to ozone gas for 14 days under the condition where the ozone gas concentration was set to 5 ppm (25° C.; 60% RH). The ozone gas concentration was set by using the ozone gas monitor manufactured by APPLICS, Co., Ltd. (Model: OZG-EM-01). At every predetermined elapsed time from the beginning of exposure, the OD value of each color recorded in each printed matter was measured by using a reflection concentration meter (X-Rite310TR). Meanwhile, the reflection concentration was measured at three points of 0.7, 1.0 and 1.8.

From the obtained results, the optical concentration remaining ratio (ROD) was obtained by using the following Equation: $ROD(\%) = (D/D_0) \times 100$. (In the Equation, D represents the OD value after the exposure test, and $D_0$ represents the OD value before the exposure test)

Further, the ozone resistance of each color recorded in the records was ranked A to D by using the following judgment criteria based on the aforementioned test results.

[Judgment Criteria]

Evaluation A: ROD 7 days after the test starts is 85% or more at all concentrations.

Evaluation B: ROD 7 days after the test starts is less than 85% at a concentration of any one point.

Evaluation C: ROD 7 days after the test starts is less than 85% at concentrations of any two points.

Evaluation D: ROD 7 days after the test starts is less than 85% at all concentrations.

In the present test, even though the records were exposed to ozone over a long period of time, the record having a small reduction in ROD is excellent. The obtained results are described as "ozone gas fastness" in Table 3.

[Test Method of Light Resistance]

Images were irradiated with a xenon light (100,000 lux) using a weather meter (manufactured by Atlas Co., Ltd.) for 14 days. At every predetermined elapsed time from the beginning of irradiation, the OD value of each color recorded in each printed matter was measured by using a reflection concentration meter (X-Rite310TR). Meanwhile, the reflection concentration was measured at three points of 0.7, 1.0 and 1.8.

From the obtained results, the optical concentration remaining ratio (ROD) was obtained by using the following Equation: $ROD(\%) = (D/D_0) \times 100$ (in the Equation, D represents the OD value after the exposure test, and $D_0$ represents the OD value before the exposure test).

Further, the light resistance of each color recorded in the records was ranked A to D by using the following judgment criteria based on the aforementioned test results.

[Judgement Criteria]

Evaluation A: ROD 14 days after the test starts is 85% or more at all concentrations.

Evaluation B: ROD 14 days after the test starts is less than 85% at a concentration of any one point.

Evaluation C: ROD 14 days after the test starts is less than 85% at concentrations of any two points.

Evaluation D: ROD 14 days after the test starts is less than 85% at all concentrations.

In the present test, even though the records were exposed to light over a long period of time, the record having a small reduction in ROD is excellent. The obtained results are described in Table 3.

Further, the following image quality (bronze gloss) evaluation was performed.

[Evaluation of Bronzing]

With regard to ink compositions B-01 to B-27, beta-printing using a black ink was performed on an inkjet recording medium (photo paper <Gloss>) so that the injection amount was 1.5 mg to 2.2 mg per square inch. The glossiness of the obtained printed matter was measured (measurement angle 60°) using a gloss meter (PG-1M, manufactured by Nippon Denshoku Industries Co., Ltd.). The printing was performed under two environments of 20° C. and 40% RH, and 35° C. and 60% RH. By using a rise value calculated based on the obtained glossiness and the following Equation as a criterion of judging the degree of occurrence of bronzing, judgment was performed based on the following judgment criteria. Rise value=glossiness (printed matter)−glossiness (recording medium)

[Judgement Criteria]

Evaluation A: less than 15

Evaluation B: 15 or more and less than 35

Evaluation C: 35 or more and less than 55

Evaluation D: 55 or more

The obtained result is represented by "image quality bronze" in Table 3.

TABLE 3

| | Ink composition | Ink storage stability pH | Ink storage stability ABS | Image quality bronze | light fastness | ozone gas fastness |
|---|---|---|---|---|---|---|
| Example-21 | B-01 | A | A | A | B | B |
| Example-22 | B-02 | A | A | A | B | B |
| Example-23 | B-03 | A | A | A | A | A |
| Example-24 | B-04 | A | A | A | B | A |
| Example-25 | B-05 | A | A | A | A | A |
| Example-26 | B-06 | A | A | A | B | A |
| Example-27 | B-07 | A | A | A | A | A |
| Example-28 | B-08 | A | A | A | A | A |
| Example-29 | B-09 | A | A | A | A | A |
| Example-30 | B-10 | A | A | A | A | A |
| Example-31 | B-13 | A | A | A | A | B |
| Example-32 | B-14 | A | A | A | B | A |
| Example-33 | B-15 | A | A | A | B | A |
| Example-34 | B-16 | A | A | A | A | A |
| Example-35 | B-17 | A | A | A | A | B |
| Example-36 | B-18 | A | A | A | A | B |
| Example-37 | B-19 | A | A | A | A | A |
| Example-38 | B-20 | A | A | A | A | A |
| Example-39 | B-21 | A | A | A | A | A |
| Example-40 | B-22 | A | A | A | A | B |
| Example-41 | B-23 | B | A | A | B | B |
| Example-42 | B-24 | B | A | A | B | B |
| Example-43 | B-27 | A | A | A | A | A |
| Comparative Example-21 | B-11 | B | B | D | C | C |
| Comparative Example-22 | B-12 | C | B | A | D | D |
| Comparative Example-23 | B-25 | B | B | D | C | C |
| Comparative Example-24 | B-26 | C | B | A | D | D |

From the above results, it can be seen that in the case where the ink composition of the present invention is used in inkjet recording, as compared to the Comparative Examples, storage stability is excellent, and a metal-like gloss, the so-called bronzing of a printed matter, can be improved to a higher level. Particularly, in Example 43 (ink using BLACK-11(M: Li) as a dye compound), the printing concentration is much higher and black is exhibited more clearly than expected, as compared to other matters.

Meanwhile, even in the case of changing the image-receiving paper (photo paper) used in the present invention to Color Picture Finishing Pro manufactured by Fujifilm Corporation or photo paper CRISPIA manufactured by EPSON, Co., Ltd., the same effect as the aforementioned result can be obtained.

INDUSTRIAL APPLICABILITY

An aqueous solution of the present invention has excellent storage stability, and a small change in physical properties of liquid (pH value, absorbance, viscosity, and surface tension), and does not generate precipitates, thus being useful to ink. Particularly, in ink for inkjet recording and an inkjet recording method using ink including an aqueous solution of the present invention, ink stability is high, a hue is favorable, and an image having high fastness to active gas, particularly ozone gas in light and an environment can be formed to remove a change in image quality of a record by a difference in recording paper, and particularly prevent a reduction in image quality of printed image (suppression of bronzing).

Moreover, the azo compound of the present invention may be used as a colorant, and is useful to aqueous ink. Ink using the azo compound of the present invention may provide a colored image or a colored material having excellent ink storage stability and excellent color and fastness.

The present invention has been described in detail with reference to specific embodiments, but it is apparent to the person with ordinary skill in the art that various changes or modifications may be made without departing from the spirit and the scope of the present invention.

This application is based on Japanese Patent Application Nos. 2010-173181, 2011-19344, and 2011-145021 filed on Jul. 30, 2010, Jan. 31, 2011, and Jun. 29, 2011 in the JPO, the disclosure of which is incorporated herein by reference in its entirety.

The invention claimed is:
1. An aqueous solution comprising:
(a) a preservative; and
(b) at least one azo compound represented by the following Formula (1) or a salt thereof,
wherein a content of (b) the at least one azo compound is 1% by mass to 25% by mass:

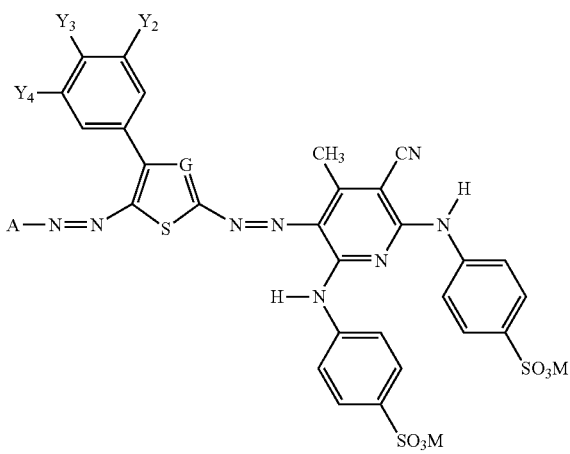

Formula (1)

wherein, in formula (1), A represents a substituted phenyl group or a substituted or unsubstituted nitrogen-containing 5-membered heterocyclic group,
G represents a nitrogen atom or —C($R_2$)=,
$R_2$ represents a hydrogen atom, a sulfo group, a carboxy group, a substituted or unsubstituted carbamoyl group or cyano group,
$Y_2$, $Y_3$ and $Y_4$ each independently represents a hydrogen atom or a monovalent substituent,
$Y_2$, $Y_3$ and $Y_4$ may be bonded to each other to form a ring,
all of $Y_2$, $Y_3$ and $Y_4$ do not represent a hydrogen atom at the same time, and
M each independently represents a hydrogen atom or a monovalent countercation, and at least one M is a lithium ion.

2. An aqueous solution comprising,
(a) a preservative; and
(b) at least one azo compound represented by the following Formula (2-1) or a salt thereof,
wherein a content of (b) the at least one azo compound is 1% by mass to 25% by mass:

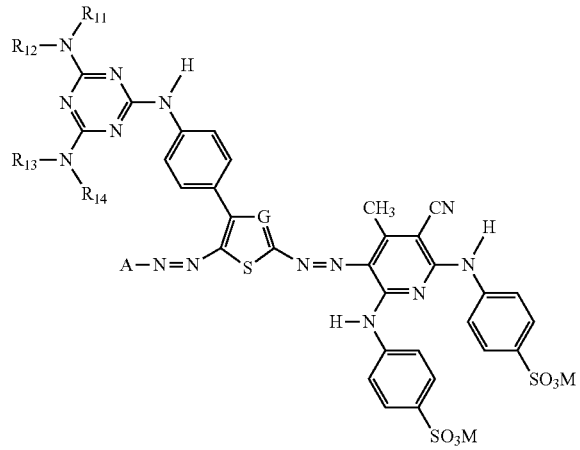

Formula (2-1)

wherein, in Formula (2-1), G represents a nitrogen atom or —C($R_2$)=,
$R_2$ represents a hydrogen atom, a sulfo group, a carboxy group, a substituted or unsubstituted carbamoyl group or cyano group,
$R_{11}$, $R_{12}$, $R_{13}$ and $R_{14}$ each independently represents a hydrogen atom or a monovalent substituent,
A represents a substituted phenyl group or a substituted or unsubstituted nitrogen-containing 5-membered heterocyclic group, and
M each independently represents a hydrogen atom or a monovalent countercation.

3. An aqueous solution comprising,
(a) a preservative; and
(b) at least one azo compound represented by the following Formula (3-1) or a salt thereof,
wherein a content of (b) the at least one azo compound is 1% by mass to 25% by mass:

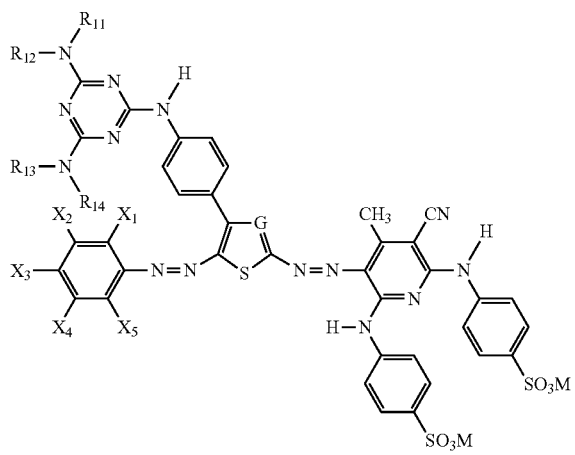

Formula (3-1)

wherein, in Formula (3-1), G represents a nitrogen atom or —C($R_2$)=, $R_2$ represents a hydrogen atom, a sulfo group, a carboxy group, a substituted or unsubstituted carbamoyl group or cyano group, $R_{11}$, $R_{12}$, $R_{13}$ and $R_{14}$ each independently represents a hydrogen atom or a monovalent substituent, $X_1$, $X_2$, $X_3$, $X_4$ and $X_5$ each independently represents a hydrogen atom or a monovalent substituent, and M each independently represents a hydrogen atom or a monovalent countercation.

4. An aqueous solution comprising,
(a) a preservative; and
(b) at least one azo compound represented by the following Formula (4-1) or a salt thereof,
wherein a content of (b) the at least one azo compound is 1% by mass to 25% by mass:

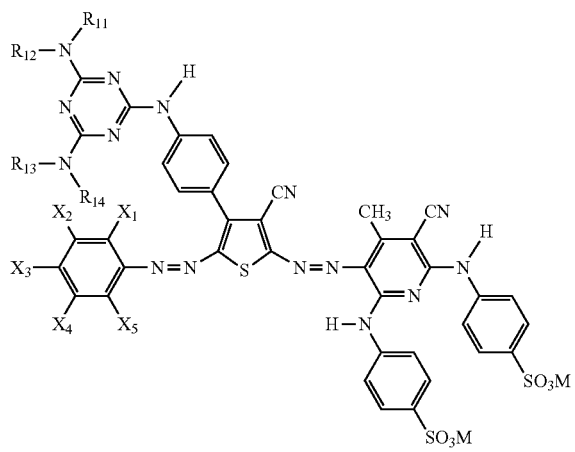

Formula (4-1)

wherein, in Formula (4-1), $R_{11}$, $R_{12}$, $R_{13}$ and $R_{14}$ each independently represents a hydrogen atom or a monovalent substituent, $X_1$, $X_2$, $X_3$, $X_4$ and $X_5$ each independently represents a hydrogen atom or a monovalent substituent, and M each independently represents a hydrogen atom or a monovalent countercation.

5. The aqueous solution according to claim 1,
wherein the azo compound represented by Formula (1) is an azo compound represented by the following Formula (2-2):

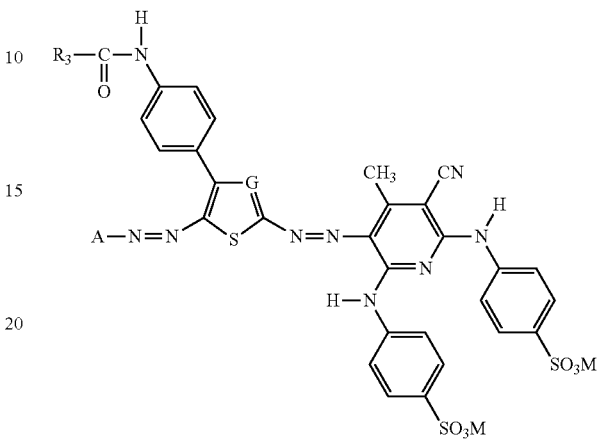

Formula (2-2)

wherein, in Formula (2-2), G represents a nitrogen atom or —C($R_2$)=, $R_2$ represents a hydrogen atom, a sulfo group, a carboxy group, a substituted or unsubstituted carbamoyl group or cyano group, $R_3$ represents a monovalent substituent, A represents a substituted phenyl group or a substituted or unsubstituted nitrogen-containing 5-membered heterocyclic group, and M each independently represents a hydrogen atom or a monovalent countercation, and at least one M is a lithium ion.

6. The aqueous solution according to claim 1,
wherein the azo compound represented by Formula (1) is an azo compound represented by the following Formula (3-2):

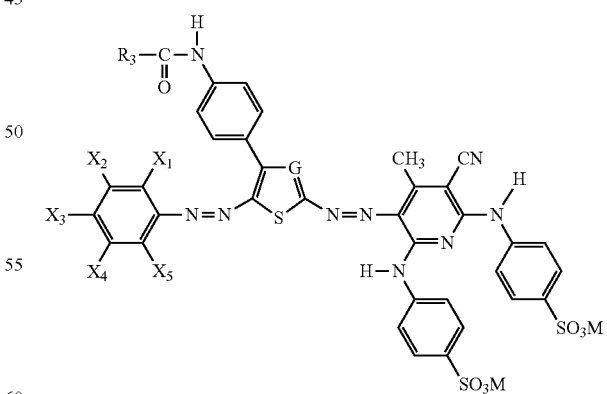

Formula (3-2)

wherein, in Formula (3-2), G represents a nitrogen atom or —C($R_2$)=, $R_2$ represents a hydrogen atom, a sulfo group, a carboxy group, a substituted or unsubstituted carbamoyl group or cyano group, $R_3$ represents a monovalent substituent, $X_1$, $X_2$, $X_3$, $X_4$ and $X_5$ each independently represents a hydrogen atom or a monovalent substituent, and M each independently represents a hydrogen atom or a monovalent countercation, and at least one M is a lithium ion.

7. The aqueous solution according to claim 1, wherein the azo compound represented by Formula (1) is an azo compound represented by the following Formula (4-2):

Formula (4-2)

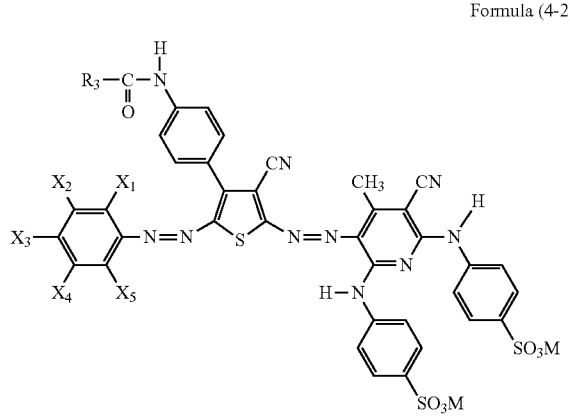

wherein, in Formula (4-2), $R_3$ represents a monovalent substituent, $X_1$, $X_2$, $X_3$, $X_4$ and $X_5$ each independently represents a hydrogen atom or a monovalent substituent, and M each independently represents a hydrogen atom or a monovalent countercation, at least one M is a lithium ion.

8. The aqueous solution according to claim 1, wherein the azo compound represented by Formula (1) has at least three or more ionic hydrophilic groups.

9. The aqueous solution according to claim 1, further comprising (c) a pH adjusting agent.

10. The aqueous solution according to claim 1, wherein a pH at 25° C. is 7.0 to 9.0.

11. An ink composition comprising the aqueous solution according to claim 1.

12. An ink for inkjet recording comprising the aqueous solution according to claim 1.

13. An inkjet recording method comprising forming a colored image on a recording target material by using the ink for inkjet recording according to claim 12.

14. An ink cartridge for inkjet recording, which is charged with the ink for inkjet recording according to claim 12.

15. An inkjet record, in which a colored image is formed on a recording target material by using the ink for inkjet recording according to claim 12.

16. An azo compound represented by the following Formula (3-1) or a salt thereof Formula (3-1)

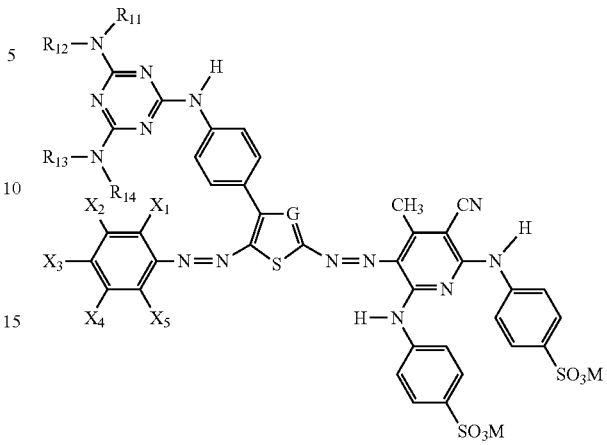

wherein, in Formula (3-1), G represents a nitrogen atom or —C($R_2$)=, $R_2$ represents a hydrogen atom, a sulfo group, a carboxy group, a substituted or unsubstituted carbamoyl group or cyano group, $R_{11}$, $R_{12}$, $R_{13}$ and $R_{14}$ independently represents a hydrogen atom or a monovalent substituent, $X_1$, $X_2$, $X_3$, $X_4$ and $X_5$ each independently represents a hydrogen atom or a monovalent substituent, and M each independently represents a hydrogen atom or a monovalent countercation.

17. The azo compound or the salt thereof according to claim 16, wherein the azo compound represented by Formula (3-1) is an azo compound represented by the following Formula (4-1):

Formula (4-1)

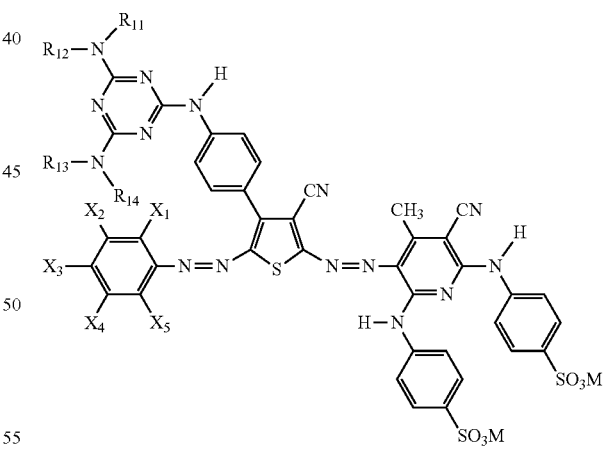

wherein, in Formula (4-1), $R_{11}$, $R_{12}$, $R_{13}$ and $R_{14}$ each independently represents a hydrogen atom or a monovalent substituent, $X_1$, $X_2$, $X_3$, $X_4$ and $X_5$ each independently represents a hydrogen atom or a monovalent substituent, and M each independently represents a hydrogen atom or a monovalent countercation.

18. The azo compound or the salt thereof according to claim 17, wherein the azo compound represented by Formula (4-1) is an azo compound represented by the following Formula (5):

Formula (5)
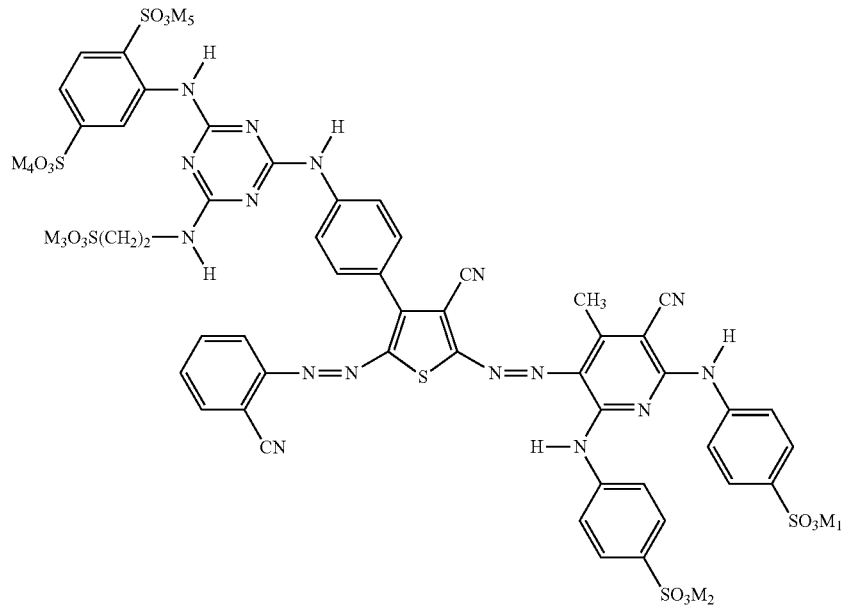
wherein, in Formula (5), $M_1$, $M_2$, $M_3$, $M_4$ and $M_5$ each independently represents a hydrogen atom or a monovalent countercation, and in the case where $M_1$, $M_2$, $M_3$, $M_4$ and $M_5$ represent a monovalent countercation, $M_1$, $M_2$, $M_3$, $M_4$ and $M_5$ represent a lithium ion, a sodium ion, a potassium ion or an ammonium ion.
* * * * *